US008101168B2

(12) United States Patent
Hassan et al.

(10) Patent No.: US 8,101,168 B2
(45) Date of Patent: Jan. 24, 2012

(54) ATTENUATED FNR DEFICIENT ENTEROBACTERIA

(75) Inventors: Hosni M. Hassan, Raleigh, NC (US); Ryan C. Fink, Naples, FL (US); Matthew R. Evans, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 186 days.

(21) Appl. No.: 12/500,366

(22) Filed: Jul. 9, 2009

(65) Prior Publication Data

US 2010/0255036 A1 Oct. 7, 2010

Related U.S. Application Data

(62) Division of application No. 11/780,358, filed on Jul. 19, 2007, now abandoned.

(60) Provisional application No. 60/831,821, filed on Jul. 19, 2006.

(51) Int. Cl.
*A01N 63/00* (2006.01)
*A61K 39/112* (2006.01)
*C12N 1/36* (2006.01)

(52) U.S. Cl. .................... 424/93.1; 424/258.1; 435/245; 435/252.8

(58) Field of Classification Search .................. 424/93.1, 424/258.1; 435/245, 252.8
See application file for complete search history.

(56) References Cited

U.S. PATENT DOCUMENTS

2006/0134135 A1 6/2006 Kroll et al.

FOREIGN PATENT DOCUMENTS

WO WO 01/21655 A2 3/2001
WO WO 01/21655 A3 3/2001

OTHER PUBLICATIONS

Ralph et al., 1998; Altering the anaerobic transcription factor FNR confers a hemolytic phenotype on *Escherichia coli* K12, PNAS pp. 10449-10452.*
Fink et al., Session No. 239/H. Abstract H—095, Jun. 8, 2005.
Baltes et al., "Deletion of the Anaerobic Regulator HlyX Causes Reduced Colonization and Persistence of *Actinobacillus pleuropneumoniae* in the Porcine Respiratory Tract", Infection and Immunity, American Society for Microbiology—Washington, 73:8, pp. 4614-4619 (Aug. 1, 2005). XP-002493398.
International Search Report and Written Opinion (17 pages) corresponding to PCT/US2007/016357; Mailing Date: Nov. 10, 2008.
Zheng et al., "*A Single Dose of Oral DNA Immunization Delivered by Attenuated Salmonella typhimurium Down-Regulates Transgene Expression in HBsAg Transgenic mice*", European Journal of Immunology, 32:11, pp. 3294-3304 (Nov. 2002). XP-002501710.
Bartolini et al. "Role of FNR and FNR-regulated, sugar fermentation genes in *Neisseria meningitides* infection" *Molecular Microbiology* 60(4):963-972 (2006).
Chatfield et al. "Use of the *nirB* Promoter to Direct the Stable Expression of Heterologous Antigens in *Salmonella* Oral Vaccine Strains: Development of a Single-Dose Oral Tetanus Vaccine" *Bio/Technology* 10d:888-892 (1992).
Chauhan et al. "Immunogenicity of cholera toxin B epitope inserted in *Salmonella* flagelling expressed on bacteria and administered as DNA vaccine" *Molecular and Cellular Biochemistry* 276:1-6 (2005).
Chincilla et al. "Enhanced Immunity to *Plasmodium falciparum* Circumsporozoite Protein (PfCSP) by Using *Salmonella enterica* Serovar Typhi Expressing PfCSP and a PFCSP-Encoding DNA Vaccine in a Heterologous Prime-Boost Strategy" *Infection and Immunity* 75(8):3769-3779 (2007).
Constantinidou et al. "A Reassessment of the FNR Regulon and Transcriptomic Analysis of the Effects of Nitrate, Nitrite and NarXL, and NarQP as *Escherichia coli* K12 Adapts from Aerobic to Anaerobic Growth" *Journal of Biological Chemistry* 281(8):4802-4815.
Curtiss III, et al. "Nonrecombinant and recombinant avirulent *Salmonella* vaccines for poultry" *Veterinary Immunology and Immunopathology* 54:365-372 (1996).
Filiatrault et al. "Identification of *Pseudomonas aeruginosa* Genes Involved in Virulence and Anaerobic Growth" *Infection and immunity* 74(7):4237-4245 (2006).
Fink et al. "FNR is a Global Regulator in Anaerobically Grown *Salmonella typhimurium*" 105$^{th}$ *General Meeting for the American Society for Microbiology*, Atlanta, GA (1 page) (2005).
Fink et al. "FNR is a Global Regulator of Virulence and Anaerobic Metabolism in *Salmonella enterica* Serovar *typhimurium* Atcc 14028s)" *Journal of Bacteriology* 189(6):2262-2273 (2007).
Fink et al. "Series GSE3657—FNR—vs WT in anoxic conditions" *NCBI Gene Expression Omnibus* (2 pages) (2007).
Galán et al. "Cloning and characterization of the *asd* gene of *Salmonella typhimurium*: use in stable maintenance of recombinant plasmids in *Salmonella* vaccine strains" *Gene* 94:29-35 (1990).
Jones et al. "Regulation of *Escherichia coli* fumarate reductase (frdABCD) operon expression by respiratory electron acceptors and the fnr gene product" *Journal of Bacteriology* 169(7):3340-3349 (1987).
Kang et al. "Genome-Wide Expression Analysis Indicates that FNR of *Escherichia coli* K-12 Regulates a Large Number of Genes of Unknown Function" *Journal of Bacteriology* 187(3):1135-1160 (2005).
Lee et al. "The ability of *Salmonella* to enter Mammalian cells is affected by bacterial growth state" *Proc. Nat. Acad. Sci., USA* 87:4304-4308 (1990).
Rollenhagen et al. "*Salmonella enterica* Highly Expressed Genes are Disease Specific" *Infection and Immunity* 74(3):1649-1660 (2006).
Rothery et al. "Defining the Qp-site of *Escherichia coli* fumarate reductase by site-directed mutagenesis, fluorescence quench titrations and EPR spectroscopy" *FEBS Journal* 272:313-326 (2005).
Salmon et al. "Global Gene Expression Profiling in *Escherichia coli* K12—The Effects of Oxygen Availability and FNR" *The Journal of Biological Chemistry* 278(32):29837-29855 (2003).
Strauch et al. "Oxygen Regulation in *Salmonella typhimurium*" *Journal of Bacteriology* 161(2):673-680 (1985).
Wei et al. "Characterization of a Group of Anaerobically Induced, *fnr*-Dependent Genes of *Salmonella typhimurium*" *Journal of Bacteriology* 181(19):6092-6097 (1999).

* cited by examiner

*Primary Examiner* — Maria Leavitt

(74) *Attorney, Agent, or Firm* — Myers Bigel Sibley & Sajovec, PA

(57) ABSTRACT

The invention provides an attenuated enterobacterium comprising an attenuating mutation in the fnr gene, and optionally further comprising a heterologous nucleic acid encoding a foreign antigen. Also provided are pharmaceutical formulations comprising the attenuated enterobacteria of the invention. Further disclosed are methods of inducing an immune response in a subject by administration of an immunogenically effective amount of an attenuated enterobacterium or pharmaceutical formulation of the invention.

19 Claims, 8 Drawing Sheets

ATTENUATED FNR DEFICIENT ENTEROBACTERIA

CROSS REFERENCE TO RELATED APPLICATION

This application is a divisional of U.S. application Ser. No. 11/780,358 filed Jul. 19, 2007 now abandoned, which claims the benefit of U.S. Provisional Application No. 60/831,821, filed Jul. 19, 2006, the disclosures of which are incorporated by reference herein in their entireties.

FIELD OF THE INVENTION

This invention relates to attenuated Fumarate-Nitrate Reductase (FNR) enterobacteria strains. In particular, this invention relates to attenuated FNR enterobacteria strains and methods of using the same to induce an immune response.

BACKGROUND OF THE INVENTION

*Salmonella enterica* serovar Typhimurium is a gram-negative facultative intracellular pathogen. Serovar Typhimurium infections usually result from ingestion of contaminated food or water. The organism generally targets and colonizes the intestinal epithelium of the host and causes gastroenteritis (i.e., salmonellosis). During a *Salmonella* infection, the growth phase and growth conditions of the organism are important in attachment, invasion, and the regulation of many of the virulence genes. Cells grown under limited oxygen concentrations are more invasive and adhere better to mammalian cells than do aerobically grown or stationary-phase cells. *Salmonella* invasion genes have been identified and localized. During infection, serovar Typhimurium must adapt to changes in $[O_2]$ encountered in the gastrointestinal tract of the host. In *Escherichia coli*, transitions from aerobic to anaerobic environments or vice versa, involve changes in a large number of genes. However, upon sudden reappearance of oxygen, these cellular processes must be reversed in a precise and orderly fashion to ensure the safe transition to the oxygenated environment. This complex regulatory system has been extensively studied in *E. coli*, where the DNA-binding protein FNR encoded by fnr, senses changes in $[O_2]$ and controls the expression of the different genes either alone or in cooperation with other regulators, e.g., ArcA.

SUMMARY OF THE INVENTION

The present invention is based, in part, on the inventors' discovery that enterobacteria comprising an attenuating mutation in the fnr (Fumarate-Nitrate Reductase) gene have an avirulent (i.e., highly attenuated) phenotype. Thus, the present invention provides attenuated enterobacteria and methods of using the same as attenuated immunogenic compositions, attenuated vaccines and/or as attenuated vaccine vectors to induce an immune response against a heterologous antigen in a subject.

Accordingly, a first aspect of the invention provides a pharmaceutical composition comprising an attenuated enterobacterium comprising an attenuating mutation (e.g., deletion) in the fnr gene in a pharmaceutically acceptable carrier.

A further aspect of the invention provides an attenuated enterobacterium comprising an attenuating mutation (e.g., a deletion) in the fnr gene and, optionally, further comprising a heterologous nucleic acid sequence encoding a foreign antigen. In particular embodiments, the attenuated enterobacterium is present in a pharmaceutical composition in a pharmaceutically acceptable carrier.

A further aspect of the present invention is a method of inducing an immune response in a subject comprising administering to the subject an immunogenically effective amount of an attenuated enterobacterium comprising an attenuating mutation (e.g., a deletion) in the fnr gene. In embodiments of the invention, the attenuated enterobacterium is provided in a pharmaceutical composition further comprising a pharmaceutically acceptable carrier. In further embodiments of the invention, the attenuated enterobacterium comprises a heterologous nucleic acid encoding a foreign antigen.

The invention further provides for the use of an attenuated enterobacterium or pharmaceutical composition of the invention to induce an immune response in a subject.

These and other aspects of the invention are set forth in more detail in the following description of the invention.

DETAILED DESCRIPTION OF THE INVENTION

Figure 1:
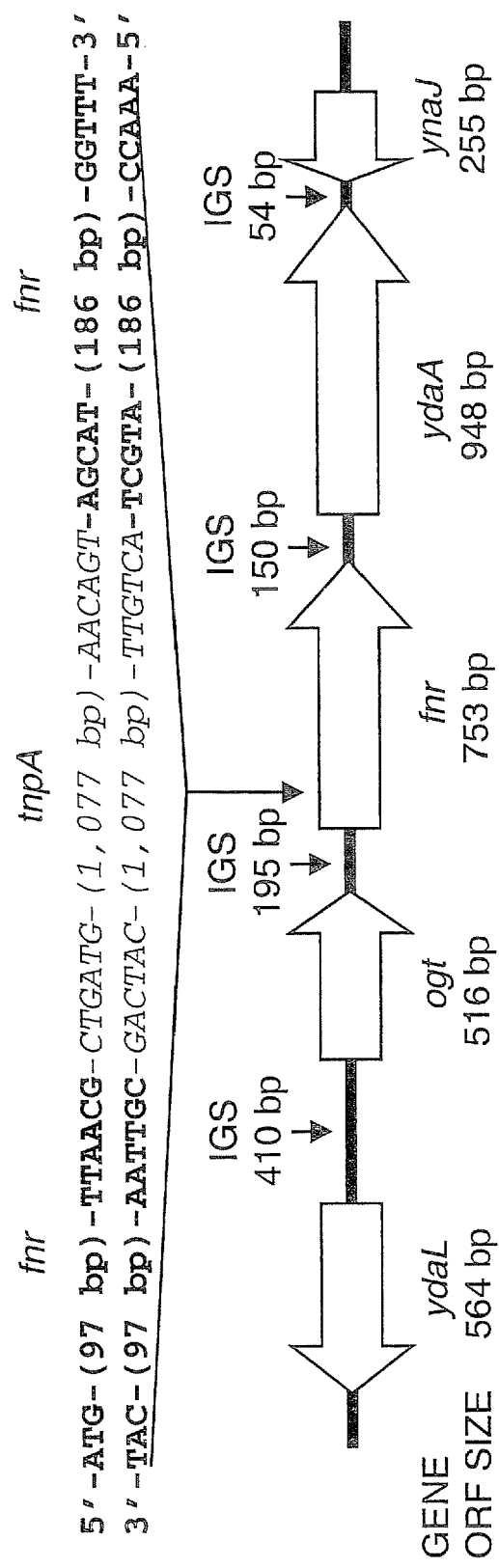
FIG. 1 shows the location of the tnpA insertion (between by 106 and 107) in the fnr gene. WT fnr sequences are in bold, and the sequences of the beginning and ending junctions of the tnpA insert are in italics. Arrows indicate the direction of transcription. IGS, intergenic spacer region. (Complete DNA sequences [i.e., ogt, tnpA/fnr junctions, and ydaA] are available at GenBank accession number AH015911.)

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations, and variations thereof.

All publications, patents, and patent publications cited herein are incorporated by reference in their entireties for the teachings relevant to the sentence and/or paragraph in which the citation is presented.

As used herein, "a," "an" or "the" can mean one or more than one. For example, "a" mutation can mean a single mutation or a multiplicity of mutations.

As used herein, "and/or" refers to and encompasses any and all possible combinations of one or more of the associated listed items, as well as the lack of combinations when interpreted in the alternative ("or").

FNR (Fumarate-Nitrate Reductase) is a DNA-binding regulator protein expressed by all enterobacteria including *Salmonella* spp., *Escherichia* spp., and *Shigella* spp. The fnr gene was previously known as oxrA in *Salmonella* spp. The present inventors have identified FNR as a global regulatory protein for the expression of virulent genes in enterobacteria. An FNR deleted (Δfnr) strain of a known virulent strain of *S. enterica* serovar Typhimurium was shown to be non-motile, lacking flagella, and having an avirulent phenotype. Thus, the present invention provides FNR deficient (e.g., Δfnr or fnr mutants) strains of enterobacteria that can be used to study the fnr gene, its role in virulence in these organisms, and can further be used as attenuated immunogenic compositions, attenuated vaccines (e.g., live attenuated vaccines) and/or attenuated vaccine vectors.

Enterobacteria are known in the art and are generally pathogens that can infect the gastrointestinal tract of avians and/or mammals. The present invention can be practiced with any suitable enterobacterium in the order Enterobacteriales and optionally in the family Enterobacteriaceae that encodes FNR, including but not limited to bacteria classified in the following genera: *Alishewanella, Alterococcus, Aquamonas, Aranicola, Arsenophonus, Azotivirga, Blochmannia, Brenneria, Buchnera, Budvicia, Buttiauxella, Candidatus, Cedecea, Citrobacter, Dickeya, Edwardsiella, Enterobacter, Erwinia* (e.g., *E. amylovora*), *Escherichia, Ewingella, Grimontella, Hafnia, Klebsiella* (e.g., *K. pneumoniae*), *Kuyvera, Leclercia, Leminorella, Moellerella, Morganella, Obesumbacterium, Pantoea, Pectobacterium, Candidatus Phlomobacter, Photohabdus, Plesiomonas* (e.g., *P. shigelloides*), *Pragia, Proteus* (e.g., *P. vulgaris*), *Providencia, Rahnella, Raoultella, Salmonella, Samsonia, Serratia* (e.g., *S. marcenscens*), *Shigella, Sodalis, Tatumella, Travulsiella, Wigglesworthia, Xenorhabdus, Yersinia* (e.g., *Y. pestis*), and *Yokenella*.

In particular embodiments, the enterobacterium is a *Salmonella* spp., an *Escherichia* spp., or a *Shigella* spp.

Further, the enterobacterium can optionally be a pathogenic enterobacterium. In particular embodiments, the enterobacterium from which the FNR deficient strain is derived is a pathogenic (e.g., virulent) bacterium as that term is understood in the art, where the attenuating fnr mutation results in a reduction in the pathogenicity. In representative embodiments, the FNR deficient strain is highly attenuated so as to be avirulent (e.g., induces no or insignificant levels of pathogenicity).

The term "pathogenic" is understood in the art, for example, as causing pathogenicity such as morbidity and/or mortality in a subject or population of subjects.

The term "attenuating" with respect to pathogenic microorganisms is understood in the art, for example, as a reduction in pathogenicity (including no detectable pathogenicity) produced in the subject as a result of administration of the FNR deficient enterobacterium strain as compared with the level of pathogenicity produced if an enterobacterium with a fully functional fnr gene (e.g., the wild-type strain) were administered.

Methods of assessing pathogenicity of enterobacteria, and attenuation thereof, are known in the art (e.g., morbidity and/or mortality following challenge in a suitable animal model such as mice or survival in cultured macrophages).

Suitable *Salmonella* species within the scope of the present invention include but are not limited to *S. bongori* and *S. enterica* as well as *S. enterica* subspecies (e.g., enterica, salamae, arizonae, diarizonae, houtenae and indica). Numerous serovars of *S. bongori* and *S. enterica* are known and are within the scope of the present invention. Exemplary *S. enterica* serovars include Typhimurium, Typhi and Enteritidis.

The present invention can further be practiced with any species of *Escherichia* including but not limited to *E. adecarboxylata, E. albertfi, E. blattae, E. coli* (including toxigenic strains such as *E. coli* O157:H7), *E. fergusonii, E. hermannii*, and *E. vulneris*.

Suitable species of *Shigella* include without limitation species in Serogroup A (e.g., *S. dysenteriae* and serotypes thereof), species in Serogroup B (e.g., *S. flexneri* and serotypes thereof), species in Serogroup C (e.g., *S. boydii* and serotypes thereof), and species in Serogroup D (e.g., *S. sonnei* and serotypes thereof).

The genomic sequences of numerous enterobacteria are known in the art. See, e.g., NCBI Accession No. NC_004337 (*Shigella flexneri* 2a str. 301); NCBI Accession No. NC_007613 (*Shigella boydii* Sb227); NCBI Accession No. AP009048 (*E. coli* W3110); NCBI Accession No. BA000007 (*E. coli* O157:H7 str. Sakai); NCBI Accession No. AE009952 (*Y. pestis* KIM); NCBI Accession No. NC_003197 (*S. typhimurium* LT2); and NCBI Accession No. NC_003198 (*S. enterica* subsp. *enterica* serovar Typhi str. CT18).

Likewise, the nucleic acid and amino acid sequences of the fnr gene from various enterobacteria are known in the art.

The attenuated enterobacteria of the present invention comprise an attenuating mutation in the fnr gene. In representative embodiments, the mutation is an attenuating deletion mutation (including truncations) that results in attenuation of the pathogenicity of the bacterium. Other mutations include without limitation attenuating insertions, substitutions and/or frame-shift mutations that result in attenuation of the pathogenicity of the bacterium. In embodiments of the invention, the mutation is a non-polar alteration in the fnr gene.

Deletion and insertion mutations can be any deletion/insertion mutation in the fnr gene that results in attenuation of the pathogenicity of the bacterium. In representative embodiments, the alteration is a deletion or an insertion of at least about 9, 30, 50, 75, 90, 120, 150, 180, 240, 300, 450 or more consecutive nucleotides in the fnr gene that results in attenuation of the pathogenicity of the bacterium. Optionally, essentially all (e.g., at least about 95%, 97%, 98% or more) or all of the fnr coding sequence is deleted. In other embodiments, essentially all or all of the fnr gene, including regulatory elements, is deleted. In particular embodiments, the deletion can extend beyond the fnr gene. Generally, however, the deletion does not render genes essential for growth, multiplication and/or survival non-functional. In particular embodiments, the deletion does not extend into any genes essential for growth, multiplication and/or survival. In embodiments of the invention, the deletion does not extend to genes that are 5' and/or 3' of the fnr coding region or the fnr gene.

One FNR deficient strain of *S. enterica* serovar Typhimurium has been constructed by the inventors and is shown in the Examples.

The FNR deficient enterobacterium strains of the invention can further comprise other mutations, including other attenuating mutations.

Generally, the FNR deficient enterobacterium strains will retain other appropriate genomic sequences to be able to grow, multiply and survive (e.g., in the gut of a host). Thus, the fnr mutations of the invention exclude lethal mutations that unduly inhibit the survival of the organism.

In embodiments of the invention, the FNR mutation results in at least about a 25%, 40%, 50%, 60%, 70%, 80%, 85%, 90%, 95%, 97%, 98% or more reduction in FNR mRNA, protein and/or activity. Methods of assessing levels of mRNA and proteins levels and FNR activity are known in the art.

The fnr mutation can be combined with any other mutation known in the art, including other attenuating mutations. For example, the fnr mutant enterobacterium can also comprise an arcA mutation. The ArcA protein cooperates with FNR for controlling the transitions from aerobic/anaerobic conditions and vice versa.

The attenuated enterobacteria of the present invention can be used as an attenuated immunogenic compositions or attenuated vaccine against enterobacteria (e.g., a live attenuated vaccine). Enterobacteria are described above. In embodiments of the invention, the enterobacterium is a pathogenic enterobacterium. For example, in particular embodiments, the invention provides live immunogenic compositions or live attenuated vaccines against *Salmonella*, *Shigella* or *Escherichia*. The attenuated enterobacterium vaccine can be used to induce an immune response against one species or against multiple closely related species/genera of enterobacteria (e.g., that cross-react with antibodies produced in response to administration of the attenuated enterobacterium).

Further, the attenuated FNR deficient enterobacterium strains of the invention can be used as vectors, e.g., to deliver an antigen(s) that is heterologous (e.g., foreign) to the enterobacterium vector (including any plasmids carried by the enterobacterium) to induce an immune response against other organisms (e.g., pathogenic organisms). In one embodiment, a heterologous nucleic acid sequence encoding the foreign antigen(s) is incorporated into the genomic DNA of the enterobacterium (e.g., inserted into or in place of a deleted fnr gene). In other embodiments, the heterologous nucleic acid sequence encoding the foreign antigen is incorporated into a plasmid that is carried by an attenuated FNR deficient host (e.g., a Δfnr host). Plasmids that are compatible with the various enterobacteria are known in the art.

The attenuated FNR deficient strains can further be used as vectors to deliver therapeutic proteins and untranslated RNAs (e.g., siRNA, shRNA, antisense RNA).

Methods of expressing foreign antigens in enterobacteria are known to those skilled in the art. For example, the foreign antigen can be expressed as part of a fusion with one of the structural proteins of the bacterial host (e.g., expressed on the surface of the bacterium) such as a flagellin protein (see, e.g., Chauhan et al., (2005) *Molecular and Cellular Biochemistry* 276:1-6) or a membrane protein as known in the art. See also, Chinchilla et al., (2007) *Infection Immun.* 75: 3769. In other embodiments, the foreign antigen is not expressed as a fusion with a host structural protein. According to this embodiment, the heterologous nucleic acid encoding the foreign antigen can optionally be operably associated with a leader sequence directing secretion of the foreign antigen from the bacterial cell.

The heterologous nucleic acid sequence encoding the foreign antigen can be operatively associated with any suitable promoter or other regulatory sequence. The promoter or regulatory sequence can be native or foreign to the host, can be native or foreign to the heterologous nucleic acid, and can further be partially or completely synthetic.

The codon usage of the heterologous nucleic acid sequence can be optimized for expression in the enterobacterium using methods known to those skilled in the art (see, e.g., Chinchilla et al., (2007) *Infection Immun.* 75: 3769.

The foreign antigen can be any suitable antigen known in the art, and can further be from a bacterial, yeast, fungal, protozoan or viral source. Suitable antigens include, but are not limited to antigens from pathogenic infectious agents.

The antigen can be an antigen from a pathogenic microorganism, which includes but is not limited to, *Rickettsia, Chlamydia, Mycobacteria, Clostridia, Corynebacteria, Mycoplasma, Ureaplasma, Legionella, Shigella, Salmonella*, pathogenic *Escherichia coli* species, *Bordatella, Neisseria, Treponema, Bacillus, Haemophilus, Moraxella, Vibrio, Staphylococcus* spp., *Streptococcus* spp., *Campylobacter* spp., *Borrelia* spp., *Leptospira* spp., *Erlichia* spp., *Klebsiella* spp., *Pseudomonas* spp., *Helicobacter* spp., and any other pathogenic microorganism now known or later identified (see, e.g., Microbiology, Davis et al, Eds., 4th ed., Lippincott, New York, 1990, the entire contents of which are incorporated herein by reference for the teachings of pathogenic microorganisms).

Specific examples of microorganisms from which the antigen can be obtained include, but are not limited to, *Helicobacter pylori, Chlamydia pneumoniae, Chlamydia trachomatis, Ureaplasma urealyticum, Mycoplasma pneumoniae, Staphylococcus aureus, Streptococcus pyogenes, Streptococcus pneumoniae, Streptococcus viridans, Enterococcus faecalis, Neisseria meningitidis, Neisseria gonorrhoeae, Treponema pallidum, Bacillus anthracis, Salmonella typhi, Vibrio cholera, Pasteurella pestis, Pseudomonas aeruginosa, Campylobacter jejuni, Clostridium difficile, Clostridium tetani, Clostridium botulinum, Mycobacterium tuberculosis, Borrelia burgdorferi, Haemophilus ducreyi, Corynebacterium diphtheria, Bordetella pertussis, Bordetella parapertussis, Bordetella bronchiseptica, Haemophilus influenza*, and enterotoxic *Escherichia coli*.

The antigen can further be an antigen from a pathogenic protozoa, including, but not limited to, *Plasmodium* spp.

(e.g., malaria antigens), *Babeosis* spp., *Schistosoma* spp., *Trypanosoma* spp., *Pneumocystis* carnii, *Toxoplasma* spp., *Leishmania* spp., and any other protozoan pathogen now known or later identified.

The antigen can also be an antigen from pathogenic yeast and fungi, including, but not limited to, *Aspergillus* spp., *Candida* spp., *Cryptococcus* spp., *Histoplasma* spp., *Coccidioides* spp., and any other pathogenic fungus now known or later identified.

Suitable antigens can include, but are not limited to, viral antigens such as antigens including but not limited to human hepatitis C virus (HCV) antigens and influenza antigens.

Other specific examples of various antigens include, but are not limited to, the B1 protein of hepatitis C virus (Bruna-Romero et al. (1997) *Hepatology* 25: 470-477), amino acids 252-260 of the circumsporozoite protein of *Plasmodium berghei* [Allsopp et al. (1996) *Eur. J. Immunol.* 26: 1951-1958], the influenza A virus nucleoprotein [e.g., residues 366-374; Nomura et al. (1996) *J. Immunol. Methods* 193: 4149], the listeriolysin 0 protein of *Listeria monocytogenes* [residues 91-99; An et al. (1996) *Infect. Immun.* 64: 1685-1693], *P. falciparum* antigens (causing malaria, e.g., tCSP), hepatitis B surface antigen [Gilbert et al. (1997) *Nature Biotech.* 15: 1280-1283], and *E. coli* O157.H1.

The term "antigen" as used herein includes toxins such as the neurotoxin tetanospasmin produced by *Clostridium tetani* and the toxin produced by *E. coli* O157:H7.

In particular embodiments, the attenuated enterobacteria of the invention express a foreign antigen(s) and can be used to induce an immune response against both the enterobacterium and the organism(s) from which the foreign antigen(s) is derived and, optionally, other species/genera closely related to either of the foregoing (e.g., that cross-react with antibodies produced in response to administration of the attenuated enterobacterium).

There is no particular size limitation to the heterologous nucleic acid encoding the foreign antigen. When incorporated into the genomic DNA, the heterologous nucleic acid will generally be at least about 30, 50, 75, 100, 150 or 200 nucleotides in length and/or less than about 1, 1.5, 2, 2.5 or 3 kilobases in length. When carried by a plasmid, the heterologous nucleic acid can generally be longer, e.g., at least about 30, 50, 75, 100, 150, 200, 500 or 1000 nucleotides in length and/or less than about 5, 10, 12, 14, 16, 18 or 20 kilobases in length.

In representative embodiments, the FNR deficient enterobacterium is a Δfnr mutant, which advantageously reduces the probability of reversion to the wild-type pathogenic phenotype. For example, most current live attenuated vaccine strains against typhoid are auxotrophs for some nutrients, which are likely less stable than the deletion mutants.

The present invention can be used for therapeutic/prophylactic and non-therapeutic/prophylactic purposes. For example, the present invention provides FNR deficient (e.g., Δfnr) enterobacteria strains that can be used to study the fnr gene, its role in virulence in these organisms, and as attenuated immunogenic compositions, attenuated vaccines (e.g., live attenuated vaccines) and attenuated vaccine vectors (e.g., live attenuated vaccine vectors).

With respect to uses as an attenuated vaccine or vaccine vector, the present invention finds use in both veterinary and medical applications. Suitable subjects include avians, mammals and fish, with mammals being preferred. The term "avian" as used herein includes, but is not limited to, chickens, ducks, geese, quail, turkeys and pheasants. The term "mammal" as used herein includes, but is not limited to, primates (e.g., simians and humans), bovines, ovines, caprines, porcines, equines, felines, canines, lagomorphs, rodents (e.g., rats and mice), etc. Human subjects include fetal, neonatal, infant, juvenile and adult subjects.

The invention can be used in a therapeutic and/or prophylactic manner. For example, in one embodiment, to protect against an infectious disease, subjects may be vaccinated prior to exposure, e.g., as neonates or adolescents. Adults that have not previously been exposed to the disease may also be vaccinated.

In particular embodiments, the present invention provides a pharmaceutical composition comprising a FNR deficient (e.g., Δfnr) strain enterobacterium (optionally, a live FNR deficient enterobacterium) in a pharmaceutically-acceptable carrier, which can also include other medicinal agents, pharmaceutical agents, carriers, adjuvants, diluents, etc. For injection, the carrier is typically a liquid. For other methods of administration, the carrier may be either solid or liquid, such as sterile, pyrogen-free water or sterile pyrogen-free phosphate-buffered saline solution. For inhalation administration, the carrier will be respirable, and is optionally in solid or liquid particulate form. Formulation of pharmaceutical compositions is well known in the pharmaceutical arts [see, e.g., Remington's Pharmaceutical Sciences, 15th Edition, Mack Publishing Company, Easton, Pa. (1975)].

By "pharmaceutically acceptable" it is meant a material that is not biologically or otherwise undesirable, e.g., the material may be administered to a subject without causing undesirable biological effects.

The FNR deficient strains of the invention can be administered to elicit an immune response. Typically, immunological compositions of the present invention comprise an immunogenically effective amount of the FNR deficient strain enterobacterium as disclosed herein, optionally in combination with a pharmaceutically acceptable carrier.

An "immunogenically effective amount" is an amount that is sufficient to induce an immune response in the subject to which the composition is administered. Nonlimiting examples of dosages include about $10^4$ to $10^9$ colony forming units (cfu), about $10^5$ to $10^8$ cfu or about $10^6$ to $10^7$ cfu. Optionally, one or more booster dosages (e.g., about $10^3$ to $10^8$ cfu or $10^4$ to $10^5$ cfu) can be administered.

The invention also encompasses methods of producing an immune response in a subject, the method comprising: administering a FNR deficient (e.g., Δfnr) enterobacterium strain of the invention or a pharmaceutical formulation containing the same to a subject in an immunogenically effective amount so that an immune response is produced in the subject.

The terms "vaccination" or "immunization" are well-understood in the art. For example, the terms vaccination or immunization can be understood to be a process that increases a subject's immune reaction to antigen and thereby enhance the ability to resist and/or overcome infection.

Any suitable method of producing an immune response (e.g., immunization) known in the art can be employed in carrying out the present invention, as long as an active immune response (preferably, a protective immune response) is elicited.

In representative embodiments, less pathogenicity (including no detectable pathogenicity) is produced in the subject as a result of administration of the FNR deficient enterobacterium strain as compared with pathogenicity produced if an enterobacterium with a fully functional fnr gene (e.g., the wild-type strain) were administered (e.g., at least about a 25%, 40%, 50%, 60%, 70%, 80%, 85%, 90%, 95%, 97%, 98% or more reduction in pathogenicity).

Vaccines can be given as a single dose schedule or in a multiple dose schedule. A multiple dose schedule is one in which a primary course of administration may consist of about 1 to 10 separate doses, followed by other doses (i.e., booster doses) given at subsequent time intervals to maintain and/or reinforce the immune response, for example, at about 1 to 4 months for a second dose, and if needed, a subsequent dose(s) after another several months or year. The dosage regimen will also, at least in part, be determined by the need of the individual and be dependent upon the judgment of the medical or veterinary practitioner.

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogen by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease, the progression of the disease and/or the symptoms of the disease. Alternatively, a protective immune response or protective immunity may be useful in the treatment of disease including infectious disease. The protective effects may be complete or partial, as long as the benefits of the treatment outweigh any disadvantages thereof.

Administration of the attenuated enterobacteria and compositions of the invention can be by any means known in the art, including oral, rectal, topical, buccal (e.g., sub-lingual), vaginal, intra-ocular, parenteral (e.g., subcutaneous, intramuscular including skeletal muscle, cardiac muscle, diaphragm muscle and smooth muscle, intradermal, intravenous, intraperitoneal), topical (e.g., mucosal surfaces including airway surfaces), intranasal, transmucosal, intratracheal, transdermal, intraventricular, intraarticular, intrathecal and inhalation administration.

The most suitable route in any given case will depend on the nature and severity of the condition being treated, the FNR deficient strain enterobacterium, and the composition being administered.

The FNR deficient enterobacterium strain can be formulated for administration in a pharmaceutical carrier in accordance with known techniques. See, e.g., Remington, *The Science and Practice of Pharmacy* ($9^{th}$ Ed. 1995). In the manufacture of a pharmaceutical formulation according to the invention, the FNR deficient enterobacterium strain is typically admixed with, inter alia, an acceptable carrier. The carrier can be a solid or a liquid, or both, and is optionally formulated as a unit-dose formulation, which can be prepared by any of the well-known techniques of pharmacy.

For injection, the carrier is typically a liquid, such as sterile pyrogen-free water, pyrogen-free phosphate-buffered saline solution, bacteriostatic water, or Cremophor EL[R] (BASF, Parsippany, N.J.). For other methods of administration, the carrier can be either solid or liquid.

For oral administration, the FNR deficient enterobacterium strain can be administered in solid dosage forms, such as capsules, tablets, and powders, or in liquid dosage forms, such as elixirs, syrups, and suspensions. The FNR deficient strain enterobacterium can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges comprising the FNR deficient enterobacterium strain in a flavored base, usually sucrose and acacia or tragacanth; and pastilles comprising the FNR deficient enterobacterium strain in an inert base such as gelatin and glycerin or sucrose and acacia.

Formulations of the present invention suitable for parenteral administration can comprise sterile aqueous and non-aqueous injection solutions of the FNR deficient enterobacterium strain, which preparations are generally isotonic with the blood of the intended recipient. These preparations can contain anti-oxidants, buffers, bacteriostats and solutes, which render the formulation isotonic with the blood of the intended recipient. Aqueous and non-aqueous sterile suspensions can include suspending agents and thickening agents. The formulations can be presented in unit\dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets. For example, in one aspect of the present invention, there is provided an injectable, stable, sterile composition comprising a FNR deficient enterobacterium strain of the invention, in a unit dosage form in a sealed container. Optionally, the composition is provided in the form of a lyophilizate, which is capable of being reconstituted with a suitable pharmaceutically acceptable carrier to form a liquid composition suitable for injection thereof into a subject.

Formulations suitable for rectal or vaginal administration can be presented as suppositories. These can be prepared by admixing the FNR deficient enterobacterium strain with one or more conventional excipients or carriers, for example, cocoa butter, polyethylene glycol or a suppository wax, which are solid at room temperature, but liquid at body temperature and therefore melt in the rectum or vaginal cavity and release the FNR deficient FNR deficient enterobacterium strain.

Formulations suitable for topical application to the skin can take the form of an ointment, cream, lotion, paste, gel, spray, aerosol, or oil. Carriers that can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis [see, for example, *Pharmaceutical Research* 3 (6):318 (1986)] and typically take the form of an optionally buffered aqueous solution. Suitable formulations comprise citrate or bis\tris buffer (pH 6) or ethanol/water.

The FNR deficient enterobacterium strain can be formulated for nasal administration or otherwise administered to the lungs of a subject by any suitable means, for example, by an aerosol suspension of respirable particles comprising the FNR deficient enterobacterium strain, which the subject inhales. The respirable particles can be liquid or solid. The term "aerosol" includes any gas-borne suspended phase, which is capable of being inhaled into the bronchioles or nasal passages. Specifically, an aerosol includes a gas-borne suspension of droplets, as can be produced in a metered dose inhaler or nebulizer, or in a mist sprayer. An aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al. (1992) *J. Pharmacol. Toxicol. Methods* 27:143-159. Aerosols of liquid particles can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the FNR deficient enterobacterium strain can likewise be produced with any solid particulate medicament aerosol generator, by techniques known in the pharmaceutical art.

In particular embodiments of the invention, administration is by subcutaneous or intradermal administration. Subcutaneous and intradermal administration can be by any method known in the art, including but not limited to injection, gene gun, powderject device, bioject device, microenhancer array, microneedles, and scarification (i.e., abrading the surface and then applying a solution comprising the FNR deficient enterobacterium strain).

In other embodiments, the FNR deficient enterobacterium strain is administered intramuscularly, for example, by intramuscular injection.

The examples which follow are set forth to illustrate the present invention, and are not to be construed as limiting thereof.

EXAMPLE 1

Materials and Methods

Bacterial strains. Wild-type (WT) serovar Typhimurium (ATCC 14028s) and its isogenic fnr mutant (NC 983) were used throughout the studies described herein. The mutant strain was constructed by transducing the fnr.:Tn10 mutation from serovar Typhimurium [SL2986/TN 2958 (fnr.:Tn 10)] to strain 14028s using P22 phage (all from the culture collection of S. Libby). The transductants were plated on Evans blueuranine agar, and the tetracycline marker was eliminated (Bochner et al., 1980) *J. Bacteriol.* 143:926-933). The $Tet^s$ and $FNR^-$ phenotypes were confirmed by the inability of NC983 (fnr mutant) to grow on media containing tetracycline (10 µg/ml) and by its inability to grow anaerobically on M9 minimal medium containing glycerol plus nitrate, respectively. Sequence analysis of fnr and neighboring genes (i.e., ogt and ydaA, respectively) in NC 893 showed that the remnant of Tn10 (tnpA) interrupts fnr between by 106 and 107 and has no polar effect on ogt or ydaA (FIG. 1).

For complementation studies, a low-copy-number plasmid expressing fnr (pfnr) was constructed. The complete fnr sequence starting from the stop codon of ogtA (TGA [indicated in boldface type]) to 21 by downstream of fnr (i.e., a 972 by fragment) was amplified from WT strain 14028s with the following primers: fnr-Forward, 5'-ATAT CCATGGTGAATATACAGGAAAAAGTGC-3' (an NcoI site is underlined; SEQ ID NO:1); fnr-Reverse, 5'-ATATATT CAGCTGCATCAATGGTTTAGCTGACG-3' (a PvuII site is underlined; SEQ ID NO:2). The PCR product was digested with NcoI and PvuII and ligated into the low-copy-number vector pACYC184 cut with NcoI and PvuII. Thus, in the new plasmid (pfnr) the Cmr gene in pACYC184 is replaced with the fnr gene. The plasmid (pfnr) was electroporated and maintained in *E. coli* DH5α. Transformants were confirmed for $Tet^r$ (15 µg/ml) and Cms (20 µg/ml) on Luria-Bertani (LB) plates, and the presence of the fnr gene was confirmed by restriction analysis using EcoRI and HindIII. The plasmid isolated from DH5α was used to complement the fnr mutant. Transformants were selected on LB plates containing tetracycline (15 µg/ml).

Growth conditions. The WT and the fnr mutant were grown anaerobically at 37° C. in MOPS (morpholinepropanesulfonic acid)-buffered (100 mM, pH 7.4) LB broth supplemented with 20 mM D-xylose (LB-MOPS-X). This medium was used in order to avoid the indirect effects of pH and catabolite repression. A Coy anaerobic chamber (Coy, Ann Arbor, Mich.) and anaerobic gas mixture (10% H2, 5% $CO_2$, and 85% $N_2$) were used. All solutions were preequilibrated for 48 h in the chamber. Cells from frozen stocks were used to inoculate LB-MOPS-X broth. Cultures were grown for 16 h and used to inoculate fresh anoxic media. The anaerobic growth kinetics of the mutant and the WT strains were similar, and the doubling times of the fnr mutant and the WT were 53.9±1.2 and 45.4±2.9 min, respectively.

RNA isolation. Anaerobic cultures were used to inoculate three independent flasks each containing 150 ml of anoxic LB-MOPS-X. The three independent cultures were grown to an optical density at 600 nm (OD600) of 0.25 to 0.35, pooled, and treated with RNAlater (QIAGEN, Valencia, Calif.) to fix the cells and preserve the quality of the RNA. Total RNA was extracted with the Rneasy RNA extraction kit (QIAGEN), and the samples were treated with RNase-free DNase (Invitrogen, Carlsbad, Calif.). The absence of contaminating DNA and the quality of the RNA was confirmed by PCR amplification of known genes and by using agarose gel electrophoresis. Aliquots of the RNA samples were kept at −80° C. for use in the microarray and quantitative real-time reverse transcription-PCR (qRT-PCR) studies.

Microarray studies. Serovar Typhimurium microarray slides were prepared and used as previously described in Porwollik, S. et al., "The delta uvrB mutations in the Ames strains of *Salmonella* span 15-119 gene" *Mutat. Res.* 483:1-11 (2001). The SuperScript Indirect cDNA labeling system (Invitrogen) was used to synthesize the cDNA for the hybridizations. Each experiment consisted of two hybridizations, on two slides, and was carried out in Corning Hybridization Chambers at 42° C. overnight. Dye swapping was performed to avoid dye-associated effects on cDNA synthesis. The slides were washed at increasing stringencies (2×SSC [1×SSC is 0.15 M NaCl plus 0.015 M sodium citrate], 0.1% sodium dodecyl sulfate [SDS], 42° C.; 0.1% SSC, 0.1% SDS, room temperature; 0.1% SSC, room temperature). Following hybridization, the microarrays were scanned for the Cy3 and Cy5 fluorescent signals with a ScanArray 4000 microarray scanner from GSI Lumonics (Watertown, Mass.). The intensity of every spot was codified as the sum of the intensities of all the pixels within a circle positioned over the spot itself and the background as the sum of the intensities of an identical number of pixels in the immediate surroundings of the circled spot.

Data analysis. Cy3 and Cy5 values for each spot were normalized over the total intensity for each dye to account for differences in total intensity between the two scanned images. The consistency of the data obtained from the microarray analysis was evaluated by two methods: (i) a pair-wise comparison, calculated with a two-tailed Student's t test and analyzed by the MEAN and TTEST procedures of SAS-STAT statistical software (SAS Institute, Cary, N.C.) (the effective degrees of freedom for the t test were calculated as described previously in Satterthwaite, F. E. "An approximate distribution of estimates of variance components" *Biometrics Bull.* 2:110-114 (1946)); and (ii) a regularized t test followed by a posterior probability of differential expression [PPDE (p)] method. These statistical analyses are implemented in the Cyber-T software package available online at the website of the Institute for Genomics and Bioinformatics of the University of California, Irvine. The signal intensity at each spot from the FNR mutant and the WT were background subtracted, normalized, and used to calculate the ratio of gene expression between the two strains. All replicas were combined, and the median expression ratios and standard deviations were calculated for open reading frames (ORFs) showing $\geq 2.5$-fold change.

qRT-PCR. qRT-PCR was used to validate the microarray data, where 19 genes were randomly chosen from the differentially expressed genes. This technique was also used to confirm the expression of a set of selected genes. qRT-PCRs were carried out with the QuantiTect SYBR green RT-PCR kit (QIAGEN) and an iCycler (Bio-Rad, Hercules, Calif.), and the data were analyzed by the Bio-Rad Optical System software, version 3.1, according to manufacturer specifications. To ensure accurate quantification of the mRNA levels, three amplifications for each gene were made with 1:5:25 dilutions of the total RNA. Measured mRNA levels were normalized to the mRNA levels of the housekeeping gene rpoD ($\sigma$70). Normalized values were used to calculate the ratios of the expression levels in the fnr mutant relative to the WT.

Logo graph and promoter analysis. The information matrix for the generation of the FNR logo was produced by using the alignment of the *E. coli* FNR binding sequences, available at http://arep.med.harvard.edu/ecoli_matrices/. The alignment of the FNR motifs from this website did not include the motifs present in the sodA and mutts promoters; therefore, they were included in our analysis. To account for differences in nucleotide usage or slight variations in consensus sequences, a second alignment was built for serovar Typhimurium using the 5' regions of the homologous genes originally used to build the *E. coli* information matrix. The alignment was used to prepare a new information matrix using the Patser software (version 3d), available at http://rsatub.ac.be/rsat/. A graphical representation (FIG. 2) of the matrices through a logo graph was obtained with Weblogo software (version 2.8.1, 18 Oct. 2004), available at http://weblogo.berkeley.ed u/.

Motility assay and electron microscopy. The motilities of the WT, the fnr mutant, and the complemented mutant/pfnr were evaluated under anoxic conditions. Ten microliters of anaerobically grown (16 h) cells were spotted onto LB-MOPS-X agar (0.6% agar) plates and incubated at 37° C. for 24 h. The diameter of the growth halo was used as a measure of motility. Scanning electron microscopy (SEM) was used to examine the morphology of the extracellular surfaces. WT and fnr cultures were grown anaerobically (OD600, 0.3 to 0.4) and centrifuged, and the pellets were resuspended in a fixative solution (3% glutaraldehyde in 0.1 M phosphate-buffered saline [PBS] [pH 7.4]) under anaerobic conditions. The fixed samples were rinsed in 0.1 M PBS buffer, postfixed with 1% osmium tetroxide in 0.1 M PBS for 2 h, and rinsed with PBS, all at 4° C. An aliquot of each sample was filtered through a 0.1-µm filter. Each filter was dehydrated through a graded ethanol series (up to 100%), brought to room temperature, critical point dried with liquid $CO_2$ (Tousimis Research, Rockville, Md.), placed on stubs, and sputter coated with Au/Pd (Anatech Ltd., Denver, N.C.). Samples were viewed at 15 kV with a JEOL 5900LV SEM (JEOL USA, Peabody, Mass.). Transmission electron microscopy (TEM) and negative staining were used to visualize the flagella. WT and fnr cultures were grown anaerobically (OD600, 0.3 to 0.4), and a 20-µl aliquot of each sample was separately placed on a Formvar-carbon grid. The grids were washed with 0.1 M sodium acetate (pH 6.6), negatively stained with 2% phosphotungstic acid (PTA), and air dried for 5 min before being viewed at 80 kV with a JEOL JEM-100S TEM (JEOL USA, Peabody, Mass.).

Pathogenicity assays. Immunocompetent 6- to 8-week-old C57BL/6 mice and their congenic iNOS-/- and pg91phox$^{-/-}$ immunodeficient mice (bred in the University of Colorado Health Science Center [UCHSC] animal facility according to Institutional Animal Care and Use Committee guidelines) were used in this study. Stationary-phase serovar Typhimurium (WT and fnr mutant) cultures grown aerobically in LB-MOPS-X broth were used, and the cells were diluted in PBS. For oral (p.o.) challenge, groups of 10 mice were gavaged with $5 \times 10^6$ or $5 \times 10^7$ CFU in 200 µl of PBS/mouse. For intraperitoneal (i.p.) challenge, groups of five mice were inoculated with 250 CFU in 500 µl of PBS/mouse. Mortality was scored over a 15- to 30-day period.

Macrophage assay. Peritoneal macrophages were harvested from C57BL/6 mice and pg91phox$^{-/-}$ immunodeficient mice (bred in the UCHSC animal facility) 4 days after intraperitoneal inoculation with 1 mg/ml sodium periodate and used as previously described in DeGroote, M. A. et al. "Periplasmic superoxide dismutase protects *Salmonella* from products of phagocyte NADPH-oxidase and nitric oxide synthase" *Proc. Natl. Acad. Sci.* 94:13997-14001 (1997). Macrophages were challenged (multiplicity of infection of 2) for 25 min with the different test strains. Stationary-phase cultures grown aerobically in LB-MOPS-X broth were used as outlined above. Prior to infection, each strain was opsonized with 10% normal mouse serum for 20 min. After the challenge, extracellular bacteria were removed from the monolayers by washing with prewarmed RPMI medium (Cellgro, Herndon, Va.) containing gentamicin (6 mg/ml) (Sigma), the *Salmonella*-infected macrophages were lysed at indicated time points, and the surviving bacteria were enumerated on LB agar plates. The results are expressed as percent survival relative to the number of viable intracellular bacteria recovered at time zero (i.e., after washing and removal of the extracellular bacteria, 25 min after infection).

Microarray data. The microarray data are accessible via GEO accession number GSE3657 at http://www.ncbi.nlm.nih.gov/geo (the disclosure of which is incorporated herein by reference in its entirety).

EXAMPLE 2

Transcriptome Profiling

Out of 4,579 genes, the two-tailed Student t test produced a set of 1,664 coding sequences showing significant differences (P<0.05) between the fnr mutant and the WT. The analysis was restricted to include highly affected genes (i.e., having a ratio of ≧2.5-fold). Under this constraint, 311 genes were differentially expressed in the fnr mutant relative to the WT; of these, 189 genes were up-regulated and 122 genes were down-regulated by FNR (Table 3). The 311 FNR-regulated genes were classified into clusters of orthologous groups (COGs) as defined at http://www.ncbi.nlm.nih.gov/COG. Throughout the study levels of transcription in the fnr mutant were compared to that in the WT strain. Thus, genes repressed by FNR possess values of >1, while genes activated by FNR have values of <1.

Figure 3:
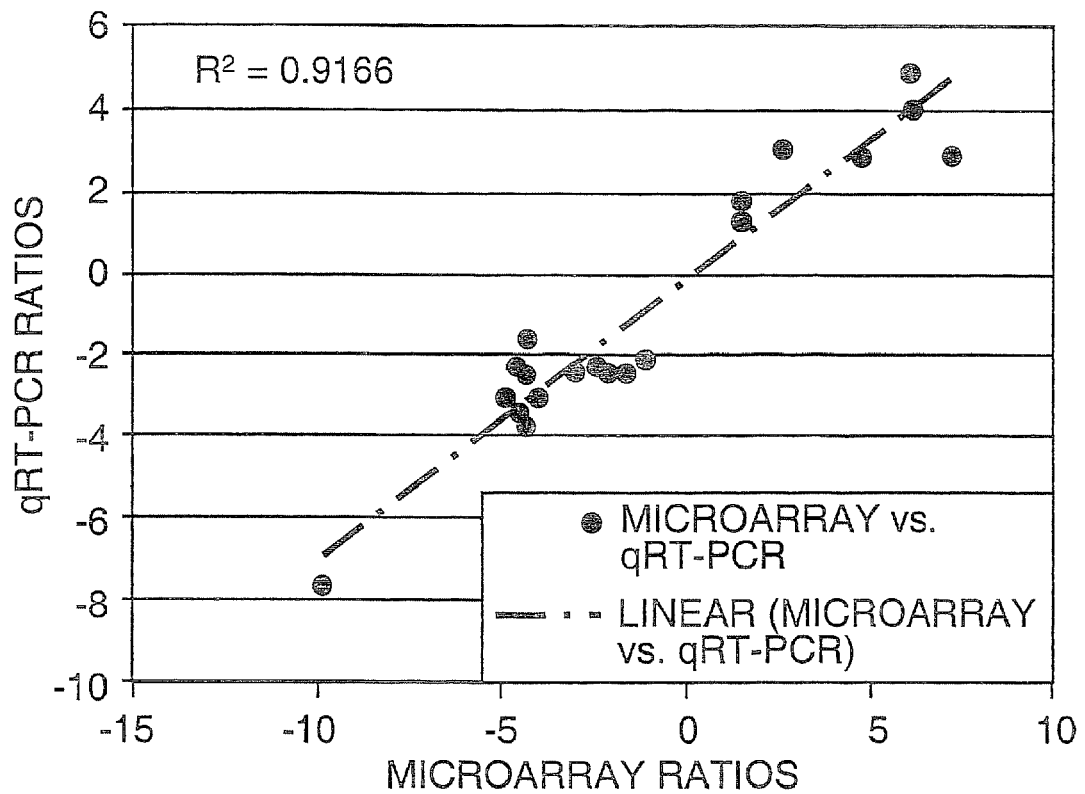
FIG. 3 shows the correlation between the microarray and qRT-PCR data for 19 selected genes. The ratios of changes in gene expression, from the microarray and qRT-PCR experiments, for the FNR mutant relative to the WT were $\log_2$ transformed and linearly correlated.

In order to globally validate the microarray data, 19 of the 311 differentially expressed genes for qRT-PCR were selected. The measured levels of mRNA were normalized to the mRNA levels of the housekeeping gene rpoD. The specific priers used for qRT-PCR and the normalized mRNA levels are shown in Table 1. The microarray and qRT-PCR data were $\log_2$ transformed and plotted (FIG. 3). The correlation between the two sets of data was 0.94 (P<0.05).

Figure 2:
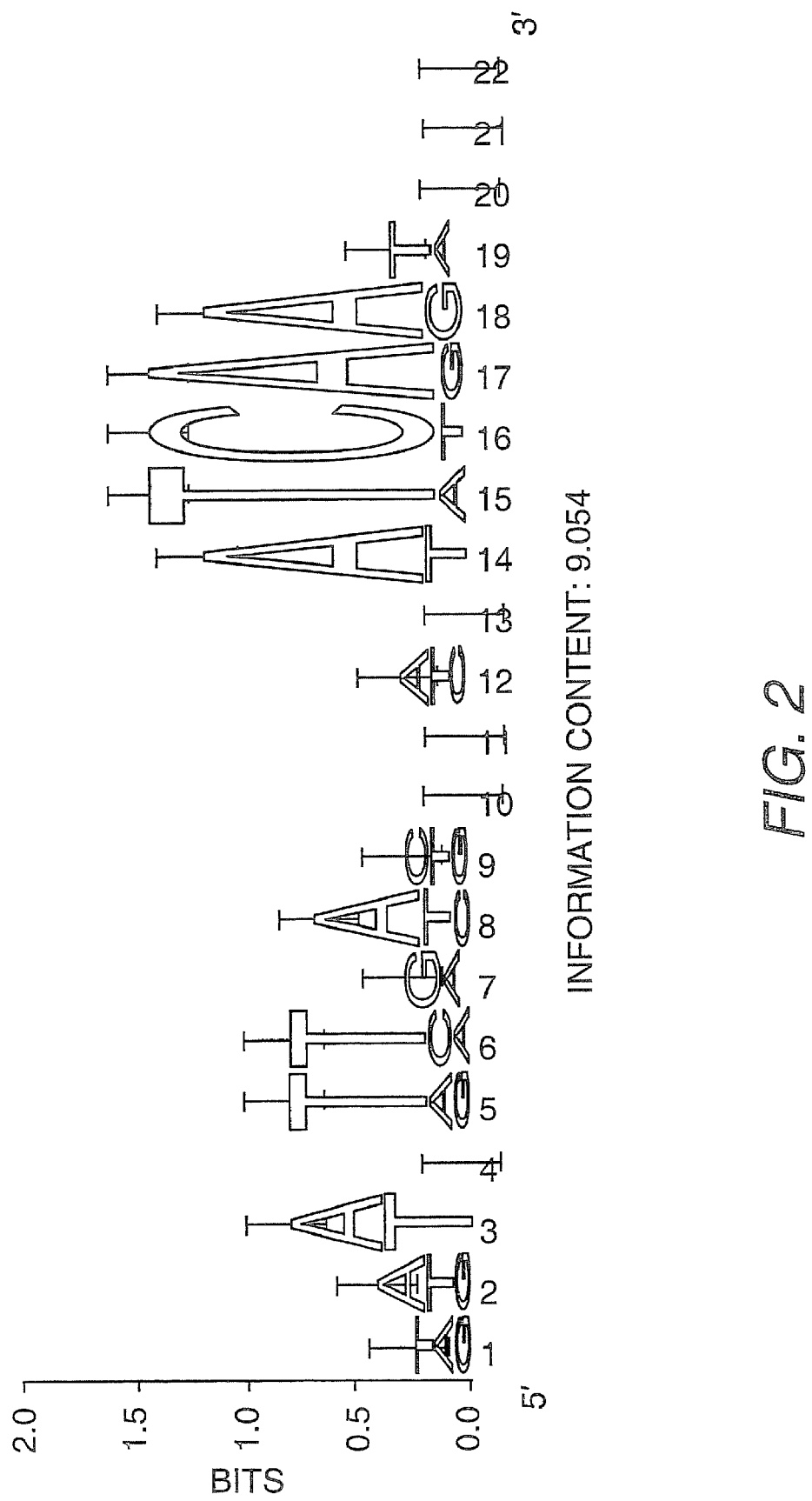
FIG. 2 shows a logo graph of the information matrix obtained from the consensus alignment of FNR motif sequences for serovar Typhimurium (derived from the corresponding FNR-regulated genes in *E. coli*). The total height of each column of characters represents the amount of information for that specific position, and the height of each character represents the frequency of each nucleotide.

To determine whether a binding site for FNR might be present in the region upstream of the candidate FNR-regulated genes, 5' regions of these genes were searched for the presence of a putative FNR-binding motif using a *Salmonella* logo graph (FIG. 2). One hundred ten out of the 189 genes activated by FNR (58%) and 59 out of the 122 genes repressed by FNR (48%) contained at least one putative FNR-binding site.

EXAMPLE 3

FNR as a Repressor

Transcription of the genes required for aerobic metabolism, energy generation, and nitric oxide detoxification was repressed by FNR. In particular, the genes coding for cytochrome c oxidase (cyoABCDE), cytochrome cd complex (cydAB), NADH-dehydrogenase (nuoBCEFJLN), succinyl-coenzyme A (CoA) metabolism (sucBCD), fumarases (fumB, stm0761, and stm0762), and the NO.-detoxifying flavohemoglobin (hmpA) were expressed at higher levels in the fnr mutant than in the WT (Table 3). Also, genes required for L-Iactate metabolism (lld-PRD) and for the production of phosphoenolpyruvate (pykF), oxaloacetate (ppc), and acetoacetyl-CoA (yqeF) were expressed at higher levels in the mutant than in the WT (Table 3).

EXAMPLE 4

FNR as an Activator

Several genes associated with anaerobic metabolism, flagellar biosynthesis, motility, chemotaxis, and *Salmonella* pathogenesis were activated by FNR. The genes constituting the dms operon, dmsABC (encoding the anaerobic dimethyl sulfoxide reductase), required for the use of dimethyl sulfoxide (DMSO) as an anaerobic electron acceptor, had the lowest expression levels (i.e., −200-, −62-, and −23-fold, respectively) in the fnr mutant relative to the WT (Table 3). Two other operons coding for putative anaerobic DMSO reductases (STM4305 to STM4307 and STM2528 to STM2530) were also under positive control by FNR. The genes required for the conversion of pyruvate to phosphoenolpyruvate (pps), Ac-CoA (aceF), Ac-P (pta), and OAc (ackA), as well as those for the production of formate (tdcE, yfiD, focA) and D-lactate (ldhA), were expressed at lower levels in the fnr mutant than in the WT. In addition, the genes coding for a universal stress protein (ynaF), a ferritinlike protein (ftnB), an ATP-dependent helicase (hrpA), and aerotaxis/redox sensing (aer) were also positively regulated by FNR (Table 3).

Figures 4A, 4B, 4C, 4D, 4E:
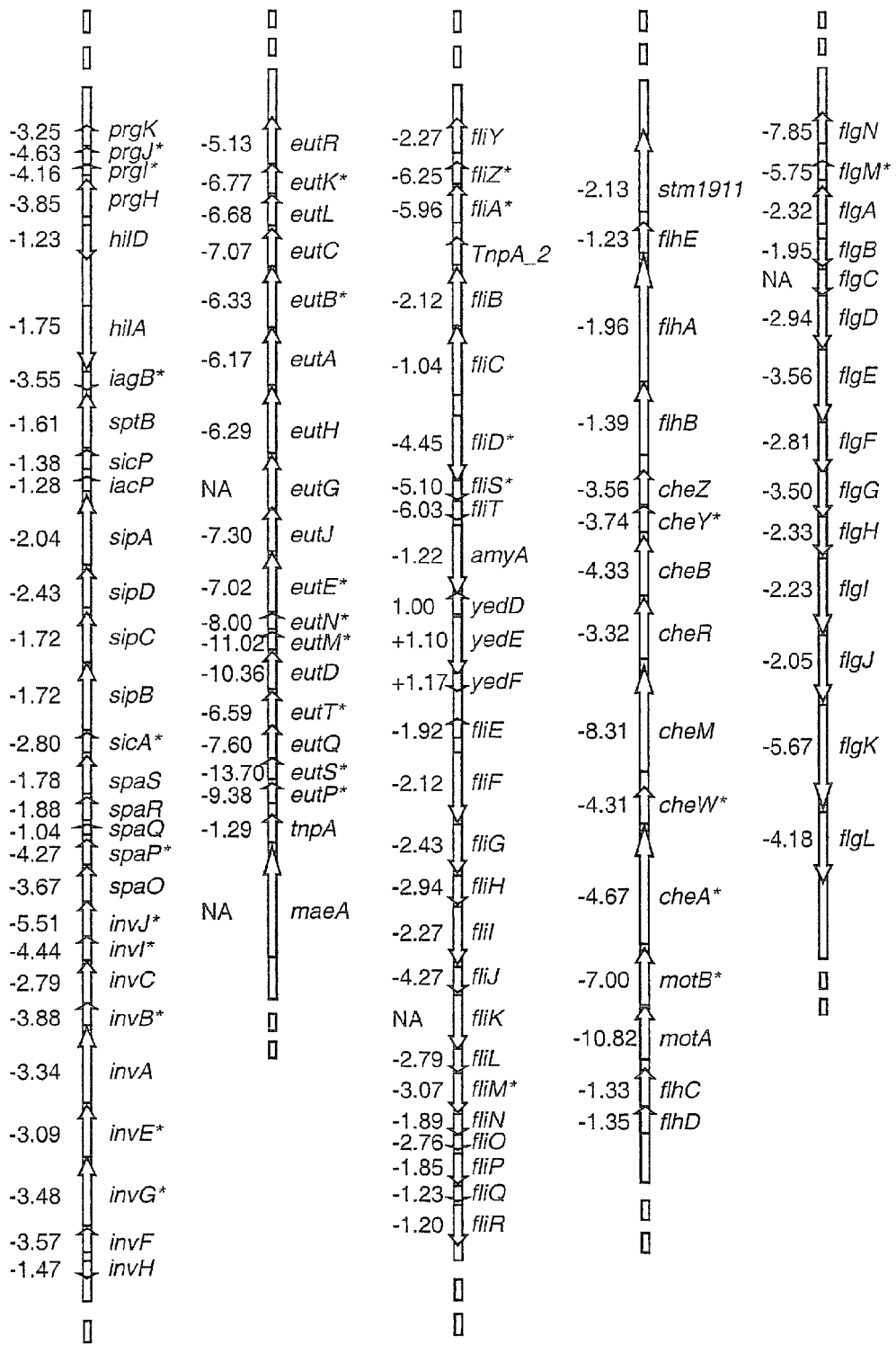
FIG. 4 shows a scheme representing the structural organization of the major genes involved in virulence/SPI-1 (A), ethanolamine utilization (B), and flagellar biosynthesis and motility/swarming (C to E). The names of genes are listed to the right of the arrows, an asterisk next to the gene indicates the presence of at least one FNR motif in the 5' region, and the numbers to the left of the arrows indicate the ratio of gene expression in the fnr mutant relative to that in the WT.

The genes for ethanolamine utilization (eut operon) had lower transcript levels in the fnr mutant (FIG. 4B). Although the FNR-dependent genes for tetrathionate utilization (ttrA-BCSR), a major anaerobic electron acceptor, were not affected by the lack of FNR, this was not surprising since tetrathionate is also needed to induce expression.

Several of the middle flagellar (class 2) genes (e.g., flgN-MDEFGKL and fliZADSTHJLM) and late flagellar (class 3) genes (e.g., cheZYBRMWA, motBA, aer, trg, and tsr) had lower transcript levels in the fnr mutant than in the WT (FIG. 4C to E). There was no significant difference in the transcript levels of the early flagellar genes (class 1) flhD and flhC, whose gene products FlhD/FlhC are the master regulators of flagellar biosynthesis (FIG. 4D). In addition, many newly identified flagellar genes (i.e., mcpA, mcpC, and cheV) had lower expression levels in the fnr mutant, while the expression of mcpB was not affected.

Several genes in SPI-1 (e.g., prgKJIH, iagB, sicA, spaPO, invJICBAEGF) had lower levels of expression in the fnr mutant than in the WT (FIG. 4A). This region contains genes coding for a type three secretion system and for proteins required for invasion and interaction with host cells. The data also show that genes belonging to the other SPIs were unaffected by the lack of FNR. However, the virulence operon srfABC, which is located outside SPI-2 and regulated by a two-component regulatory system (SsrAB) located on SPI-2 (Waterman et al. (2003) *Cell. Microbiol.* 5:501-511; Worley et al., (2000) Mol. Microbiol. 36:749-761), was differentially regulated by FNR. The effects of FNR on a subset of the above-mentioned invasion and virulence genes were further confirmed by measuring the levels of mRNA in the fnr mutant and the WT strains by qRT-PCR (Table 2).

EXAMPLE 5

Effects of FNR on Motility and Flagella

Expression of the flagellar biosynthesis, motility, and chemotaxis genes was lower in the fnr mutant than in the WT. Therefore, the WT, fnr mutant was compared to the mutant cells harboring pfnr for motility in soft agar under anaerobic conditions. The data indicate that the fnr mutant was nonmotile and that the lack of motility was complemented (~75%) by the inclusion of pfnr. The 100% complementation by pfnr is probably due to extra copies of the global regulator FNR. The WT was also compared to the mutant for the presence of flagella by SEM and TEM. Taken together, these data show that the fnr mutant is nonmotile due to the lack of flagella.

EXAMPLE 6

Effects of FNR on Pathogenicity and Killing by Macrophages

Figure 5A:
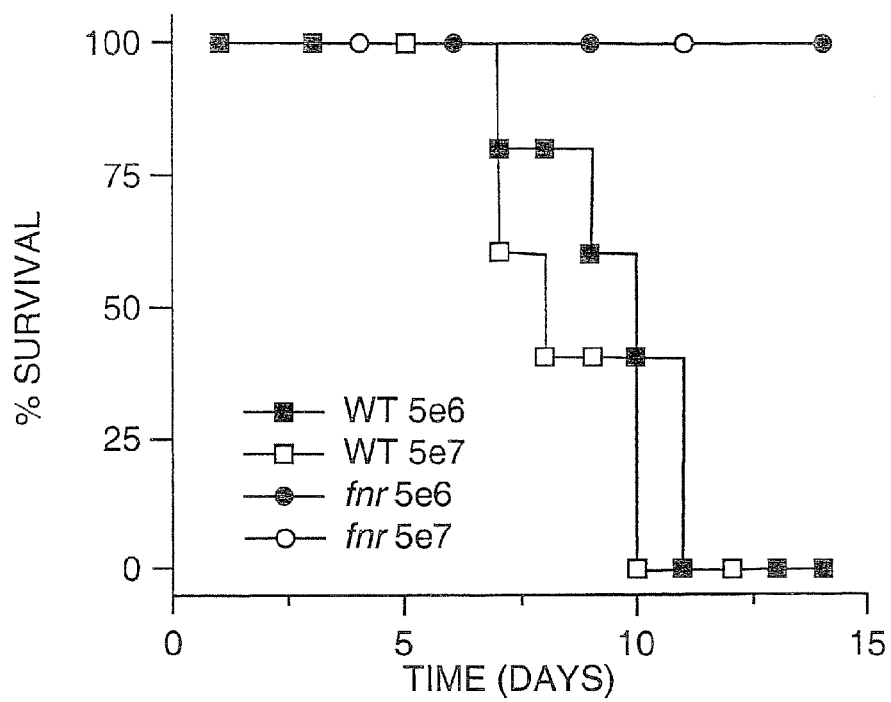
FIG. 5 shows a comparison of the fnr mutant and the WT strain for virulence in 6- to 8-week-old C57BL/6 mice. (A) Groups of 10 mice were inoculated p.o. with $5 \times 10^6$ and $5 \times 10^7$ CFU/mouse. (B) Groups of five mice were challenged i.p. with 250 CFU/mouse, as described. Percent survival is the number of mice surviving relative to the number of mice challenged at time zero.
Figure 5B:
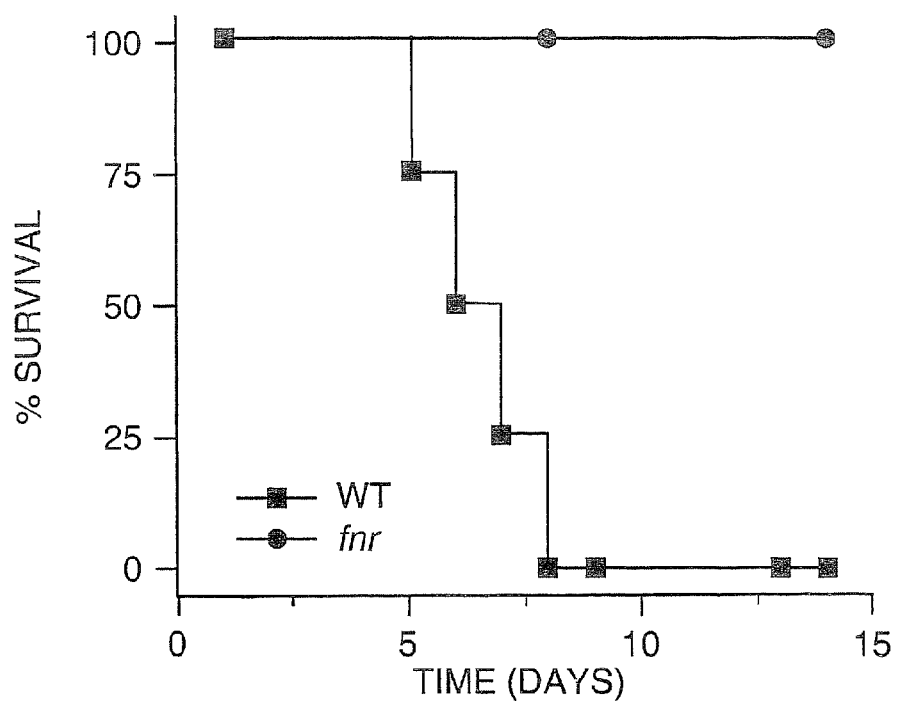
Figure 6A:
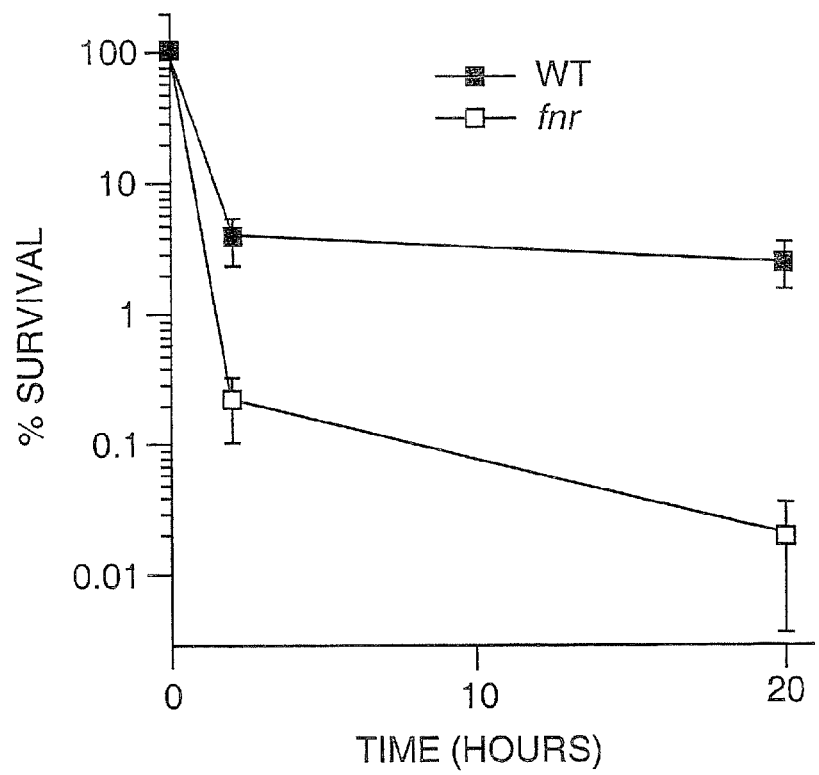
FIG. 6 shows a comparison of the WT, the fnr mutant, and the mutant strain harboring pfnr for survival inside peritoneal macrophages from C57BL/6 mice. The macrophages were harvested and treated as described. (A) Comparison between the fnr mutant and the WT strain. The number of viable cells found inside the macrophages, at time zero, following the removal of extracellular bacteria by washing/gentamicin treatment is defined as 100% survival. (B) Comparison between the WT, the fnr mutant, and the pfnr-complemented mutant. The number of viable cells found inside macrophages at 20 h is expressed as percent survival relative to that found inside macrophages at 2 h.
Figure 6B:
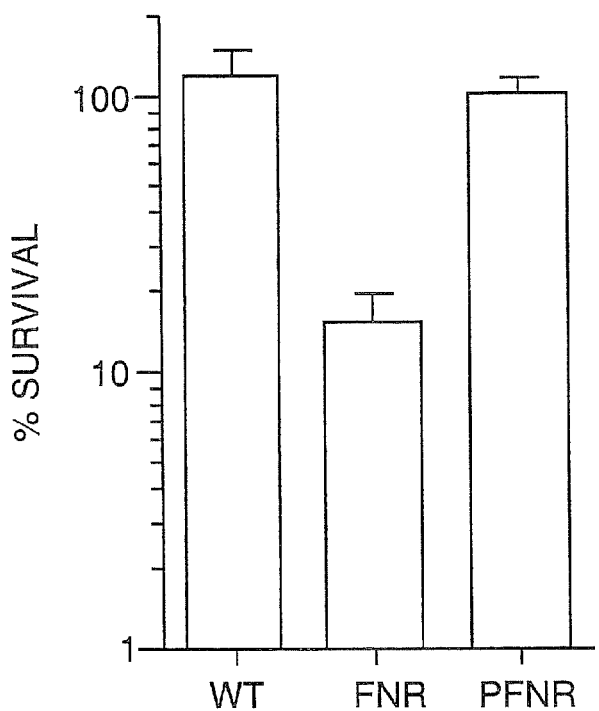
Figure 7A:
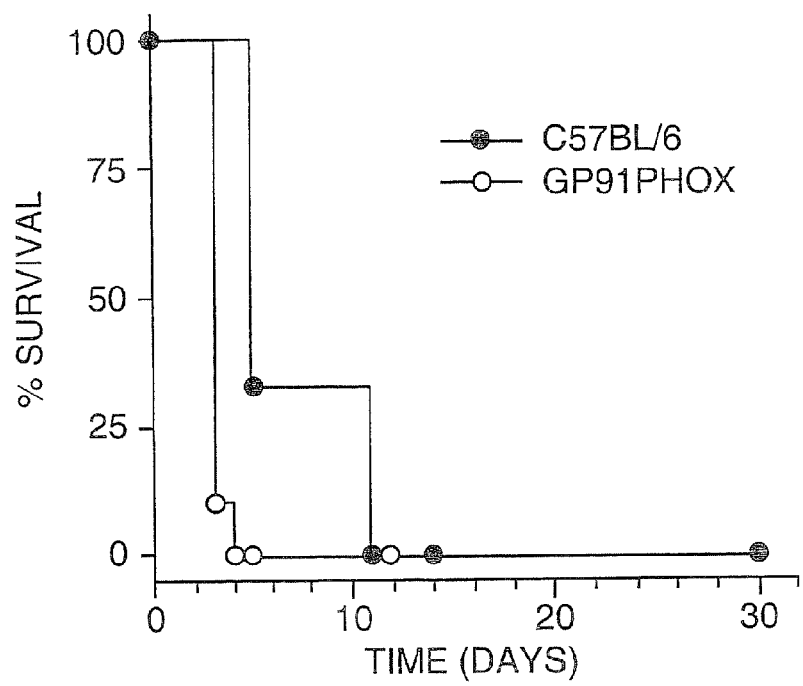
FIG. 7 shows the virulence of the WT and the fnr mutant in C57BL/6 mice and congenic gp91phox$^{-/-}$ mice and survival of the bacteria inside peritoneal macrophages. The mice were challenged i.p. with 250 CFU/mouse, as described. (A) C57Bl/6 mice and gp91phox$^{-/-}$ mice treated with the WT strain. (B) C57Bl/6 and gp91phox$^{-/-}$ mice treated with the fnr mutant. (C) Survival of the WT and the fnr mutant inside macrophages from C57Bl/6 and gp91phox$^{-/-}$ mice. The number of viable cells at 20 h is expressed as percent survival relative to that found inside the macrophages at time zero.
Figure 7B:
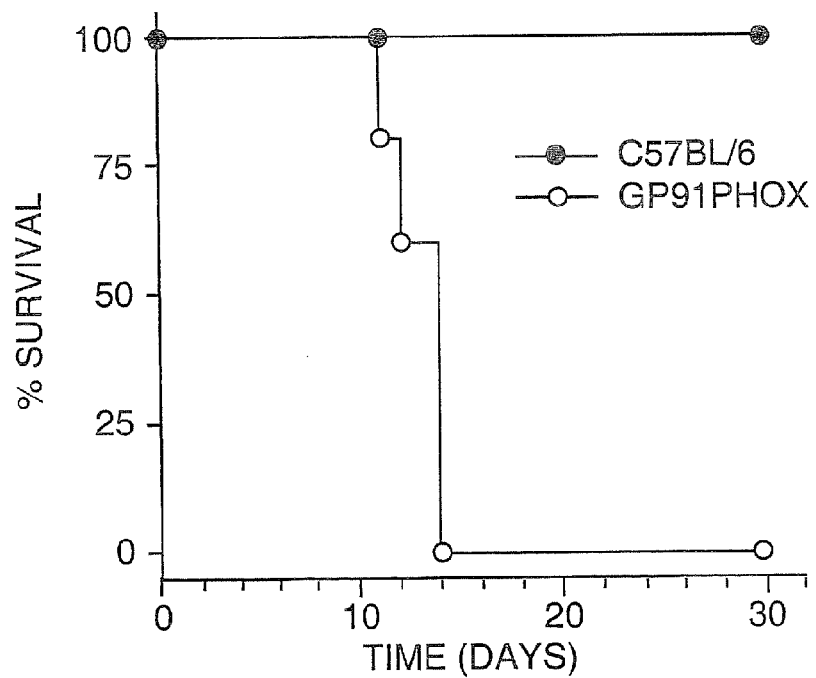
Figure 7C:
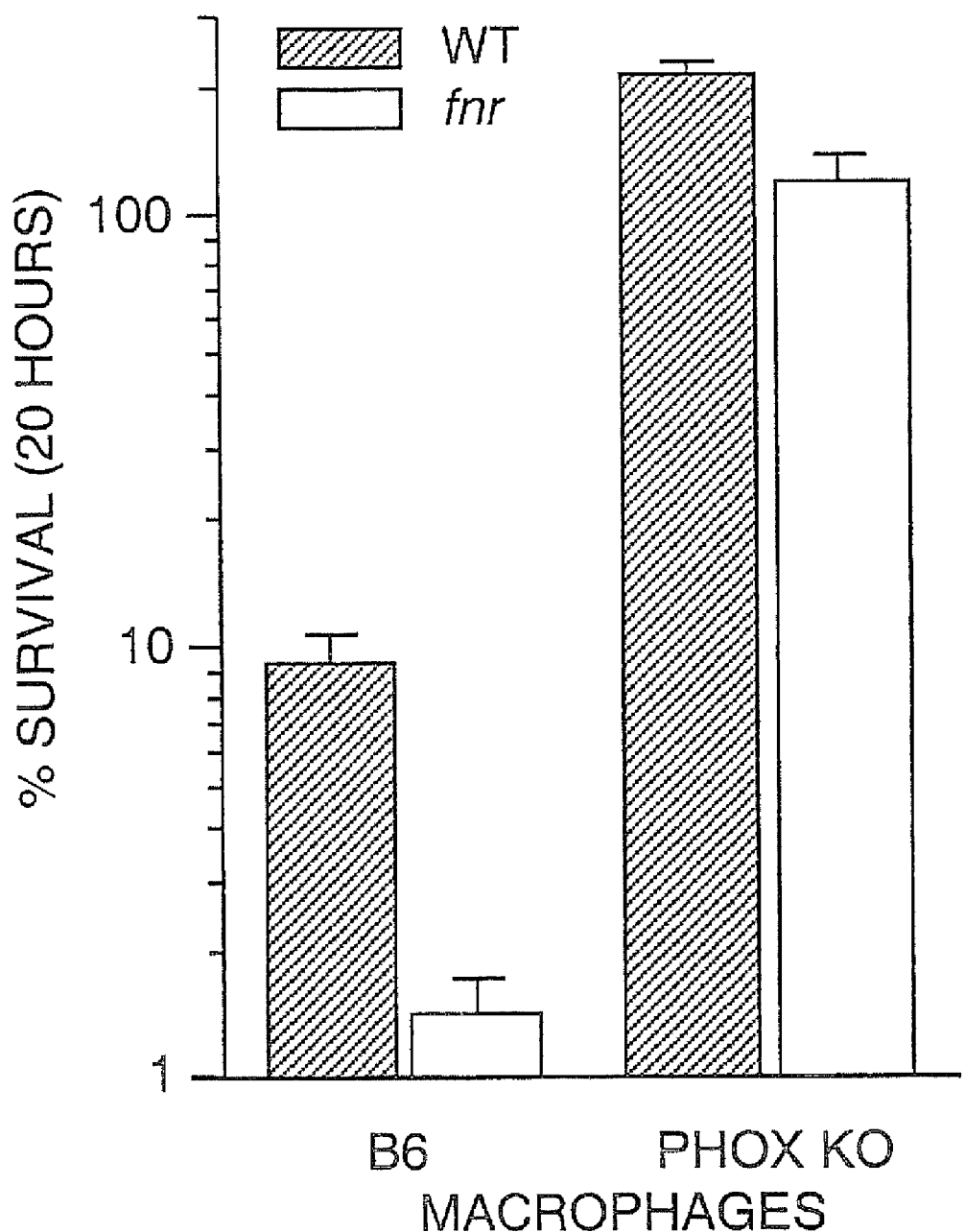

FNR positively regulates the expression of various loci (see Table 3), such as motility and SPI-1 genes that are important determinants for *Salmonella* pathogenesis, so the virulence of fnr in a murine model of mucosal and acute infection was tested. In immunocompetent C57BL/6 mice, the fnr mutant was completely attenuated over a 15-day period following an oral challenge with $5\times10^6$ or $5\times10^7$ CFU/mouse, while the WT strain killed all mice within 10 or 12 days, respectively (FIG. 5A). The mutant strain was also 100% attenuated when 250 CFU/mouse were inoculated i.p. (FIG. 5B). The different *Salmonella* strains were also tested for the ability to survive killing by macrophages (FIG. 6). Similar numbers of fnr mutant and WT cells were recovered from the macrophages 25 min after infection (designated as time zero postinfection). Data in FIG. 6A indicate that the lack of FNR resulted in a dramatic reduction in the ability of *Salmonella* to replicate in macrophages. Interestingly, most of the killing of the WT by macrophages took place during the first 2 h postinfection (i.e., the WT resisted further killing beyond 2 h), while the viability of the fnr mutant continued to decline by 1 log between 2 and 20 h postinfection (FIGS. 6A and B). Data in FIG. 6B also show that this phenotype is complemented in fnr mutant cells harboring pfnr. Congenic iNOS−/− mice (unable to make NO.) and pg91 phox$^{-/-}$ mice (defective in oxidative burst oxidase) were used to examine the roles of reactive nitrogen and oxygen species (RNS and ROS), respectively, in resistance to an acute systemic infection with FNR-deficient or WT *Salmonella*. The fnr mutant was as attenuated in iNOS−/− mice as in congenic WT C57BL/6 controls. In sharp contrast, the fnr mutant killed pg91phox$^{-/-}$ mice, albeit at a lower rate than the WT strain (FIGS. 7A and B). Consistent with the in vivo data, the WT and the isogenic fnr mutant survived to similar extents in NADPH oxidase-deficient macrophages isolated from pg91phox$^{-/-}$ mice (FIG. 7C).

The foregoing is illustrative of the present invention, and is not to be construed as limiting thereof. The invention is defined by the following claims, with equivalents of the claims to be included therein.

TABLE 1

Validation of microarray data using qRT-PCR of randomly selected genes relative to the housekeeping gene, rpoD[a].

| Locus[b] | Name[c] | Primer sequence[d] | SEQ ID NO: | Fragment (bp)[e] | *S*. Typhimurium Gene Function[f] | Ratio of fnr mutant/WT qRT-PCR[g] | Micro-array[h] | Log$_2$ ratio qRT-PCR[i] | Micro-array[j] |
|---|---|---|---|---|---|---|---|---|---|
| STM3217 | aer | CGTACAACATCTTAATCGTAGC TTCGTTCAGATCATTATTACCC | 3 4 | 163 | Aerotaxis sensor receptor; senses cellular redox state or proton motive force | 0.190 | 0.210 | −2.4 | −2.3 |
| STM1781 | cheM | GCCAATTTCAAAAATATGACG GTCCAGAAACTGAATAAGTTCG | 5 6 | 114 | Methyl-accepting chemotaxis protein II; aspartate sensor-receptor | 0.036 | 0.120 | −4.8 | −3.1 |
| STM0441 | cyoC | TATTTAGCTCCATTACCTACGG GGAATTCATAGAGTTCCATCC | 7 8 | 134 | Cytochrome o ubiquinol oxidase subunit III | 153.967 | 7.096 | 7.3 | 2.8 |
| STM1803 | dadA | TAACCTTTCGCTTTAATACTCC GATATCAACAATGCCTTTAAGC | 9 10 | 155 | D-Amino acid dehydrogenase subunit | 2.835 | 3.169 | 1.5 | 1.7 |
| STM0964 | dmsA | AGCGTCTTATCAAAGAGTATGG TCACCGTAGTGATTAAGATAACC | 11 12 | 154 | Anaerobic dimethyl sulfoxide reductase, subunit A | 0.001 | 0.005 | −9.8 | −7.6 |
| STM2892-3 | invJ | TTGCTATCGTCTAAAAATAGGC TTGATATTATCGTCAGAGATTCC | 13 14 | 128 | Surface presentation of antigens; secretory proteins | 0.246 | 0.182 | −2.0 | −2.5 |
| STM2324 | nuoF | GGATATCGAGACACTTGAGC GATTAAATGGGTATTACTGAACG | 15 16 | 163 | NADH dehydrogenase I, chain F | 2.894 | 2.600 | 1.5 | 1.4 |
| STM0650 | STM0650 | CAACAGCTTATTGATTTAGTGG CTAACGATTTTTCTTCAATGG | 17 18 | 130 | Putative hydrolase, C terminus | 0.476 | 0.219 | −1.1 | −2.2 |
| STM2787 | STM2787 | AAGCGAATACAGCTATGAACC ATTAGCTTTTGCAGAACATGG | 19 20 | 144 | Tricarboxylic transport | 28.241 | 6.892 | 4.8 | 2.8 |
| STM4463 | STM4463 | AAGGTATCAGCCAGTCTACG CGTATGGATAAGGATAAATTCG | 21 22 | 142 | Putative arginine repressor | 0.325 | 0.181 | −1.6 | −2.5 |
| STM4535 | STM4535 | TAAGCCAGCAGGTAGATACG CGACATAAAGAGATCGATAACC | 23 24 | 139 | Putative PTS permease | 6.053 | 8.217 | 2.6 | 3.0 |
| STM2464 | eutN | AGGACAAATCGTATGTACCG ACCAGCAGTACCCACTCTCC | 25 26 | 153 | Putative detox protein in ethanolamine utilization | 0.062 | 0.125 | −4.0 | −3.0 |
| STM2454 | eutR | GGTAAAAGAGCAGCATAAAGC ATTATCACTCAAGACCTTACGC | 27 28 | 118 | Putative regulator; ethanolamine operon (AraC/XylS family) | 0.043 | 0.195 | −4.6 | −2.4 |
| STM2470 | eutS | AATAAAGAACGCATTATTCAGG GTTAAAGTCATAATGCCAATCG | 29 30 | 137 | Putative carboxysome structural protein; ethanol utilization | 0.049 | 0.073 | −4.3 | −3.8 |
| STM1172 | flgM | AGCGACATTAATATGGAACG TTTACTCTGTAAGTAGCTCTGC | 31 32 | 126 | Anti-FliA (anti-sigma) factor; also known as RflB protein | 0.050 | 0.174 | −4.3 | −2.5 |

TABLE 1-continued

Validation of microarray data using qRT-PCR of randomly selected genes relative to the housekeeping gene, rpoD[a].

| Locus[b] | Name[c] | Primer sequence[d] | SEQ ID NO: | Fragment (bp)[e] | S. Typhimurium Gene Function[f] | Ratio of fnr mutant/WT | | Log$_2$ ratio | |
|---|---|---|---|---|---|---|---|---|---|
| | | | | | | qRT-PCR[g] | Microarray[h] | qRT-PCR[i] | Microarray[j] |
| STM3692 | lldP | TGATTAAACTCAAGCTGAAAGG<br>CCGAAATTTTATAGACAAAGACC | 33<br>34 | 189 | LctP transporter; L-lactate permease | 76.492 | 16.003 | 6.3 | 4.0 |
| STM3693 | lldR | GAACAGAATATCGTGCAACC<br>GAGTCTGATTTTCTCTTTGTCG | 35<br>36 | 153 | Putative transcriptional regulator for lct operon (GntR family) | 68.378 | 30.597 | 6.1 | 4.9 |
| STM1923 | motA | GGTTATCGGTACAGTTTTCG<br>TAGATTTTGTGTATTTCGAACG | 37<br>38 | 194 | Proton conductor component of motor; torque generator | 0.048 | 0.092 | −4.4 | −3.4 |
| STM4277 | nrfA | GACTAACTCTCTGTCGAAAACC<br>ATTTTATGGTCGGTGTAGAGC | 39<br>40 | 159 | Nitrite reductase; periplasmic cytochrome c$_{552}$ | 0.051 | 0.324 | −4.3 | −1.6 |

[a]STM3211 (rpoD) was used as the reference gene where no significant change in expression level was observed. The primer sequences (5' to 3') used for rpoD were as follows: CGATGTCTCTGAAGAAGTGC (forward; SEQ ID NO: 41) and TTCAACCATCTCTTTCTTCG (reverse; SEQ ID NO: 42). The size of the fragment generated is 150 bp.
[b]Location of the open reading frame (ORF) in the S. Typhimurium LT2 genome.
[c]Respective gene name or symbol.
[d]For each set, the first primer is the forward primer and the second primer is the reverse primer.
[e]Size of the amplified PCR product.
[f]Functional classification according to the KEGG (Kyoto Encyclopedia of Genes and Genomes) database.
[g]Expression levels of quantitative reverse transcriptase polymerase chain reaction - values shown as the ratio between the fnr mutant and the wild-type; where values <1 indicate that FNR acts as an activator, and values >1 indicate FNR acts as a repressor.
[h]Expression levels from the microarray data - values shown as the ratio between the fnr mutant and the wild-type; where values <1 indicate that FNR acts as an activator, and values >1 indicate FNR acts as a repressor.
[i]Expression levels of quantitative reverse transcriptase polymerase chain reaction comparing the fnr mutant versus the wild-type - shown in signal to log$_2$ ratio (SLR).
[j]Expression levels of microarray data comparing the fnr mutant versus the wild-type - shown in signal to log$_2$ ratio (SLR).

TABLE 2 qRT-PCR of Selected Invasion and Virulence Genes[a]

| Locus[b] | Name[c] | Primer sequence[d] | SEQ ID NO: | Fragment size (bp)[e] | Ratio[f] |
|---|---|---|---|---|---|
| STM2893 | invI | 5'-CTTCGCTATCAGGATGAGG-3'<br>5'-CGAACAATAGACTGCTTACG-3' | 43<br>44 | 161 | −9.27 |
| STM2874 | prgH | 5'-GGCTCGTCAGGTTTTAGC-3'<br>5'-CTTGCTCATCGTGTTTCG-3' | 45<br>46 | 190 | −8.45 |
| STM2871 | prgK | 5'-ATTCGCTGGTATCGTCTCC-3'<br>5'-GAACCTCGTTCATATACGG-3' | 47<br>48 | 199 | −8.56 |
| STM2886 | sicA | 5'-GATTACACCATGGGACTGG-3'<br>5'-CAGAGACTCATCTTCAGTACG-3' | 49<br>50 | 207 | −3.92 |
| STM1593 | srfA | 5'-AGGCGGCATTTAGTCAGG-3'<br>5'-GACAGGTAAGCTCCACAGC-3' | 51<br>52 | 176 | −4.33 |
| STM1594 | srfB | 5'-GGTACCAGAAATACAGATGG-3'<br>5'-GCCGATATCAATCGATGC-3' | 53<br>54 | 190 | −6.55 |

[a]STM3211 (rpoD) was used as the reference gene where no significant change in expression level was observed. The primer sequences used for rpoD were as follows: 5'-CGATGTCTCTGAAGAAGTGC-3' (forward; SEQ ID NO: 41) and 5'-TTCAACCATCTCTTTCTTCG-3' (reverse; SEQ ID NO: 42). The size of the fragment generated was 150 bp.
[b]Location of the open reading frame (ORF) in the S. Typhimurium LT2 genome.
[c]Respective gene name or symbol.
[d]For each set, the first primer is the forward and the second primer is the reverse.
[e]Size of the amplified PCR product.
[f]Ratio of the transcription levels in the fnr mutant relative to the wild-type.

TABLE 3

Differentially expressed genes and the presence/absence of putative FNR-binding motifs in their 5' regions.

| Locus[a] | Category[b] | Name[c] | STM Gene Function[d] | t value[e] | DF[f] | Prot t[g] | Ratio[h] | Strand[i] | Start[j] | End[k] | Sequence[l] | SEQ ID NO: | Score[m] | In (P)[n] |
|---|---|---|---|---|---|---|---|---|---|---|---|---|---|---|
| PSLT018 | — | pefA | plasmid-encoded fimbriae; major fimbrial subunit | −6.11 | 5.92 | 9.16E-04 | −2.56 | | | | | | | |
| PSLT019 | — | pefB | plasmid-encoded fimbriae; regulation | −9.86 | 6.59 | 3.46E-05 | −4.59 | R | −337 | −316 | tttcTTTTTGATATATGTCTTTTCatgta | 55 | 5.41 | −7.58 |
| STM0002 | E | thrA | aspartokinase I, bifunctional enzyme N-terminal is aspartokinase1 and C-terminal is homoserine dehydrogenase I | −11.82 | 7.27 | 5.20E-06 | −3.33 | R | −351 | −330 | GGAATTGGTTGAAAATAAATATatcg | 56 | 5.71 | −7.83 |
| STM0041 | G | STM0041 | putative glycosyl hydrolase | −9.21 | 5.78 | 1.15E-04 | −3.19 | | | | | | | |
| STM0042 | G | STM0042 | putative sodium galactoside symporter | −12.79 | 5.16 | 4.17E-05 | −3.32 | | | | | | | |
| STM0153 | C | aceF | pyruvate dehydrogenase, dihydrolipoyltransacetylase component | −7.07 | 5.72 | 4.93E-04 | −3.83 | D | −52 | −31 | gaatAATGGCTATCGAAATCAAAGTAccgg | 57 | 4.98 | −7.24 |
| STM0178 | G | yadI | putative PTS enzyme | −6.35 | 5.43 | 1.05E-03 | −7.00 | D | −263 | −242 | tttaTAATATATATATTTAATCAATTATtttg | 58 | 5.19 | −7.41 |
| STM0439 | H | cyoE | protohaeme IX farnesyltransferase (haeme O biosynthesis) | 9.48 | 5.20 | 1.77E-04 | 7.71 | D | −102 | −81 | tctgGATTATGTGGAACCTCAACTACaaca | 59 | 4.54 | −6.9 |
| STM0440 | C | cyoD | cytochrome o ubiquinol oxidase subunit IV | 13.11 | 5.21 | 3.45E-05 | 7.05 | R | −326 | −305 | tatcGGGATGAACTCTATGAATTCatca | 60 | 4.64 | −6.98 |
| STM0441 | C | cyoC | cytochrome o ubiquinol oxidase subunit III | 36.33 | 5.46 | 9.96E-08 | 7.10 | | | | | | | |

TABLE 3-continued

Differentially expressed genes and the presence/absence of putative FNR-binding motifs in their 5' regions.

| Locus[a] | Category[b] | Name[c] | STM Gene Function[d] | t value[e] | DF[f] | Prot t[g] | Ratio[h] | Strand[i] | Start[j] | End[k] | Sequence[l] | SEQ ID NO: | Score[m] | In (P)[n] |
|---|---|---|---|---|---|---|---|---|---|---|---|---|---|---|
| STM0442 | C | cyoB | cytochrome o ubiquinol oxidase subunit I | 22.84 | 5.64 | 8.89E-07 | 5.05 | R | -206 | -185 | aaccTGATTTGTTCAAGGACGTTATTaaca | 61 | 4.18 | -6.63 |
| STM0443 | C | cyoA | cytochrome o ubiquinol oxidase subunit II | 22.81 | 5.46 | 1.25E-06 | 4.51 | D | -68 | -47 | ccgtGAAATTGAGGTCGTTAAATGAgactc | 62 | 5.84 | -7.94 |
| STM0465 | S | ybaY | glycoprotein/polysaccharide metabolism | -15.14 | 5.29 | 1.46E-05 | -4.75 | R | -75 | -54 | ctggTGCATTGATGATAAGGAGAATTgaat | 63 | 5.34 | -7.53 |
| STM0467 | — | ffs | signal recognition particle, RNA component | -9.58 | 5.21 | 1.67E-04 | -4.45 | | | | | | | |
| STM0650 | G | STM0650 | putative hydrolase C-terminus | -9.87 | 5.46 | 1.10E-04 | -4.56 | D | -55 | -34 | aaggGAAAATGATTATGAGCAATGAgactt | 64 | 6.95 | -8.95 |
| STM0659 | O | hscC | putative heatshock protein, homolog of hsp70 in Hsc66 subfamily | -15.49 | 8.16 | 2.46E-07 | -2.82 | R | -128 | -107 | gcgtGACATTGATAAAGATCACCACGccag | 65 | 5.25 | -7.46 |
| STM0662 | E | gltL | ABC superfamily (atp_bind), glutamate/aspartate transporter | 12.96 | 5.46 | 2.61E-05 | 4.39 | R | -309 | -288 | actgGCAGTCGATGAAGCTCATTATTctgc | 66 | 5.97 | -8.06 |
| STM0663 | E | gltK | ABC superfamily (membrane), glutamate/aspartate transporter | 12.08 | 8.19 | 1.67E-06 | 2.81 | | | | | | | |
| STM0664 | E | gltJ | ABC superfamily (membrane), glutamate/aspartate transporter | 12.47 | 7.16 | 4.09E-06 | 2.67 | D | -62 | -41 | tttcGGAGTAGATGTATGTCAATAGActgg | 67 | 4.58 | -6.93 |
| STM0665 | E | gltI | ABC superfamily (bind_prot), glutamate/aspartate transporter | 10.65 | 5.77 | 5.20E-05 | 4.24 | D | -216 | -195 | taggATTTTTGCCTCTGAACGGTGCCgcgc | 68 | 5.67 | -7.8 |
| STM0699 | R | STM0699 | putative cytoplasmic protein | -15.11 | 6.35 | 3.25E-06 | -4.22 | R | -30 | -9 | ggaaGTCACTGATATAGCAGAAATACtggc | 69 | 6.99 | -8.99 |

TABLE 3-continued

Differentially expressed genes and the presence/absence of putative FNR-binding motifs in their 5' regions.

| Locus[a] | Cat-egory[b] | Name[c] | STM Gene Function[d] | t value[e] | DF[f] | Prot t[g] | Ratio[h] | Strand[i] | Start[j] | End[k] | Sequence[l] | SEQ ID NO: | Score[m] | In (P)[n] |
|---|---|---|---|---|---|---|---|---|---|---|---|---|---|---|
| STM0728 | L | nei | endonuclease VIII removing oxidized pyrimidines may also remove oxidized purines in absence of MutY and Fpg [EC: 3.2.-.-] | 16.01 | 6.47 | 1.90E-06 | 2.57 | D | -80 | -59 | tccaTTAATCAACTGTTAACAAGGAtatt | 70 | 5.12 | -7.35 |
| STM0737 | C | sucB | 2-oxoglutarate dehydrogenase (dihydrolipoyltranssuccinase E2 component) | 14.92 | 9.44 | 7.01E-08 | 2.75 | | | | | | | |
| STM0738 | C | sucC | succinyl-CoA synthetase, beta subunit | 21.50 | 5.79 | 9.65E-07 | 4.03 | D | -39 | -18 | acatGAATATCAGGCAAAACAACTTTtgc | 71 | 6.69 | -8.71 |
| STM0739 | C | sucD | succinyl-CoA synthetase, alpha subunit | 23.03 | 5.62 | 8.87E-07 | 4.66 | | | | | | | |
| STM0740 | C | cydA | cytochrome d terminal oxidase, polypeptide subunit I [EC: 1.10.3.-] | 17.22 | 6.09 | 2.13E-06 | 2.55 | R | -307 | -286 | gccaTAAATTGATCGCTGTCGAAAAagca | 72 | 10.38 | -13.11 |
| STM0741 | C | cydB | cytochrome d terminal oxidase polypeptide subunit II | 21.16 | 5.67 | 1.30E-06 | 3.74 | D | -169 | -148 | cagaATTGTTCCTGATGTTCAAATTgcac | 73 | 5.62 | -7.76 |
| STM0742 | S | ybgT | putative outer membrane lipoprotein | 11.38 | 7.56 | 5.01E-06 | 4.34 | R | -165 | -144 | tgttCGTACCGATCATTCTGATCTACacca | 74 | 4.83 | -7.12 |
| STM0743 | S | ybgE | putative inner membrane lipoprotein | 13.92 | 9.36 | 1.44E-07 | 3.48 | R | -102 | -81 | cacgTGCACTGTTGGAAGAGGTTATCcgac | 75 | 4.31 | -6.72 |
| STM0759 | — | ybgS | putative homeobox protein | -14.35 | 5.04 | 2.80E-05 | -4.60 | | | | | | | |
| STM0761 | C | STM0761 | fumarate hydratase Class I anaerobic | 6.55 | 5.53 | 8.38E-04 | 4.48 | | | | | | | |

TABLE 3-continued

Differentially expressed genes and the presence/absence of putative FNR-binding motifs in their 5' regions.

| Locus[a] | Category[b] | Name[c] | STM Gene Function[d] | t value[e] | DF[f] | Prot t[g] | Ratio[h] | Strand[i] | Start[j] | End[k] | Sequence[l] | SEQ ID NO: | Score[m] | ln (P)[n] |
|---|---|---|---|---|---|---|---|---|---|---|---|---|---|---|
| STM0762 | C | STM0762 | fumarate hydratase, alpha subunit | 8.26 | 5.15 | 3.67E-04 | 5.69 | D | -340 | -319 | agttTATTTTCTTTCTATCAAATAAtgtc | 76 | 6.33 | -8.37 |
| STM0781 | P | modA | ABC superfamily (peri_perm), molybdate transporter | -22.42 | 7.25 | 5.78E-08 | -3.12 | R | -140 | -119 | tttaATCGTTAATGGGTATGAATAACcgct | 77 | 6.43 | -8.47 |
| STM0790 | – | hutU | pseudogene; frameshift relative to Pseudomonas putida urocanate hydratase (HUTU) (SW: P25080) | 9.49 | 5.45 | 1.36E-04 | 5.44 | | | | | | | |
| STM0791 | E | hutH | histidine ammonia lyase | 19.06 | 6.84 | 3.51E-07 | 4.55 | | | | | | | |
| STM0828 | E | glnQ | ABC superfamily (atp_bind), glutamine high-affinity transporter | 8.23 | 6.06 | 1.66E-04 | 2.86 | | | | | | | |
| STM0830 | E | glnH | ABC superfamily (bind_prot), glutamine high-affinity transporter | 9.60 | 5.47 | 1.26E-04 | 3.70 | | | | | | | |
| STM0853 | – | yliH | putative cytoplasmic protein | -15.57 | 6.53 | 2.08E-06 | -3.33 | | | | | | | |
| STM0907 | R | aSTM0907 | Fels-1 prophage; putative chitinase | -6.72 | 5.39 | 8.16E-04 | -3.12 | | | | | | | |
| STM0912 | O | aSTM0912 | Fels-1 prophage; protease subunits of ATP-dependent proteases, ClpP family | 11.94 | 7.50 | 3.81E-06 | 3.40 | | | | | | | |
| STM0964 | C | dmsA | anaerobic dimethyl sulfoxide reductase, subunit A | -18.73 | 5.00 | 7.95E-06 | -200.85 | D | -151 | -130 | ctacTTTTCGATATATCAGACTTtata | 78 | 7.44 | -9.43 |
| STM0965 | C | dmsB | anaerobic dimethyl sulfoxide reductase, subunit B | -53.46 | 5.29 | 1.93E-08 | -62.55 | | | | | | | |

TABLE 3-continued

Differentially expressed genes and the presence/absence of putative FNR-binding motifs in their 5' regions.

| Locus[a] | Cat-ego-ry[b] | STM Gene Name[c] | Function[d] | t value[e] | DF[f] | Prot t[g] | Ratio[h] | Strand[i] | Start[j] | End[k] | Sequence[l] | SEQ ID NO: | Score[m] | In (P)[n] |
|---|---|---|---|---|---|---|---|---|---|---|---|---|---|---|
| STM0966 | R | dmsC | anaerobic dimethyl sulfoxide reductase, subunit C | −28.93 | 5.04 | 8.52E-07 | −23.60 | R | −260 | −239 | gtaaGAAACCGATTTGCGTCGAATCtgcc | 79 | 8.79 | −10.93 |
| STM0972 | — | STM0972 | homologous to secreted protein sopD | 5.62 | 6.48 | 1.04E-03 | 3.07 | D | −256 | −235 | aataATTCTCAACATAATTCAGATGTgtcc | 80 | 4.68 | −7.01 |
| STM0974 | P | focA | putative FNT family, formate transporter (formate channel 1) | −7.49 | 5.77 | 3.53E-04 | −3.19 | R | −129 | −108 | ggcgAGATATGATCTATATCAAATTCtcat | 81 | 8.35 | −10.41 |
| STM0989 | — | STM0989 | mukF protein (killing factor KicB) | −10.99 | 5.11 | 9.47E-05 | −4.90 | R | −279 | −258 | cgtgCGCGCTGAAATGCGTTAACATGatcc | 82 | 4 | −6.5 |
| STM1118 | — | yccJ | putative cytoplasmic protein | −9.37 | 5.50 | 1.38E-04 | −4.94 | | | | | | | |
| STM1119 | R | wraB | trp-repressor binding protein | −10.54 | 5.13 | 1.14E-04 | −6.45 | D | −167 | −146 | attaATTATTGTTATAAATCAAAGAAatgg | 83 | 9.3 | −11.57 |
| STM1123 | S | STM1123 | putative periplasmic protein | 4.28 | 6.28 | 4.69E-03 | 3.13 | | | | | | | |
| STM1124 | — | putA | bifunctional in plasma membrane proline dehydrogenase and pyrroline-5-carboxylate dehydrogenase OR in cytoplasm a transcriptional repressor | 24.50 | 6.20 | 2.07E-07 | 7.57 | | | | | | | |
| STM1125 | E | putP | SSS family, major sodium/proline symporter | 14.50 | 5.46 | 1.44E-05 | 7.16 | D | −195 | −174 | tgtaAATGGTGTGTTAAATCGATTGTgaat | 84 | 7.78 | −9.79 |
| STM1126 | — | phoH | PhoB-dependent, ATP-binding pho regulon component | 9.41 | 6.88 | 3.56E-05 | 2.63 | NA | NA | NA | NA | NA | NA | NA |

TABLE 3-continued

Differentially expressed genes and the presence/absence of putative FNR-binding motifs in their 5' regions.

| Locus[a] | Cat-ego-ry[b] | Name[c] | STM Gene Function[d] | t value[e] | DF[f] | Prot t[g] | Ratio[h] | Strand[i] | Start[j] | End[k] | Sequence[l] | SEQ ID NO: | Score[m] | In (P)[n] |
|---|---|---|---|---|---|---|---|---|---|---|---|---|---|---|
| STM1128 | E | STM1128 | putative sodium/glucose cotransporter | -18.20 | 6.39 | 9.58E-07 | -4.78 | R | -289 | -268 | cctgAAGCCTGTTTGAACGCAATATCggat | 85 | 5.25 | -7.45 |
| STM1129 | G | STM1129 | putative inner membrane protein | -15.72 | 5.52 | 8.59E-06 | -6.50 | | | | | | | |
| STM1130 | S | STM1130 | putative inner membrane protein | -9.85 | 5.15 | 1.56E-04 | -11.85 | | | | | | | |
| STM1131 | — | STM1131 | putative outer membrane protein | -10.50 | 5.84 | 5.25E-05 | -4.67 | D | -58 | -37 | cggaGTATTTTATGAAAATCAACAAAtatc | 86 | 7.06 | -9.06 |
| STM1132 | G | STM1132 | putative sugar transort protein putative | -9.42 | 5.29 | 1.67E-04 | -6.20 | R | -120 | -99 | ttcgGCAATTGATATGACTTAAAATtaat | 87 | 10.03 | -12.57 |
| STM1133 | R | STM1133 | putative dehydrogenases and related proteins | -14.98 | 5.29 | 1.56E-05 | -5.56 | D | -90 | -69 | cgtgAAAGTTTCAATCAACAAAGAattt | 88 | 4.6 | -6.94 |
| STM1138 | — | ycdZ | putative inner membrane protein | -9.09 | 5.03 | 2.62E-04 | -11.00 | D | -106 | -85 | agaaTAATGTGATGTAAATCACCCTTaact | 89 | 5.45 | -7.62 |
| STM1171 | N | flgN | flagellar biosynthesis: belived to be export chaperone for FlgK and FlgL | -12.69 | 5.24 | 3.93E-05 | -7.85 | | | | | | | |
| STM1172 | K | flgM | anti-FliA (anti-sigma) factor; also known as RflB protein | -13.69 | 5.30 | 2.46E-05 | -5.75 | R | -72 | -51 | cgtaACCCTCGATGAGGATAAATAAtgag | 90 | 5.44 | -7.61 |
| STM1176 | N | flgD | flagellar biosynthesis, initiation of hook assembly | -11.76 | 5.49 | 4.21E-05 | -2.94 | | | | | | | |
| STM1177 | N | flgE | flagellar biosynthesis, hook protein | -14.54 | 5.88 | 7.83E-06 | -3.56 | | | | | | | |
| STM1178 | N | flgF | flagellar biosynthesis, cell- | -7.59 | 6.06 | 2.58E-04 | -2.81 | | | | | | | |

TABLE 3-continued

Differentially expressed genes and the presence/absence of putative FNR-binding motifs in their 5' regions.

| Locus[a] | Cat- ego- ry[b] | Name[c] | STM Gene Function[d] | t value[e] | DF[f] | Prot t[g] | Ratio[h] | Strand[i] | Start[j] | End[k] | Sequence[l] | SEQ ID NO: | Score[m] | ln (P)[n] |
|---|---|---|---|---|---|---|---|---|---|---|---|---|---|---|
| STM1179 | N | flgG | proximal portion of basal-body rod flagellar biosynthesis, cell-distal portion of basal-body rod | −7.52 | 5.56 | 4.10E-04 | −3.50 | | | | | | | |
| STM1183 | N | flgK | flagellar biosynthesis, hook-filament junction protein 1 | −11.80 | 5.20 | 5.95E-05 | −5.67 | | | | | | | |
| STM1184 | N | flgL | flagellar biosynthesis; hook-filament junction protein | −11.04 | 5.33 | 7.16E-05 | −4.18 | | | | | | | |
| STM1227 | E | pepT | putative peptidase T(aminotripeptidase) | −13.20 | 6.24 | 8.57E-06 | −2.67 | | | | | | | |
| STM1254 | — | STM1254 | putative outer membrane lipoprotein | −8.06 | 5.65 | 2.64E-04 | −3.82 | | | | | | | |
| STM1271 | P | yeaR | putative cytoplasmic protein | 13.89 | 5.66 | 1.37E-05 | 4.25 | R | −284 | −263 | gcaaTTCTTTGATTGGCCTTCTTTgtcg | 91 | 4.81 | −7.1 |
| STM1272 | — | yoaG | putative cytoplasmic protein | 6.92 | 7.98 | 1.23E-04 | 2.87 | D | −225 | −204 | cggaAGAGATCATGGTGATCAATGCCggcg | 92 | 8.55 | −10.65 |
| STM1300 | — | STM1300 | putative periplasmic protein | −8.78 | 5.08 | 2.93E-04 | −4.83 | D | −256 | −235 | ggttGTATTTGCGTTTATCAGAATAtgta | 93 | 6.36 | −8.4 |
| STM1301 | L | STM1301 | putative mutator MutT protein | −9.26 | 5.65 | 1.27E-04 | −3.36 | | | | | | | |
| STM1349 | G | pps | phosphoenolpyruvate synthase | −19.01 | 5.69 | 2.28E-06 | −3.45 | D | −58 | −37 | aggaTTGTTCGATGTCCAACAATGGCtcgt | 94 | 5.74 | −7.86 |
| STM1378 | G | pykF | pyruvate kinase I (formerly F), fructose stimulated | 14.46 | 5.51 | 1.36E-05 | 2.55 | | | | | | | |
| STM1489 | H | ynfK | putative dethiobiotin synthase | −11.20 | 5.23 | 7.52E-05 | −8.40 | R | −140 | −119 | aactCAAGCTGATTGCCCTTGCCATAtctt | 95 | 4.73 | −7.04 |

TABLE 3-continued

Differentially expressed genes and the presence/absence of putative FNR-binding motifs in their 5' regions.

| Locus[a] | Cat- ego- ry[b] | STM Gene Name[c] | Function[d] | t value[e] | DF[f] | Prot t[g] | Ratio[h] | Strand[i] | Start[j] | End[k] | Sequence[l] | SEQ ID NO: | Score[m] | In (P)[n] |
|---|---|---|---|---|---|---|---|---|---|---|---|---|---|---|
| STM1498 | C | STM1498 | putative dimethyl sulphoxide reductase | −21.41 | 5.10 | 3.44E−06 | −27.55 | R | −177 | −156 | atacAAATCTGGTGGAAATCGAAAAatct | 96 | 4.87 | −7.15 |
| STM1499 | C | STM1499 | putative dimethyl sulphoxide reductase, chain A1 | −19.08 | 5.35 | 3.98E−06 | −8.27 | D | −101 | −80 | ataaTTTCGTTATAGTTATCAATATAtagc | 97 | 4.38 | −6.78 |
| STM1509 | — | ydfZ | putative cytoplasmic protein | −14.41 | 5.58 | 1.25E−05 | −7.62 | R | −161 | −140 | ccgtGAGCTTGATCAAAAACAAAAAaatt | 98 | 8.84 | −10.98 |
| STM1538 | C | STM1538 | putative hydrogenase-1 large subunit | 11.55 | 5.78 | 3.28E−05 | 3.96 | | | | | | | |
| STM1539 | C | STM1539 | putative hydrogenase-1 small subunit | 8.66 | 5.44 | 2.21E−04 | 3.53 | | | | | | | |
| STM1562 | — | STM1562 | putative periplasmic transport protein | −11.30 | 5.28 | 6.68E−05 | −4.99 | D | −217 | −196 | tgctTTATTCATCAAACATCAAAATCagtc | 99 | 6.71 | −8.73 |
| STM1564 | — | yddX | putative cytoplasmic protein | −10.75 | 8.27 | 3.83E−06 | −2.93 | | | | | | | |
| STM1568 | C | fdnI | formate dehydrogenase-N, cytochrome B556(Fdn) gamma subunit, nitrate-inducible | −28.97 | 6.32 | 5.81E−08 | −3.98 | R | −119 | −98 | tcgcCGGTCTCGATTTACCACTACATCggta | 100 | 7.14 | −9.14 |
| STM1569 | C | fdnH | formate dehydrogenase, iron-sulfur subunit (formate dehydrogenase beta subunit) [EC: 1.2.1.2] | −9.33 | 8.93 | 6.68E−06 | −2.50 | | | | | | | |
| STM1593 | — | srfA | ssrAB activated gene | −5.82 | 6.28 | 9.63E−04 | −2.52 | D | −185 | −164 | accctGATTTAACTTACGTCAAGTGGaaaac | 101 | 5.8 | −7.91 |

TABLE 3-continued

Differentially expressed genes and the presence/absence of putative FNR-binding motifs in their 5' regions.

| Locus[a] | Cat-ego-ry[b] | Name[c] | STM Gene Function[d] | t value[e] | DF[f] | Prot t[g] | Ratio[h] | Strand[i] | Start[j] | End[k] | Sequence[l] | SEQ ID NO: | Score[m] | In (P)[n] |
|---|---|---|---|---|---|---|---|---|---|---|---|---|---|---|
| STM1594 | S | srfB | ssrAB activated gene | −14.70 | 6.14 | 5.14E-06 | −2.88 | D | −58 | −37 | tgccTGATTTATGTTGGTCAATCTGtgtg | 102 | 5.31 | −7.5 |
| STM1626 | N | trg | methyl-accepting chemotaxis protein III, ribose and galactose sensor receptor | −13.30 | 5.46 | 2.28E-05 | −5.72 | | | | | | | |
| STM1640 | S | ydcF | putative inner membrane protein | −11.44 | 5.63 | 4.15E-05 | −5.72 | | | | | | | |
| STM1641 | L | hrpA | helicase, ATP-dependent | −21.19 | 6.25 | 4.68E-07 | −20.97 | R | −217 | −196 | gtgcCCCGTTGCTTGTTGACACTTTAttca | 103 | 4.72 | −7.04 |
| STM1642 | I | acpD | acyl carrier protein phosphodiesterase | −11.32 | 7.81 | 4.05E-06 | −4.01 | D | −107 | −86 | tgaaTAAAGTGTCAACAAGCAACGGGcac | 104 | 4.72 | −7.04 |
| STM1647 | C | ldhA | fermentative D-lactate dehydrogenase, NAD-dependent | −16.29 | 5.95 | 3.65E-06 | −24.42 | D | −139 | −118 | tcatTATATGTATGACTATCAATTATtttt | 105 | 5.05 | −7.29 |
| STM1648 | O | hslJ | heat shock protein hslJ | −8.34 | 5.41 | 2.75E-04 | −5.00 | R | −74 | −53 | ttaaCTATCAGATTACAGAGAATATCaatg | 106 | 4.11 | −6.57 |
| STM1650 | — | | putative reverse transcriptase | −5.38 | 7.56 | 7.97E-04 | −3.52 | | | | | | | |
| STM1651 | C | nifJ | putative pyruvate-flavodoxin oxidoreductase | −8.67 | 6.43 | 8.87E-05 | −4.97 | | | | | | | |
| STM1652 | T | ynaF | putative universal stress protein | −20.67 | 5.01 | 4.81E-06 | −116.15 | R | −282 | −261 | ttatTGAATTAAACGTAACATCTCTtttt | 107 | 4.7 | −7.02 |
| STM1653 | P | | putative membrane transporter of cations | −10.25 | 5.85 | 5.92E-05 | −6.56 | | | | | | | |
| STM1657 | N | | putative methyl-accepting chemotaxis protein | −9.41 | 6.29 | 6.15E-05 | −4.01 | D | −52 | −31 | caaaAATGTTGAGAAATATCAGCGTCagga | 108 | 8.58 | −10.68 |
| STM1658 | S | ydaL | putative Smr domain | −28.29 | 6.75 | 2.87E-08 | −4.01 | | | | | | | |

TABLE 3-continued

Differentially expressed genes and the presence/absence of putative FNR-binding motifs in their 5' regions.

| Locus[a] | Category[b] | Name[c] | STM Gene Function[d] | t value[e] | DF[f] | Prot t[g] | Ratio[h] | Strand[i] | Start[j] | End[k] | Sequence[l] | SEQ ID NO: | Score[m] | In (P)[n] |
|---|---|---|---|---|---|---|---|---|---|---|---|---|---|---|
| STM1659 | L | ogt | O-6-alkylguanine-DNA/cysteine-protein methyltransferase | -6.79 | 6.25 | 4.20E-04 | -2.92 | | | | | | | |
| STM1660 | — | fnr | transcriptional regulation of aerobic, anaerobic respiration, osmotic balance (CRP family) | -8.24 | 5.04 | 4.11E-04 | -6.55 | D | -88 | -67 | tgttAAAATTGACAAATATCAATTACggct | 109 | 11.43 | -14.93 |
| STM1688 | K | pspC | phage shock protein; regulatory gene, activates expression of psp operon with PspB | 11.96 | 6.86 | 7.63E-06 | 3.23 | R | -45 | -24 | gggtGGAATCAATCTGAATAAAAACtatg | 110 | 6.11 | -8.18 |
| STM1706 | J | yciH | putative translation initiation factor SUI1 | 9.58 | 5.71 | 9.91E-05 | 4.32 | | | | | | | |
| STM1732 | M | ompW | outer membrane protein W; colicin S4 receptor; putative transporter | -6.72 | 5.07 | 1.05E-03 | -8.36 | R | -172 | -151 | gttcTAAATTAATCTGGATCAATAAatgtt | 111 | 8.33 | -10.39 |
| STM1746 | — | oppA | ABC superfamily (periplasm), oligopeptide transport protein with chaperone properties | 16.43 | 6.25 | 2.23E-06 | 3.83 | R | -290 | -269 | atttCACATTGTTGATAAGTATTTCattt | 112 | 5.36 | -7.54 |
| STM1767 | T | narL | response regulator in two-component regulatory system with NarX (or NarQ), regulates anaerobic respiration and fermentation (LuxR/UhpA family) | 11.78 | 6.53 | 1.22E-05 | 2.78 | | | | | | | |

TABLE 3-continued

Differentially expressed genes and the presence/absence of putative FNR-binding motifs in their 5' regions.

| Locus[a] | Category[b] | Name[c] | STM Gene Function[d] | t value[e] | DF[f] | Prot t[g] | Ratio[h] | Strand[i] | Start[j] | End[k] | Sequence[i] | SEQ ID NO: | Score[m] | In (P)[n] |
|---|---|---|---|---|---|---|---|---|---|---|---|---|---|---|
| STM1781 | P | ychM | putative SulP family transport protein | -10.77 | 6.07 | 3.49E-05 | -3.33 | R | -230 | -209 | acgaAGAATCGATTTCCGCCATGTTCgagc | 113 | 5.29 | -7.49 |
| STM1795 | E | STM1795 | putative homologue of glutamic dehydrogenase | 12.42 | 5.46 | 3.28E-05 | 5.33 | R | -302 | -281 | acataACATTGATACATGTCTTATCataa | 114 | 6.57 | -8.6 |
| STM1798 | — | ycgR | putative inner membrane protein | -14.17 | 5.94 | 8.40E-06 | -4.09 | D | -267 | -246 | tggcGATAACGCCGGCAATCAAACCAaaaa | 115 | 6.66 | -8.68 |
| STM1803 | E | dadA | D-amino acid dehydrogenase subunit | 10.10 | 8.96 | 3.40E-06 | 3.16 | R | -261 | -240 | cctcCACATTGAACGGCAAAAAATCGgta | 116 | 4.58 | -6.92 |
| STM1831 | G | manY | Sugar Specific PTS family, mannose-specific enzyme IIC | 15.20 | 5.98 | 5.28E-06 | 3.73 | R | -146 | -125 | atccGAAACTGAAAATGATGATTTAattg | 117 | 4.99 | -7.24 |
| STM1832 | G | manZ | Sugar Specific PTS family, mannose-specific enzyme IID | 14.15 | 9.24 | 1.42E-07 | 2.96 | D | -277 | -256 | ttggTTATGCGATGGTTATCAATATGatgc | 118 | 7.21 | -9.2 |
| STM1915 | N | cheZ | chemotactic response; CheY protein phophatase | -9.59 | 5.76 | 9.42E-05 | -3.56 | | | | | | | |
| STM1916 | T | cheY | chemotaxis regulator, transmits chemoreceptor signals to flagelllar motor components | -9.32 | 5.69 | 1.18E-04 | -3.74 | D | -111 | -90 | agcaGATGTTGGCGAAAATCAGTGCCggac | 119 | 8.6 | -10.7 |
| STM1917 | N | cheB | methyl esterase, response regulator for chemotaxis (cheA sensor) | -8.37 | 5.74 | 2.00E-04 | -4.33 | | | | | | | |
| STM1918 | N | cheR | glutamate methyltransferase, response regulator for chemotaxis | -22.41 | 8.99 | 3.40E-09 | -3.32 | | | | | | | |
| STM1919 | N | cheM | methyl accepting chemotaxis protein II, aspartate sensor-receptor | -18.86 | 5.13 | 6.12E-06 | -8.31 | | | | | | | |

TABLE 3-continued

Differentially expressed genes and the presence/absence of putative FNR-binding motifs in their 5' regions.

| Locus[a] | Category[b] | Name[c] | STM Gene Function[d] | t value[e] | DF[f] | Prot t[g] | Ratio[h] | Strand[i] | Start[j] | End[k] | Sequence[l] | SEQ ID NO: | Score[m] | ln (P)[n] |
|---|---|---|---|---|---|---|---|---|---|---|---|---|---|---|
| STM1920 | N | cheW | purine-binding chemotaxis protein; regulation | -14.43 | 5.32 | 1.82E-05 | -4.31 | D | -296 | -275 | gggcATTGTTGTGATCCTGCAAAGCGcggg | 120 | 4.39 | -6.78 |
| STM1921 | N | cheA | sensory histitine protein kinase, transduces signal between chemo-signal receptors and CheB and CheY | -16.27 | 6.02 | 3.32E-06 | -4.67 | D | -39 | -18 | ggatATTAGCGATTTTATCAGACATtttt | 121 | 4.84 | -7.12 |
| STM1922 | N | motB | enables flagellar motor rotation, linking torque machinery to cell wall | -15.03 | 5.33 | 1.43E-05 | -7.00 | R | -177 | -156 | atgcGCCGCCGATTGCCGTGGAATTTggtc | 122 | 5.72 | -7.84 |
| STM1923 | N | motA | proton conductor component of motor, torque generator | -5.97 | 5.07 | 1.80E-03 | -10.82 |  |  |  |  |  |  |  |
| STM1932 | P | ftnB | ferritin-like protein | -21.51 | 5.01 | 3.92E-06 | -21.11 | D | -95 | -74 | tctcGTCTGTCATGCACATCAACACTttct | 123 | 4.24 | -6.67 |
| STM1955 | — | fliZ | putative regulator of FliA | -15.76 | 5.35 | 1.09E-05 | -6.25 | D | -331 | -310 | acagGAAAACCCGTTACATCAACTGCtgga | 124 | 5.78 | -7.9 |
| STM1956 | K | fliA | sigma F (sigma 28) factor of RNA polymerase, transcription of late flagellar genes (class 3a and 3b operons) | -21.86 | 8.81 | 5.60E-09 | -5.96 | R | -64 | -43 | acgcAGGGCTGTTTATCGTGAATTCActgt | 125 | 4.87 | -7.15 |
| STM1960 | N | fliD | flagellar biosynthesis; filament capping protein; enables filament assembly | -15.69 | 6.81 | 1.35E-06 | -4.45 | R | -82 | -61 | cttaACTACTGTTTGCAATCAAAAGgaag | 126 | 4.63 | -6.97 |
| STM1961 | O | fliS | flagellar biosynthesis; repressor of class | -9.80 | 5.27 | 1.40E-04 | -5.10 | R | -231 | -210 | acgcCACGCTGAAAAGCCTGACAAAAcagt | 127 | 4.08 | -6.56 |

TABLE 3-continued

Differentially expressed genes and the presence/absence of putative FNR-binding motifs in their 5' regions.

| Locus[a] | Cat-ego-ry[b] | Name[c] | STM Gene Function[d] | t value[e] | DF[f] | Prot t[g] | Ratio[h] | Strand[i] | Start[j] | End[k] | Sequence[l] | SEQ ID NO: | Score[m] | In (P)[n] |
|---|---|---|---|---|---|---|---|---|---|---|---|---|---|---|
| STM1962 | – | | 3a and 3b operons (RflA activity) | −7.66 | 5.16 | 5.25E-04 | −6.03 | | | | | | | |
| STM1971 | N | fliT | flagellar biosynthesis; possible export chaperone for FliD | −8.61 | 6.32 | 1.01E-04 | −2.94 | | | | | | | |
| STM1973 | N | fliH | flagellar biosynthesis; possible export of flagellar proteins | −7.71 | 6.36 | 1.88E-04 | −4.27 | | | | | | | |
| STM1975 | N | fliJ | flagellar fliJ protein | −8.94 | 5.55 | 1.68E-04 | −2.79 | | | | | | | |
| STM1976 | N | fliL | flagellar biosynthesis | −9.19 | 5.26 | 1.95E-04 | −3.07 | R | −161 | −140 | aacaAAAACTGATTGCCGCCATTAAAgaga | 128 | 5.62 | −7.76 |
| STM1978 | N | fliM | flagellar biosynthesis, component of motor switch and energizing | −5.21 | 6.02 | 1.98E-03 | −2.76 | | | | | | | |
| STM2059 | S | fliO | flagellar biosynthesis | 8.96 | 6.90 | 4.79E-05 | 2.75 | | | | | | | |
| STM2183 | F | yeeX | putative cytoplasmic protein | −17.85 | 5.47 | 4.66E-06 | −7.71 | R | −157 | −136 | atttTTCATTGAAGTTTCACAGTTGcata | 129 | 5.31 | −7.51 |
| STM2186 | E | cdd | cytidine/deoxycytidine deaminase | −15.60 | 5.64 | 7.43E-06 | −4.18 | D | −269 | −248 | cttcTTTTTATCGTTAATCTATTAttat | 130 | 5.46 | −7.63 |
| STM2187 | F | STM2186 | putative NADPH-dependent glutamate synthase beta chain or related oxidoreductase | −15.69 | 5.44 | 9.74E-06 | −4.05 | | | | | | | |
| STM2277 | F | yeiA | putative dihydropyrimidine dehydrogenase | 26.74 | 5.26 | 8.07E-07 | 11.15 | D | −60 | −39 | ggtaGAAAACCACATGAATCAGAGTCtgct | 131 | 4.2 | −6.64 |
| | | nrdA | ribonucleoside diphosphate reductase 1, alpha subunit | | | | | | | | | | | |

TABLE 3-continued

Differentially expressed genes and the presence/absence of putative FNR-binding motifs in their 5' regions.

| Locus[a] | Category[b] | Name[c] | STM Gene Function[d] | t value[e] | DF[f] | Prot t[g] | Ratio[h] | Strand[i] | Start[j] | End[k] | Sequence[i] | SEQ ID NO: | Score[m] | ln (P)[n] |
|---|---|---|---|---|---|---|---|---|---|---|---|---|---|---|
| STM2278 | F | nrdB | ribonucleoside-diphosphate reductase 1, beta subunit | 29.51 | 5.69 | 1.92E-07 | 9.57 | D | -68 | -47 | tcccATAAAGGATTCACTTCAATGGCatac | 132 | 6.02 | -8.11 |
| STM2279 | C | yfaE | putative ferredoxin | 6.33 | 5.30 | 1.17E-03 | 3.37 | R | -297 | -276 | acggTTCGATGATCGCCTGAATAAgata | 133 | 5.02 | -7.27 |
| STM2280 | G | STM2280 | putative permease | 11.04 | 6.42 | 2.06E-05 | 4.32 | | | | | | | |
| STM2287 | — | STM2287 | putative cytoplasmic protein | 4.59 | 6.33 | 3.24E-03 | 3.46 | R | -279 | -258 | ggggATAACTGAATATCCCAATATaatt | 134 | 4.46 | -6.84 |
| STM2314 | T | STM2314 | putative chemotaxis signal transduction protein | -25.76 | 5.48 | 6.21E-07 | -6.99 | | | | | | | |
| STM2315 | R | yfbK | putative von Willebrand factor, vWF type A domain | -15.60 | 9.01 | 7.88E-08 | -2.84 | | | | | | | |
| STM2316 | — | nuoN | NADH dehydrogenase I chain N | 8.29 | 6.13 | 1.50E-04 | 2.67 | R | -334 | -313 | tggtGCCGGTGATTACCGTGATCTCCacct | 135 | 4.26 | -6.69 |
| STM2318 | C | nuoL | NADH dehydrogenase I chain L | 8.02 | 7.14 | 8.05E-05 | 2.54 | R | -261 | -240 | tgttTATGCTGATTGGGCTGAAATCatga | 136 | 5.57 | -7.71 |
| STM2320 | C | nuoJ | NADH dehydrogenase I chain J [EC: 1.6.5.3] | 11.27 | 6.55 | 1.58E-05 | 2.54 | | | | | | | |
| STM2324 | C | nuoF | NADH dehydrogenase I chain F | 9.85 | 7.93 | 1.01E-05 | 2.60 | | | | | | | |
| STM2325 | C | nuoE | NADH dehydrogenase I chain E | 8.07 | 8.32 | 3.28E-05 | 2.65 | | | | | | | |
| STM2326 | C | nuoC | NADH dehydrogenase I chain C, D | 22.56 | 6.50 | 2.04E-07 | 3.34 | | | | | | | |

TABLE 3-continued

Differentially expressed genes and the presence/absence of putative FNR-binding motifs in their 5' regions.

| Locus[a] | Cat-ego-ry[b] | Name[c] | STM Gene Function[d] | t value[e] | DF[f] | Prot t[g] | Ratio[h] | Strand[i] | Start[j] | End[k] | Sequence[l] | SEQ ID NO: | Score[m] | ln (P)[n] |
|---|---|---|---|---|---|---|---|---|---|---|---|---|---|---|
| STM2327 | C | nuoB | NADH dehydrogenase I chain B [EC: 1.6.5.3] | 11.71 | 6.20 | 1.86E-05 | 2.52 | | | | | | | |
| STM2334 | R | yfbT | putative phosphatase | 18.20 | 6.34 | 1.03E-06 | 3.49 | R | -76 | -55 | gagcGCGAATGAAATCAATCAAATCattaa | 137 | 5.55 | -7.7 |
| STM2335 | S | yfbU | putative cytoplasmic protein | 6.74 | 5.61 | 6.87E-04 | 3.39 | | | | | | | |
| STM2337 | C | ackA | acetate kinase A (propionate kinase 2) | -16.97 | 6.34 | 1.60E-06 | -3.51 | R | -147 | -126 | tcctGCGCATGATGTTAATCATAAATgtca | 138 | 4.76 | -7.07 |
| STM2338 | C | pta | phosphotransacetylase | -6.43 | 5.94 | 6.96E-04 | -3.17 | | | | | | | |
| STM2340 | G | STM2340 | putative transketolase | 11.33 | 5.19 | 7.42E-05 | 6.60 | D | -82 | -61 | gctcAATGAGGCCATTCATCACTGGaggt | 139 | 4.18 | -6.62 |
| STM2341 | G | STM2341 | putative transketolase | 23.38 | 5.42 | 1.19E-06 | 6.47 | | | | | | | |
| STM2342 | S | STM2342 | putative inner membrane protein | 9.98 | 5.52 | 9.77E-05 | 5.22 | R | -276 | -255 | aaaaAGTATTAAAGAACTCAATATTgacg | 140 | 6.82 | -8.83 |
| STM2343 | G | STM2343 | putative cytoplasmic protein | 10.35 | 6.09 | 4.30E-05 | 3.34 | D | -64 | -43 | tttaAAAGGTGACAATAATGAAAATcatgg | 141 | 4.64 | -6.97 |
| STM2409 | F | nupC | NUP family, nucleoside transport | -15.30 | 5.45 | 1.09E-05 | -3.91 | D | -347 | -326 | gtttATTGATAATGATTATCAAGTGCattt | 142 | 5.87 | -7.97 |
| STM2454 | K | eutR | putative regulator ethanolamine operon (AraC/XylS family) | -12.08 | 5.35 | 4.34E-05 | -5.13 | | | | | | | |
| STM2455 | Q | eutK | putative carboxysome structural protein, ethanolamine utilization | -9.27 | 5.21 | 1.97E-04 | -6.77 | D | -61 | -40 | aacgGAGGCTGCCAATGATCATGCCctgg | 143 | 4.45 | -6.83 |
| STM2456 | E | eutL | putative carboxysome structural protein, | -9.22 | 5.22 | 1.99E-04 | -6.68 | | | | | | | |

TABLE 3-continued

Differentially expressed genes and the presence/absence of putative FNR-binding motifs in their 5' regions.

| Locus[a] | Category[b] | Name[c] | STM Gene Function[d] | t value[e] | DF[f] | Prot t[g] | Ratio[h] | Strand[i] | Start[j] | End[k] | Sequence[l] | SEQ ID NO: | Score[m] | In (P)[n] |
|---|---|---|---|---|---|---|---|---|---|---|---|---|---|---|
| STM2457 | E | | ethanolamine utilization | -16.21 | 5.56 | 6.85E-06 | -7.07 | | | | | | | |
| STM2458 | E | eutC | ethanolamine ammonia-lyase, light chain | -17.30 | 5.54 | 4.94E-06 | -6.33 | D | -315 | -294 | ccgcATTACTCACGGTCATCAACGCGctga | 144 | 5.38 | -7.56 |
| STM2459 | E | eutB | ethanolamine ammonia-lyase, heavy chain | -19.26 | 5.16 | 5.24E-06 | -6.17 | | | | | | | |
| STM2460 | E | eutA | CPPZ-55 prophage; chaperonin in ethanolamine utilization | -17.75 | 5.32 | 6.09E-06 | -6.29 | | | | | | | |
| STM2462 | E | eutH | putative transport protein, ethanolamine utilization | -7.74 | 5.05 | 5.52E-04 | -7.30 | | | | | | | |
| STM2463 | E | eutJ | paral putative heatshock protein (Hsp70) | -18.52 | 5.34 | 4.73E-06 | -7.02 | R | -64 | -43 | aaatAGGATTGAACATCATGAATCAAcagg | 145 | 4.88 | -7.15 |
| STM2464 | C | eutE | putative aldehyde oxidoreductase in ethanolamine utilization | -14.11 | 5.14 | 2.65E-05 | -8.00 | D | -194 | -173 | tggaAGAAGTGTTCCCGATCAGCTTCaaag | 146 | 5.21 | -7.42 |
| STM2465 | Q | eutN | putative detox protein in ethanolamine utilization | -28.26 | 5.11 | 8.21E-07 | -11.02 | R | -250 | -229 | ctatCCGCTGTTGGGCCGCTAATTCaggg | 147 | 4.58 | -6.93 |
| STM2466 | Q | eutM | putative detox protein in ethanolamine utilization | -15.83 | 5.11 | 1.53E-05 | -10.36 | | | | | | | |
| | C | eutD | putative phosphotransacetylase in ethanolamine utilization | | | | | | | | | | | |

TABLE 3-continued

Differentially expressed genes and the presence/absence of putative FNR-binding motifs in their 5' regions.

| Locus[a] | Category[b] | Name[c] | STM Gene Function[d] | t value[e] | DF[f] | Prot t[g] | Ratio[h] | Strand[i] | Start[j] | End[k] | Sequence[l] | SEQ ID NO: | Score[m] | In (P)[n] |
|---|---|---|---|---|---|---|---|---|---|---|---|---|---|---|
| STM2467 | E | eutT | putative cobalamin adenosyltransferase, ethanolamine utilization | −16.88 | 5.92 | 3.13E-06 | −6.59 | R | −237 | −216 | cgtgGAcGCTGAACTACGACGAAATCgaca | 148 | 6.89 | −8.9 |
| STM2468 | E | eutQ | putative ethanolamine utilization protein | −18.58 | 5.26 | 5.33E-06 | −7.60 | | | | | | | |
| STM2469 | E | eutP | putative ethanolamine utilization protein | −20.06 | 5.13 | 4.47E-06 | −9.38 | R | −247 | −226 | aaacGGCGATGATCGCTGGCCGATTTAgcga | 149 | 4.71 | −7.03 |
| STM2470 | E | eutS | putative carboxysome structural protein, ethanol utilization | −10.43 | 5.05 | 1.32E-04 | −13.70 | R | −154 | −133 | ttctCTTAGTGATCTACCTCACCTTTtaca | 150 | 5.95 | −8.05 |
| STM2479 | E | aegA | putative oxidoreductase | −7.82 | 7.39 | 7.90E-05 | −3.37 | R | −187 | −166 | gaaaTAAATTGATCTGCCACAGGTTCtgga | 151 | 7.26 | −9.26 |
| STM2530 | C | STM2530 | putative anaerobic dimethylsulfoxide reductase | −10.14 | 7.00 | 1.96E-05 | −3.67 | D | −158 | −137 | ttatGAATTCATTTAATTTAAAGTaatg | 152 | 6.79 | −8.8 |
| STM2556 | C | hmpA | dihydropteridine reductase 2 and nitric oxide dioxygenase activity | 15.99 | 5.95 | 4.09E-06 | 3.01 | R | −95 | −74 | agatGCATTTGATATACATCATTAGAtttt | 153 | 6.24 | −8.3 |
| STM2558 | E | cadB | APC family, lysine/cadaverine transport protein | −6.65 | 5.19 | 1.01E-03 | −6.43 | D | −219 | −198 | tatgTTAATTCAAAAAATCAATCTAtcag | 154 | 6.78 | −8.8 |
| STM2559 | E | cadA | lysine decarboxylase 1 | −10.67 | 5.18 | 1.02E-04 | −5.58 | R | −221 | −200 | tcgtCAGTCTGATCATCCTGATGTTCtacg | 155 | 5.74 | −7.86 |
| STM2646 | R | yfiD | putative formate acetyltransferase | −26.43 | 5.69 | 3.54E-07 | −5.08 | D | −179 | −158 | ggttTTTATTGATTTAAATCAAGAGAtgaa | 156 | 10.76 | −13.71 |
| STM2733 | − | STM2733 | Fels-2 prophage: similar to E. coli retron Ec67 | −5.44 | 8.92 | 4.26E-04 | −2.72 | | | | | | | |
| STM2786 | S | STM2786 | tricarboxylic transport | 19.84 | 5.84 | 1.38E-06 | 8.21 | | | | | | | |

TABLE 3-continued

Differentially expressed genes and the presence/absence of putative FNR-binding motifs in their 5' regions.

| Locus[a] | Cat-ego-ry[b] | Name[c] | STM Gene Function[d] | t value[e] | DF[f] | Prot t[g] | Ratio[h] | Strand[i] | Start[j] | End[k] | Sequence[l] | SEQ ID NO: | Score[m] | In (P)[n] |
|---|---|---|---|---|---|---|---|---|---|---|---|---|---|---|
| STM2787 | — | STM2787 | tricarboxylic transport | 10.54 | 9.96 | 1.01E−06 | 6.89 | | | | | | | |
| STM2788 | S | STM2788 | tricarboxylic transport | 11.85 | 5.46 | 4.19E−05 | 3.46 | R | −107 | −86 | ttgaCCGGCTGCTTGATGTCACCTTAcctc | 157 | 4.26 | −6.68 |
| STM2795 | S | ygaU | putative LysM domain | −3.59 | 5.59 | 1.31E−02 | −2.98 | D | −55 | −34 | aggtGAATATGGGACTTTCAATTTTgtaa | 158 | 5.43 | −7.6 |
| STM2851 | C | hycC | hydrogenase 3, membrane subunit (part of FHL complex) | −5.41 | 8.55 | 5.07E−04 | −3.49 | | | | | | | |
| STM2855 | O | hypB | hydrogenase-3 accessory protein, assembly of metallocenter | −14.31 | 6.06 | 6.74E−06 | −3.12 | R | −143 | −122 | cataGAGATTGATGAAACTGAAGATTaatg | 159 | 9.23 | −11.47 |
| STM2856 | O | hypC | putative hydrogenase expression/formation protein | −9.09 | 6.18 | 8.40E−05 | −2.56 | | | | | | | |
| STM2857 | O | hypD | putative hydrogenase expression/formation protein | −8.01 | 5.29 | 3.76E−04 | −2.97 | | | | | | | |
| STM2871 | U | prgK | cell invasion protein; lipoprotein, may link inner and outer membranes | −15.27 | 7.06 | 1.15E−06 | −3.25 | | | | | | | |
| STM2872 | — | prgJ | cell invasion protein; cytoplasmic | −9.60 | 5.35 | 1.43E−04 | −4.65 | R | −344 | −323 | agccCACTTTAATTTAACGTAAATAAggaa | 160 | 5.69 | −7.82 |
| STM2873 | — | prgI | cell invasion protein; cytoplasmic | −12.42 | 5.80 | 2.13E−05 | −4.16 | R | −83 | −62 | agccCACTTTAATTTAACGTAAATAAggaa | 161 | 5.69 | −7.82 |
| STM2874 | — | prgH | cell invasion protein | −16.99 | 6.31 | 1.65E−06 | −3.85 | | | | | | | |

TABLE 3-continued

Differentially expressed genes and the presence/absence of putative FNR-binding motifs in their 5' regions.

| Locus[a] | Cat-egory[b] | Name[c] | STM Gene Function[d] | t value[e] | DF[f] | Prot t[g] | Ratio[h] | Strand[i] | Start[j] | End[k] | Sequence[l] | SEQ ID NO: | Score[m] | In (P)[n] |
|---|---|---|---|---|---|---|---|---|---|---|---|---|---|---|
| STM2877 | M | iagB | cell invasion protein | -4.52 | 5.49 | 5.01E-03 | -3.55 | R | -86 | -65 | ccgcTTGATTAAATTACGGTAAATCtgag | 162 | 4.68 | -7 |
| STM2886 | R | sicA | surface presentation of antigens; secretory proteins | -10.24 | 5.19 | 1.24E-04 | -2.80 | D | -57 | -36 | ggagTAAGTAATGGATTATCAAAATAatgt | 163 | 4.34 | -6.75 |
| STM2890 | U | spaP | surface presentation of antigens; secretory proteins | -5.39 | 5.53 | 2.17E-03 | -4.27 | D | -88 | -67 | cttaGCGTTGAGATCCATGAATGGCtgag | 164 | 4.61 | -6.95 |
| STM2891 | N | spaO | surface presentation of antigens; secretory proteins | -8.43 | 5.86 | 1.72E-04 | -3.67 | | | | | | | |
| STM2892 | — | invJ | surface presentation of antigens; secretory proteins | -7.06 | 5.22 | 7.34E-04 | -5.51 | D | -239 | -218 | tttaGAACTCCAGATTATACAAATTCagga | 165 | 4.22 | -6.66 |
| STM2893 | — | invI | surface presentation of antigens; secretory proteins | -12.02 | 5.46 | 3.91E-05 | -4.44 | R | -190 | -169 | gcttTTCATTGACTTGGGAGAATATCgtcc | 166 | 6.09 | -8.16 |
| STM2894 | N | invC | surface presentation of antigens; secretory proteins | -6.62 | 6.04 | 5.54E-04 | -2.79 | | | | | | | |
| STM2895 | — | invB | surface presentation of antigens; secretory proteins | -10.44 | 5.50 | 7.85E-05 | -3.88 | R | -267 | -246 | ccgcTAATTTGATGGATCTCATTACActta | 167 | 8.41 | -10.48 |
| STM2896 | U | invA | invasion protein | -6.84 | 5.81 | 5.50E-04 | -3.34 | | | | | | | |
| STM2897 | — | invE | invasion protein | -5.52 | 6.12 | 1.40E-03 | -3.09 | R | -29 | -8 | tccgGTATTTCATTTTCCAGATATTgtcc | 168 | 4.35 | -6.76 |
| STM2898 | N | invG | invasion protein; outer membrane | -6.82 | 5.89 | 5.30E-04 | -3.48 | D | -126 | -105 | cacaTTTTTCTAGTGAGATCAAAGAGctga | 169 | 7.49 | -9.49 |
| STM2899 | K | invF | invasion protein | -5.45 | 5.63 | 1.95E-03 | -3.57 | | | | | | | |
| STM2983 | — | ygdI | putative lipoprotein | -7.97 | 6.00 | 2.09E-04 | -3.64 | | | | | | | |

TABLE 3-continued

Differentially expressed genes and the presence/absence of putative FNR-binding motifs in their 5' regions.

| Locus[a] | Cat-ego-ry[b] | STM Gene Name[c] | Function[d] | t value[e] | DF[f] | Prot t[g] | Ratio[h] | Strand[i] | Start[j] | End[k] | Sequence[l] | SEQ ID NO: | Score[m] | In (P)[n] |
|---|---|---|---|---|---|---|---|---|---|---|---|---|---|---|
| STM3019 | I | yqeF | putative acetyl-CoA acetyltransferase | 10.03 | 6.84 | 2.46E-05 | 2.58 | R | -249 | -228 | ctatTGATTTGCTGTGGAACAAGAAAacgc | 170 | 4.54 | -6.9 |
| STM3131 | S | STM3131 | putative cytoplasmic protein | -17.74 | 9.67 | 1.07E-08 | -7.24 | R | -77 | -56 | actgCCACCTGATCAACAAGGAGATAaatc | 171 | 5.09 | -7.32 |
| STM3136 | G | STM3136 | putative D-mannonate oxidoreductase | 9.94 | 5.61 | 8.96E-05 | 2.88 | | | | | | | |
| STM3138 | N | STM3138 | putative methyl-accepting chemotaxis protein | -8.98 | 5.43 | 1.84E-04 | -4.76 | | | | | | | |
| STM3155 | – | STM3155 | putative cytoplasmic protein | -7.23 | 7.42 | 1.31E-04 | -2.81 | R | -78 | -57 | gtatACCACTGATCGTAAAGGATATTtagt | 172 | 7.28 | -9.28 |
| STM3216 | N | STM3216 | putative methyl-accepting chemotaxis protein | -15.35 | 7.19 | 9.30E-07 | -3.37 | R | -280 | -259 | tctaCCTATTAATAGGTATAAACTCAgtta | 173 | 5.59 | -7.73 |
| STM3217 | T | aer | aerotaxis sensor receptor, senses cellular redox state or proton motive force | -12.23 | 5.32 | 4.29E-05 | -4.77 | D | -238 | -217 | aaagGTTGTCCACGCTAAACAATTTCataa | 174 | 8.02 | -10.04 |
| STM3225 | E | ygjU | putative dicarboxylate permease | 17.69 | 9.71 | 1.04E-08 | 3.68 | | | | | | | |
| STM3238 | S | yhaN | putative inner membrane protein | -6.92 | 6.10 | 4.20E-04 | -3.18 | R | -146 | -125 | aaggCGCTTCGTTCGTTGTACCTGATTATTatta | 175 | 4.55 | -6.9 |
| STM3240 | E | tdcG | L-serine deaminase | -16.72 | 5.57 | 5.68E-06 | -4.80 | R | -249 | -228 | ggatGCGATTGAACATCCGGAAAACTaccc | 176 | 6.02 | -8.11 |
| STM3241 | C | tdcE | pyruvate formate-lyase 4/2-ketobutyrate formate-lyase | -9.34 | 10.00 | 2.95E-06 | -2.66 | | | | | | | |
| STM3242 | C | tdcD | propionate kinase/acetate kinase II, anaerobic | -14.83 | 7.09 | 1.35E-06 | -4.10 | R | -147 | -126 | tgacCATCCTGAATATTGTCTACAAAttgt | 177 | 4.53 | -6.89 |

TABLE 3-continued

Differentially expressed genes and the presence/absence of putative FNR-binding motifs in their 5' regions.

| Locus[a] | Cat-ego-ry[b] | Name[c] | STM Gene Function[d] | t value[e] | DF[f] | Prot t[g] | Ratio[h] | Strand[i] | Start[j] | End[k] | Sequence[l] | SEQ ID NO: | Score[m] | In (P)[n] |
|---|---|---|---|---|---|---|---|---|---|---|---|---|---|---|
| STM3245 | K | tdcA | transcriptional activator of tdc operon (LysR family) | -17.03 | 5.41 | 6.59E-06 | -6.04 | D | -239 | -218 | cctgTTTTTGATTGAAATCAGGCTAagtt | 178 | 8.48 | -10.57 |
| STM3248 | I | garR | tartronate semialdehyde reductase (TSAR) | 15.78 | 5.93 | 4.53E-06 | 4.16 | | | | | | | |
| STM3273 | I | yhbT | putative lipid carrier protein | -9.33 | 5.49 | 1.43E-04 | -2.71 | D | -237 | -216 | acgcAAAATTGTTAACGAACAGGGATttta | 179 | 5.52 | -7.68 |
| STM3274 | O | yhbU | putative protease | -10.06 | 5.51 | 9.38E-05 | -10.68 | R | -103 | -82 | taaaATCCCTGTTCGTTAACAATTTTgcgt | 180 | 5.52 | -7.68 |
| STM3275 | — | yhbV | putative protease | -13.35 | 5.95 | 1.16E-05 | -10.88 | | | | | | | |
| STM3334 | F | STM3334 | putative cytosine deaminase | -8.46 | 6.65 | 8.47E-05 | -2.58 | D | -277 | -256 | agtgATTATTGCCGACTATCTGTTGAaccg | 181 | 4 | -6.5 |
| STM3338 | G | nanT | MFS family, sialic acid transport protein | -19.92 | 5.67 | 1.83E-06 | -3.02 | | | | | | | |
| STM3545 | R | yhhX | putative oxidoreductase | 14.13 | 5.91 | 8.84E-06 | 3.21 | | | | | | | |
| STM3547 | — | STM3547 | putative transcriptional regulator of sugar metabolism | 54.21 | 5.60 | 7.77E-09 | 6.06 | | | | | | | |
| STM3548 | — | STM3548 | putative cytoplasmic protein | 40.36 | 5.24 | 9.82E-08 | 9.29 | R | -327 | -306 | gcttGCTTATGATGCACACAATTCAtcta | 182 | 4.98 | -7.24 |
| STM3549 | S | STM3549 | putative inner membrane protein | 13.96 | 5.28 | 2.25E-05 | 7.22 | | | | | | | |
| STM3550 | R | STM3550 | putative phosphotriesterase | 22.45 | 5.17 | 2.34E-06 | 7.40 | | | | | | | |
| STM3576 | P | zntA | P-type ATPase family, Pb/Cd/Zn/Hg transporting ATPase [EC: 3.6.3.3 3.6.3.5] | 9.90 | 5.54 | 9.92E-05 | 2.55 | R | -261 | -240 | cgacGCTGCTGTTCATCGGCAATATCgtct | 183 | 5.02 | -7.27 |

TABLE 3-continued

Differentially expressed genes and the presence/absence of putative FNR-binding motifs in their 5' regions.

| Locus[a] | Category[b] | Name[c] | STM Gene Function[d] | t value[e] | DF[f] | Prot t[g] | Ratio[h] | Strand[i] | Start[j] | End[k] | Sequence[l] | SEQ ID NO: | Score[m] | In (P)[n] |
|---|---|---|---|---|---|---|---|---|---|---|---|---|---|---|
| STM3577 | N | tcp | methyl-accepting transmembrane citrate/phenol chemoreceptor | -22.22 | 5.71 | 9.23E-07 | -5.64 | R | -126 | -105 | agcgTGATTTGATGTAAGGTTAATTTttat | 184 | 6.53 | -8.56 |
| STM3598 | E | | putative L-asparaginase | -8.27 | 6.47 | 1.13E-04 | -3.70 | | | | | | | |
| STM3599 | R | STM3599 | putative inner membrane protein | -7.19 | 5.11 | 7.38E-04 | -9.14 | D | -108 | -87 | cacaATAGGTTACGTCCCTCAATGTAaagc | 185 | 4.29 | -6.71 |
| STM3600 | G | STM3600 | putative sugar kinases, ribokinase family | -9.76 | 5.07 | 1.77E-04 | -12.63 | R | -322 | -301 | aacgCCGTTAAACTTCCTGAAAAAAAtatg | 186 | 5 | -7.25 |
| STM3601 | M | STM3601 | putative phosphosugar isomerase | -26.75 | 5.09 | 1.12E-06 | -11.94 | R | -266 | -245 | cgcaACAGTTGATTGTCGGCGATAAaatac | 187 | 7.59 | -9.59 |
| STM3611 | T | yhjH | putative Diguanylate cyclase/phosphodiesterase domain 3 | -16.54 | 5.11 | 1.23E-05 | -7.89 | | | | | | | |
| STM3626 | E | dppF | ABC superfamily (atp_bind), dipeptide transport protein | 9.03 | 5.90 | 1.14E-04 | 5.86 | | | | | | | |
| STM3627 | E | dppD | ABC superfamily (atp_bind), dipeptide transport protein | 8.88 | 5.24 | 2.36E-04 | 7.65 | D | -45 | -24 | ggcgTTATTAAATGTAGATCAATTATcggt | 188 | 8.18 | -10.23 |
| STM3628 | E | dppC | ABC superfamily (membrane), dipeptide transport protein 2 | 16.86 | 5.71 | 4.35E-06 | 4.09 | | | | | | | |
| STM3629 | E | dppB | ABC superfamily (membrane), dipeptide transport protein 1 | 11.76 | 5.16 | 6.34E-05 | 12.45 | D | -55 | -34 | ttcgGGTTATGTTGCAGTTCATTCTCcgac | 189 | 4.22 | -6.66 |
| STM3630 | E | dppA | ABC superfamily (peri_perm), | 9.06 | 5.06 | 2.56E-04 | 9.90 | | | | | | | |

TABLE 3-continued

Differentially expressed genes and the presence/absence of putative FNR-binding motifs in their 5' regions.

| Locus[a] | Category[b] | Name[c] | STM Gene Function[d] | t value[e] | DF[f] | Prot t[g] | Ratio[h] | Strand[i] | Start[j] | End[k] | Sequence[l] | SEQ ID NO: | Score[m] | In (P)[n] |
|---|---|---|---|---|---|---|---|---|---|---|---|---|---|---|
| STM3690 | – | STM3690 | putative inner membrane lipoprotein dipeptide transport protein | −15.85 | 9.97 | 2.15E-08 | −5.67 | R | −305 | −284 | ccgcAAAATTAAATAACATTATCATCcctg | 190 | 4.96 | −7.22 |
| STM3692 | C | lldP | LctP transporter, L-lactate permease | 9.84 | 5.02 | 1.81E-04 | 16.00 | D | −160 | −139 | tgtcATTATCCATACACAACAATATTggca | 191 | 6.37 | −8.41 |
| STM3693 | K | lldR | putative transcriptional regulator for lct operon (GntR family) | 12.30 | 5.04 | 5.98E-05 | 30.60 | | | | | | | |
| STM3694 | C | lldD | L-lactate dehydrogenase | 27.93 | 5.02 | 1.05E-06 | 28.33 | | | | | | | |
| STM3695 | J | yibK | putative tRNA/rRNA methyltransferase | 9.64 | 9.95 | 2.31E-06 | 2.95 | | | | | | | |
| STM3708 | E | tdh | threonine 3-dehydrogenase | 7.11 | 6.53 | 2.66E-04 | 3.16 | | | | | | | |
| STM3709 | H | kbl | 2-amino-3-ketobutyrate CoA ligase (glycine acetyltransferase) | 12.63 | 6.75 | 6.02E-06 | 2.86 | D | −298 | −277 | taacGATATTGTGCCGATAAAGCCCgcgc | 192 | 5.12 | −7.34 |
| STM3750 | G | yicJ | putative GPH family transport protein | −13.67 | 7.06 | 2.44E-06 | −2.67 | | | | | | | |
| STM3801 | G | dsdX | putative Gnt family transport protein | 14.70 | 7.68 | 6.70E-07 | 3.42 | R | −22 | −1 | gcacGCTGCTGATCAGCATCGTGTT | 193 | 5.63 | −7.77 |
| STM3802 | E | dsdA | D-serine deaminase (dehydratase) | 17.71 | 5.05 | 9.69E-06 | 7.90 | | | | | | | |
| STM3808 | – | ibpB | small heat shock protein | 6.72 | 5.53 | 7.44E-04 | 2.85 | | | | | | | |
| STM3820 | P | STM3820 | putative cytochrome c peroxidase | −12.03 | 6.07 | 1.83E-05 | −5.87 | D | −165 | −144 | tgtaATTATTGATACCAATCAATATCcatg | 194 | 11 | −14.14 |

TABLE 3-continued

Differentially expressed genes and the presence/absence of putative FNR-binding motifs in their 5' regions.

| Locus[a] | Category[b] | Name[c] | STM Gene Function[d] | t value[e] | DF[f] | Prot t[g] | Ratio[h] | Strand[i] | Start[j] | End[k] | Sequence[i] | SEQ ID NO: | Score[m] | In (P)[n] |
|---|---|---|---|---|---|---|---|---|---|---|---|---|---|---|
| STM3831 | R | yidA | putative hydrolase of the HAD superfamily | 19.09 | 7.62 | 1.03E-07 | 4.38 | D | -220 | -199 | acggTATTTCTGTTTGATTAATGAGgtta | 195 | 7.22 | -9.21 |
| STM3861 | M | glmS | L-glutamine:D-fructose-6-phosphate aminotransferase | 8.04 | 6.11 | 1.80E-04 | 2.89 | R | -24 | -3 | cgcgCAGCGTGATGTAGCTGAAATCCt | 196 | 4.19 | -6.63 |
| STM3862 | M | glmU | N-acetyl glucosamine-1-phosphate uridyltransferase and glucosamine-1-phosphate acetyl transferase | 7.97 | 5.70 | 2.67E-04 | 2.78 | | | | | | | |
| STM3909 | E | ilvC | ketol-acid reductoisomerase | 10.62 | 5.70 | 5.68E-05 | 3.38 | | | | | | | |
| STM4004 | H | hemN | O2-independent coproporphyrinogen III oxidase | 10.06 | 5.66 | 8.07E-05 | 3.82 | | | | | | | |
| STM4007 | E | glnA | glutamine synthetase | 19.35 | 5.32 | 3.91E-06 | 5.97 | | | | | | | |
| STM4034 | O | fdhE | putative formate dehydrogenase formation protein ? Mn_fn | 9.93 | 6.01 | 5.99E-05 | 3.12 | | | | | | | |
| STM4035 | C | fdoI | formate dehydrogenase, cytochrome B556 (FDO) subunit | 8.84 | 5.80 | 1.40E-04 | 3.60 | | | | | | | |
| STM4036 | C | fdoH | formate dehydrogenase-O, Fe-S subunit | 21.65 | 8.93 | 5.02E-09 | 2.85 | | | | | | | |
| STM4037 | C | fdoG | formate dehydrogenase | 7.75 | 5.52 | 3.62E-04 | 2.73 | | | | | | | |
| STM4062 | G | pfkA | 6-phosphofructokinase I | 12.62 | 9.16 | 4.23E-07 | 2.97 | R | -181 | -160 | cattTGGCCTGACCTGAATCAATTCAgcag | 197 | 5.19 | -7.4 |

TABLE 3-continued

Differentially expressed genes and the presence/absence of putative FNR-binding motifs in their 5' regions.

| Locus[a] | Cat-ego-ry[b] | Name[c] | STM Gene Function[d] | t value[e] | DF[f] | Prot t[g] | Ratio[h] | Strand[i] | Start[j] | End[k] | Sequence[l] | SEQ ID NO: | Score[m] | In (P)[n] |
|---|---|---|---|---|---|---|---|---|---|---|---|---|---|---|
| STM4078 | G | yneB | putative fructose-1,6-bisphosphate aldolase | 15.91 | 7.71 | 3.57E-07 | 2.57 | R | -51 | -30 | aagaATGGCTGATTTAGATGATATTAaaga | 198 | 5.53 | -7.68 |
| STM4085 | G | glpX | unknown function in glycerol metabolism | 6.62 | 5.50 | 8.16E-04 | 3.20 | R | -60 | -39 | ctacGAGTTTGTTATGAGACCAGAACttgc | 199 | 5.56 | -7.71 |
| STM4109 | G | talC | putative transaldolase | 19.34 | 8.13 | 4.38E-08 | 4.72 | D | -221 | -200 | tcatTATGCTGACGCTTAACAACACgccg | 200 | 4.79 | -7.09 |
| STM4110 | G | ptsA | General PTS family, enzyme I | 7.39 | 6.01 | 3.14E-04 | 2.66 | D | -257 | -236 | tactGGATTTTGTAATATCAGTATAaaaa | 201 | 5.49 | -7.65 |
| STM4113 | G | frwB | PTS system fructose-like IIB component 1 | 5.65 | 5.64 | 1.62E-03 | 2.89 | D | -83 | -62 | tttaGATTTTGAGATGAATTAAGCGAggaa | 202 | 4.79 | -7.09 |
| STM4119 | C | ppc | phosphoenolpyruvate carboxylase | 9.54 | 5.26 | 1.62E-04 | 3.40 | | | | | | | |
| STM4126 | C | udhA | soluble pyridine nucleotide transhydrogenase | 13.35 | 6.46 | 6.04E-06 | 3.17 | | | | | | | |
| STM4229 | G | malE | ABC superfamily (bind_prot) maltose transport protein, substrate recognition for transport and chemotaxis | 56.71 | 9.34 | 3.52E-13 | 7.00 | | | | | | | |
| STM4231 | G | lamB | phage lambda receptor protein; maltose high-affinity receptor, facilitates diffusion of maltose and maltoseoligosaccharides | 26.26 | 5.36 | 7.19E-07 | 11.38 | | | | | | | |
| STM4240 | S | yjbJ | putative cytoplasmic protein | -6.01 | 5.16 | 1.64E-03 | -4.24 | | | | | | | |

TABLE 3-continued

Differentially expressed genes and the presence/absence of putative FNR-binding motifs in their 5' regions.

| Locus[a] | Cat-ego-ry[b] | Name[c] | STM Gene Function[d] | t value[e] | DF[f] | Prot t[g] | Ratio[h] | Strand[i] | Start[j] | End[k] | Sequence[l] | SEQ ID NO: | Score[m] | In (P)[n] |
|---|---|---|---|---|---|---|---|---|---|---|---|---|---|---|
| STM4277 | P | nrfA | nitrite reductase periplasmic cytochrome c(552) | -7.36 | 5.12 | 6.58E-04 | -3.09 | R | -198 | -177 | acttACAATTGATTAAAGACAACATTttaa | 203 | 11.55 | -15.16 |
| STM4278 | — | nrfB | formate-dependent nitrite reductase; a penta-haeme cytochrome c | -7.18 | 7.31 | 1.46E-04 | -3.69 | D | -262 | -241 | gtttGAATATGCAACAAATCAACGCGgaga | 204 | 6.12 | -8.19 |
| STM4298 | G | melA | alpha-galactosidase | 25.01 | 5.44 | 7.96E-07 | 7.21 | | | | | | | |
| STM4299 | G | melB | GPH family, melibiose permease II | 24.57 | 5.24 | 1.29E-06 | 6.66 | D | -327 | -306 | cgatGATGCAGACCAACATCAACGTGcaaa | 205 | 4.94 | -7.21 |
| STM4300 | C | fumB | fumarase B (fumarase hydratase class I), anaerobic isozyme | 9.38 | 5.99 | 8.37E-05 | 2.69 | R | -216 | -195 | tgccGGGTTTGATTGGCGTGAGCGTCtcct | 206 | 4.17 | -6.62 |
| STM4301 | R | dcuB | Dcu family, anaerobic C4-dicarboxylate transporter | 12.46 | 5.83 | 2.01E-05 | 3.38 | R | -155 | -134 | ctggCCCATTGAATATTCGCCATTCtga | 207 | 5.55 | -7.7 |
| STM4305 | — | STM4305 | putative anaerobic dimethyl sulfoxide reductase, subunit A | -15.43 | 5.16 | 1.62E-05 | -10.14 | | | | | | | |
| STM4306 | C | STM4306 | putative anaerobic dimethyl sulfoxide reductase, subunit B | -7.45 | 5.19 | 5.86E-04 | -7.59 | R | -65 | -44 | cttaAGGAGTGATGTACGATGAAACAgtat | 208 | 4.33 | -6.73 |
| STM4307 | R | STM4307 | putative anaerobic dimethyl sulfoxide reductase, subunit C | -13.21 | 9.88 | 1.33E-07 | -2.90 | | | | | | | |
| STM4308 | R | STM4308 | putative component of anaerobic dehydrogenases | -7.84 | 6.73 | 1.27E-04 | -2.55 | | | | | | | |
| STM4398 | E | cycA | APC family, D-alanine/D-serine/glycine transport protein | 13.44 | 6.79 | 3.81E-06 | 2.54 | D | -151 | -130 | gccgATTCTTACCTAATATCGATGAGtcct | 209 | 5.02 | -7.27 |

TABLE 3-continued

Differentially expressed genes and the presence/absence of putative FNR-binding motifs in their 5' regions.

| Locus[a] | Category[b] | Name[c] | STM Gene Function[d] | t value[e] | DF[f] | Prot t[g] | Ratio[h] | Strand[i] | Start[j] | End[k] | Sequence[l] | SEQ ID NO: | Score[m] | In (P)[n] |
|---|---|---|---|---|---|---|---|---|---|---|---|---|---|---|
| STM4399 | D | ytfE | putative cell morphogenesis | 7.64 | 6.16 | 2.31E-04 | 2.96 | | | | | | | |
| STM4439 | C | cybC | cytochrome b(562) | 23.97 | 7.61 | 1.92E-08 | 4.26 | R | -317 | -296 | attcTGGGTTGAAAATGGTGAAATCCagta | 210 | 5.06 | -7.3 |
| STM4452 | F | nrdD | anaerobic ribonucleoside-triphosphate reductase | -12.74 | 6.51 | 7.62E-06 | -3.17 | R | -304 | -283 | ttttTACCTTGTTCTACATCAATAAAattg | 211 | 7.97 | -9.99 |
| STM4462 | — | yjgG | putative cytoplasmic protein | -5.83 | 5.39 | 1.64E-03 | -3.63 | | | | | | | |
| STM4463 | E | STM4463 | putative arginine repressor | -8.53 | 5.33 | 2.64E-04 | -5.52 | | | | | | | |
| STM4469 | E | argI | ornithine carbamoyltransferase 1 | -12.54 | 9.04 | 5.08E-07 | -3.36 | | | | | | | |
| STM4510 | M | STM4510 | putative aspartate racemase | -6.50 | 5.16 | 1.14E-03 | -6.35 | D | -115 | -94 | gcatTTTTTATATACACATCAAGTGatag | 212 | 6.58 | -8.61 |
| STM4511 | K | yjiE | putative transcriptional regulator, LysR family | -8.28 | 5.18 | 3.54E-04 | -6.79 | | | | | | | |
| STM4512 | — | iadA | isoaspartyl dipeptidase | -16.84 | 5.28 | 8.66E-06 | -6.59 | R | -75 | -54 | gcagCTTATTGTTGTTAATAAGGAGTTAtcat | 213 | 4.52 | -6.88 |
| STM4513 | S | yjiG | putative permease | -12.81 | 5.10 | 4.53E-05 | -8.61 | | | | | | | |
| STM4514 | — | yjiH | putative inner membrane protein | -31.77 | 6.17 | 4.45E-08 | -6.56 | R | -338 | -317 | gcgtGAAATTGACTAACGTCAAATTTattt | 214 | 9.1 | -11.31 |
| STM4526 | V | hsdR | endonuclease R, host restriction | -10.25 | 5.85 | 5.93E-05 | -3.28 | R | -153 | -132 | attgTTCGTTGATCACACACATATGaagt | 215 | 5.93 | -8.02 |
| STM4533 | N | tsr | methyl-accepting chemotaxis protein I, serine sensor receptor | -4.07 | 6.18 | 6.19E-03 | -2.75 | D | -301 | -280 | cgcgTAAAGTTAGGTAAATCAGTGAGtggt | 216 | 7.31 | -9.31 |

TABLE 3-continued

Differentially expressed genes and the presence/absence of putative FNR-binding motifs in their 5' regions.

| Locus[a] | Cat- ego- ry[b] | Name[c] | STM Gene Function[d] | t value[e] | DF[f] | Prot t[g] | Ratio[h] | Strand[i] | Start[j] | End[k] | Sequence[l] | SEQ ID NO: | Score[m] | In (P)[n] |
|---|---|---|---|---|---|---|---|---|---|---|---|---|---|---|
| STM4535 | G | STM4535 | putative PTS permease | 18.00 | 6.01 | 1.87E-06 | 8.22 | D | -179 | -158 | agaaCTTATCGAGCAAGATCAACAGTttta | 217 | 4.23 | -6.66 |
| STM4536 | G | STM4536 | putative PTS permease | 15.55 | 5.53 | 8.94E-06 | 4.50 | | | | | | | |
| STM4537 | G | STM4537 | putative PTS permease | 29.73 | 6.56 | 3.04E-08 | 6.57 | R | -172 | -151 | gttaGCGGATGAAATGACTCAACTTCggga | 218 | 5.44 | -7.61 |
| STM4538 | G | STM4538 | putative PTS permease | 12.87 | 5.17 | 4.03E-05 | 7.25 | | | | | | | |
| STM4539 | M | STM4539 | putative glucosamine- fructose-6- phosphate aminotransferase | 7.10 | 5.07 | 8.07E-04 | 8.20 | R | -277 | -256 | cggcCTCCATGATTGATATCACCATTccca | 219 | 5.1 | -7.33 |
| STM4540 | — | STM4540 | putative glucosamine- fructose-6- phosphate aminotransferase | 10.51 | 5.26 | 9.95E-05 | 4.89 | | | | | | | |
| STM4561 | R | osmy | hyperosmotically inducible periplasmic protein, RpoS-dependent stationary phase gene | -11.35 | 5.80 | 3.54E-05 | -5.19 | D | -163 | -142 | tcacGAATGTGATGCCAGTCATTGACttca | 220 | 4.12 | -6.59 |
| STM4565 | O | yjjW | pyruvate formate lyase activating enzyme | -15.96 | 9.55 | 3.30E-08 | -3.71 | D | -34 | -13 | gcgcTTTAGTCAGTAAGATCATTGCGtttt | 221 | 5.28 | -7.48 |
| STM4566 | — | yjjI | putative cytoplasmic protein | -20.43 | 5.09 | 4.43E-06 | -17.28 | R | -181 | -160 | actgTAATGAGATCTGAATCAAATTAtccc | 222 | 4.68 | -7 |
| STM4567 | F | deoC | 2-deoxyribose-5- phosphate aldolase | -6.83 | 6.15 | 4.34E-04 | -2.91 | D | -184 | -163 | gggaTAATTTGATTCAGATCTCATTAcagt | 223 | 4.68 | -7 |

TABLE 3-continued

Differentially expressed genes and the presence/absence of putative FNR-binding motifs in their 5' regions.

| Locus[a] | Category[b] | Name[c] | STM Gene Function[d] | t value[e] | DF[f] | Prot t[g] | Ratio[h] | Strand[i] | Start[j] | End[k] | Sequence[l] | SEQ ID NO: | Score[m] | ln(P)[n] |
|---|---|---|---|---|---|---|---|---|---|---|---|---|---|---|
| STM4568 | F | deoA | thymidine phosphorylase | −8.83 | 6.49 | 7.51E-05 | −2.76 | | | | | | | |

[a]Location of the open reading frame (ORF) in the *S. Typhimurium* LT2 genome.
[b]Functional category assigned to the gene by the National Center for Biotechnology Information, Cluster of Orthologous Genes (COGs). The designations of functional categories are as follows: C, energy production and conversion, D, cell cycle control and mitosis, E, amino acid metabolism and transport, F, nucleotide metabolism and transport, G, carbohydrate metabolism and transport, H, coenzyme metabolism and transport, I, lipid metabolism and transport, J, translation, K, transcription, L, replication, recombination, and repair, M, cell wall/membrane/envelope biogenesis, N, Cell motility, O, post-translational modification, protein turnover, chaperone functions, P, inorganic ion transport and metabolism, Q, secondary metabolites biosynthesis, transport, and catabolism, R, general functional prediction only (typically, prediction of biochemical activity), S, function unknown, T, signal transduction mechanisms, U, intracellular trafficking and secretion, V, defense mechanisms, −, not in COGs.
[c]Respective gene name or symbol.
[d]Functional classification according to the KEGG (Kyoto Encyclopedia of Genes and Genomes) database.
[e]The numerical value of t for the t test (statistical method).
[f]The degrees of freedom employed for the analysis of each gene.
[g]The probability associated with the t test for each gene.
[h]Ratio between the expression level of the fnr mutant relative to the wild-type.
[i]The strand on which the motif has been localized. R, reverse; D, direct; NA, not available in the Regulatory Sequence Analysis Tools (RSAT) database (the locus identity was not recognized), and a blank cell indicates that no motif was present.
[j]The starting position of the putative motif. The positions are relative to the region searched and span from −300 to +50 relative to the starting ATG.
[k]The ending position of the putative motif. The positions are relative to the region searched and span from −300 to +50 relative to the starting ATG.
[l]The sequence of the HIGHEST RANKING putative motif (capitalized letters) and 4 base pairs (bps) flanking either side of the region (lower case letters). A blank cell indicates that no motif was present. All of the sequences are reported from the 5' to the 3' end of the ORF (Open Reading Frame) analyzed.
[m]The score indicating the similarity of the motif to the information matrix. The cutoff used was a score higher than 4.00 or a ln(P) lower than −6.5.
[n]The natural logarithm of the probability that the putative motif is randomly similar to the information matrix. The cutoff used was a score higher than 4.00 or a ln(P) lower than −6.5.

We claim:

1. A method of inducing an immune response against a *Salmonella* species in a subject comprising administering to the subject an immunogenically effective amount of an attenuated *Salmonella* comprising an attenuating mutation in the Fumarate-Nitrate Reductase (fnr) gene, wherein the attenuating mutation in the fnr gene results in an attenuated *Salmonella* that (i) lacks flagella and is non-motile, and (ii) has reduced expression of SPI-1 genes, thereby resulting in reduced virulence.

2. The method of claim 1, wherein an immune response is induced against *S. enterica* serovar Typhimurium.

3. The method of claim 1, wherein the attenuating mutation in the fnr gene is an attenuating deletion mutation.

4. The method of claim 3, wherein at least about 95% of the fnr coding sequence is deleted.

5. The method of claim 3, wherein all of the fnr coding sequence is deleted.

6. The method of claim 3, wherein the deletion does not extend to genes that are 5' or 3' of the fnr gene.

7. The method of claim 1, wherein the attenuated *Salmonella* is avirulent.

8. The method of claim 1, wherein the attenuated *Salmonella* is administered by subcutaneous administration, intramuscular administration to skeletal muscle, intradermal administration, intravenous administration, intraperitoneal administration, topical administration, transmucosal administration, intratracheal administration, transdermal administration, intraventricular administration, intraarticular administration, intrathecal administration or inhalation administration.

9. The method of claim 1, wherein the attenuated *Salmonella* is administered orally.

10. The method of claim 1, wherein about $10^4$ to $10^9$ colony forming units of the attenuated *Salmonella* are administered to the subject.

11. The method of claim 1, wherein the subject is a mammalian subject.

12. The method of claim 11, wherein the mammalian subject is a feline, canine, equine, bovine or porcine subject.

13. The method of claim 11, wherein the mammalian subject is a human subject.

14. The method of claim 1, wherein the subject is an avian subject.

15. The method of claim 14, wherein the subject is a chicken subject.

16. The method of claim 1, wherein the method comprises administering to the subject an immunogenically effective amount of a pharmaceutical composition comprising the attenuated *Salmonella* comprising the attenuating mutation in the fnr gene in a pharmaceutically acceptable carrier.

17. A method of inducing an immune response against *Salmonella enterica* serovar Typhimurium (*S. Typhimurium*) in a subject comprising administering to the subject an immunogenically effective amount of an attenuated *S. Typhimurium* comprising an attenuating deletion mutation in the Fumarate-Nitrate Reductase (fnr) gene, wherein the attenuating deletion mutation in the fnr gene results in an attenuated *S. Typhimurium* that (i) lacks flagella and is non-motile, and (ii) has reduced expression of SPI-1 genes, thereby resulting in reduced virulence.

18. The method of claim 17, wherein the subject is a chicken subject.

19. The method of claim 17, wherein the subject is a human subject.

* * * * *

UNITED STATES PATENT AND TRADEMARK OFFICE
CERTIFICATE OF CORRECTION

PATENT NO.       : 8,101,168 B2
APPLICATION NO.  : 12/500366
DATED            : January 24, 2012
INVENTOR(S)      : Hassan et al.

It is certified that error appears in the above-identified patent and that said Letters Patent is hereby corrected as shown below:

In the Patent:

Column 3, Line 5: Please correct "C57Bl/6" to read -- C57BL/6 --
          Line 6: Please correct "C57Bl/6" to read -- C57BL/6 --
          Line 8: Please correct "C57Bl/6" to read -- C57BL/6 --

Column 4, Line 43: Please correct "E. albertfi" to read -- E. albertii --

Column 12, Line 4: Please correct "to 21 by" to read -- to 21 bp --
          Line 5: Please correct "by fragment" to read -- bp fragment --
          Line 7: Please correct "CCATGGTGAAT" to read -- CCATGGTGAAT --

Signed and Sealed this
Eighth Day of May, 2012

David J. Kappos
*Director of the United States Patent and Trademark Office*

SEQUENCE LISTING

<160> NUMBER OF SEQ ID NOS: 223

<210> SEQ ID NO 1
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 1
atatccatgg tgaatataca ggaaaaagtg c                              31

<210> SEQ ID NO 2
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 2
atatattcag ctgcatcaat ggtttagctg acg                            33

<210> SEQ ID NO 3
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 3
cgtacaacat cttaatcgta gc                                        22

<210> SEQ ID NO 4
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 4
ttcgttcaga tcattattac cc                                        22

<210> SEQ ID NO 5
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 5
gccaatttca aaaatatgac g                                         21

<210> SEQ ID NO 6
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 6
gtccagaaac tgaataagtt cg                                        22

<210> SEQ ID NO 7
<211> LENGTH: 22
<212> TYPE: DNA

```
<213> ORGANISM: Artificial sequence
<220> FEATURE:
<223> OTHER INFORMATION: Synthetic oligonucleotide

<400> SEQUENCE: 7
tatttagctc cattacctac gg                                              22

<210> SEQ ID NO 8
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 8
ggaattcata gagttccatc c                                               21

<210> SEQ ID NO 9
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 9
taacctttcg ctttaatact cc                                              22

<210> SEQ ID NO 10
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 10
gatatcaaca atgcctttaa gc                                              22

<210> SEQ ID NO 11
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 11
agcgtcttat caaagagtat gg                                              22

<210> SEQ ID NO 12
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 12
tcaccgtagt gattaagata acc                                             23

<210> SEQ ID NO 13
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 13
ttgctatcgt ctaaaaatag gc                                              22
```

```
<210> SEQ ID NO 14
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 14
ttgatattat cgtcagagat tcc                                              23

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
ggatatcgag acacttgagc                                                  20

<210> SEQ ID NO 16
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 16
gattaaatgg gtattactga acg                                              23

<210> SEQ ID NO 17
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 17
caacagctta ttgatttagt gg                                               22

<210> SEQ ID NO 18
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 18
ctaacgattt ttcttcaatg g                                                21

<210> SEQ ID NO 19
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 19
aagcgaatac agctatgaac c                                                21

<210> SEQ ID NO 20
<211> LENGTH: 21
<212> TYPE: DNA
<213> ORGANISM: Artificial sequence
<220> FEATURE:
<223> OTHER INFORMATION: Synthetic oligonucleotide
```

```
-continued

<400> SEQUENCE: 20
attagctttt gcagaacatg g                                              21

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
aaggtatcag ccagtctacg                                                20

<210> SEQ ID NO 22
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 22
cgtatggata aggataaatt cg                                             22

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
taagccagca ggtagatacg                                                20

<210> SEQ ID NO 24
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 24
cgacataaag agatcgataa cc                                             22

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
aggacaaatc gtatgtaccg                                                20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
accagcagta cccactctcc                                                20

<210> SEQ ID NO 27
<211> LENGTH: 21
<212> TYPE: DNA
```

<213> ORGANISM: Artificial sequence
<220> FEATURE:
<223> OTHER INFORMATION: Synthetic oligonucleotide

<400> SEQUENCE: 27
ggtaaaagag cagcataaag c                                             21

<210> SEQ ID NO 28
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 28
attatcactc aagaccttac gc                                            22

<210> SEQ ID NO 29
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 29
aataaagaac gcattattca gg                                            22

<210> SEQ ID NO 30
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 30
gttaaagtca taatgccaat cg                                            22

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
agcgacatta atatggaacg                                               20

<210> SEQ ID NO 32
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 32
tttactctgt aagtagctct gc                                            22

<210> SEQ ID NO 33
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 33
tgattaaact caagctgaaa gg                                            22

```
<210> SEQ ID NO 34
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 34
ccgaaatttt atagacaaag acc                                              23

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
gaacagaata tcgtgcaacc                                                  20

<210> SEQ ID NO 36
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 36
gagtctgatt ttctctttgt cg                                               22

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
ggttatcggt acagttttcg                                                  20

<210> SEQ ID NO 38
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 38
tagattttgt gtatttcgaa cg                                               22

<210> SEQ ID NO 39
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 39
gactaactct ctgtcgaaaa cc                                               22

<210> SEQ ID NO 40
<211> LENGTH: 21
<212> TYPE: DNA
<213> ORGANISM: Artificial sequence
<220> FEATURE:
<223> OTHER INFORMATION: Synthetic oligonucleotide
```

<400> SEQUENCE: 40
attttatggt cggtgtagag c                                              21

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
cgatgtctct gaagaagtgc                                                20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
ttcaaccatc tctttcttcg                                                20

<210> SEQ ID NO 43
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 43
cttcgctatc aggatgagg                                                 19

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
cgaacaatag actgcttacg                                                20

<210> SEQ ID NO 45
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 45
ggctcgtcag gttttagc                                                  18

<210> SEQ ID NO 46
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 46
cttgctcatc gtgtttcg                                                  18

<210> SEQ ID NO 47
<211> LENGTH: 19
<212> TYPE: DNA

```
<213> ORGANISM: Artificial sequence
<220> FEATURE:
<223> OTHER INFORMATION: Synthetic oligonucleotide

<400> SEQUENCE: 47
attcgctggt atcgtctcc                                                19

<210> SEQ ID NO 48
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 48
gaacctcgtt catatacgg                                                19

<210> SEQ ID NO 49
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 49
gattacacca tgggactgg                                                19

<210> SEQ ID NO 50
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 50
cagagactca tcttcagtac g                                             21

<210> SEQ ID NO 51
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 51
aggcggcatt tagtcagg                                                 18

<210> SEQ ID NO 52
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 52
gacaggtaag ctccacagc                                                19

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
ggtaccagaa atacagatgg                                               20
```

```
<210> SEQ ID NO 54
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 54
gccgatatca atcgatgc                                                       18

<210> SEQ ID NO 55
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 55
tttctttttt gatatatgtc ttttcatgta                                          30

<210> SEQ ID NO 56
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 56
ggaattggtt gaaataaat atatcg                                               26

<210> SEQ ID NO 57
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 57
gaataatggc tatcgaaatc aaagtaccgg                                          30

<210> SEQ ID NO 58
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 58
tttataatat atatttaatc aattattttg                                          30

<210> SEQ ID NO 59
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 59
tctggattat gtggaacctc aactacaaca                                          30

<210> SEQ ID NO 60
<211> LENGTH: 30
<212> TYPE: DNA
<213> ORGANISM: Artificial sequence
<220> FEATURE:
<223> OTHER INFORMATION: Synthetic oligonucleotide
```

<400> SEQUENCE: 60
tatcgggatg gaactctatg aattccatca                               30

<210> SEQ ID NO 61
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 61
aacctgattt gttcaaggac gttattaaca                               30

<210> SEQ ID NO 62
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 62
ccgtggaatt gaggtcgtta aatgagactc                               30

<210> SEQ ID NO 63
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 63
ctggtgcatt gatgataagg agaattgaat                               30

<210> SEQ ID NO 64
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 64
aagggaaaat gattatgagc aatgagactt                               30

<210> SEQ ID NO 65
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 65
gcgtgacatt gataaagatc accacgccag                               30

<210> SEQ ID NO 66
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 66
actggcagtc gatgaagctc attattctgc                               30

<210> SEQ ID NO 67
<211> LENGTH: 30
<212> TYPE: DNA

```
<213> ORGANISM: Artificial sequence
<220> FEATURE:
<223> OTHER INFORMATION: Synthetic oligonucleotide

<400> SEQUENCE: 67
tttcggagta gatgtatgtc aatagactgg                                        30

<210> SEQ ID NO 68
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 68
taggattttt gcctctgaac ggtgcggcgc                                        30

<210> SEQ ID NO 69
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 69
ggaagtcact gatatagcag aaatactggc                                        30

<210> SEQ ID NO 70
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 70
tccattaatc aactgttaac aaaggatatt                                        30

<210> SEQ ID NO 71
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 71
acatgaatat caggcaaaac aacttttgc                                         30

<210> SEQ ID NO 72
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 72
gccataaatt gatcgctgtc gaaaaaagca                                        30

<210> SEQ ID NO 73
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 73
cagaattgtt cctgatgttc aaatttgcac                                        30
```

```
<210> SEQ ID NO 74
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 74
tgttcgtacc gatcattctg atctacacca                                30

<210> SEQ ID NO 75
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 75
cacgtgcact gttggaagag gttatccgac                                30

<210> SEQ ID NO 76
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 76
agtttatttt tctttctatc aaataatgtc                                30

<210> SEQ ID NO 77
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 77
tttaatcgtt aatgggtatg ataaccgct                                 30

<210> SEQ ID NO 78
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 78
ctactttttc gatatatatc agactttata                                30

<210> SEQ ID NO 79
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 79
gtaagaaacc gatttgcgtc gaatcctgcc                                30

<210> SEQ ID NO 80
<211> LENGTH: 30
<212> TYPE: DNA
<213> ORGANISM: Artificial sequence
<220> FEATURE:
<223> OTHER INFORMATION: Synthetic oligonucleotide
```

```
<400> SEQUENCE: 80
aataattctc aacataattc agatgtgtcc                              30

<210> SEQ ID NO 81
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 81
ggcgagatat gatctatatc aaattctcat                              30

<210> SEQ ID NO 82
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 82
cgtgcgcgct gaaatgcgtt aacatgatcc                              30

<210> SEQ ID NO 83
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 83
attaattatt gttataaatc aaagaaatgg                              30

<210> SEQ ID NO 84
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 84
tgtaaatggt gtgttaaatc gattgtgaat                              30

<210> SEQ ID NO 85
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 85
cctgaagcct gtttgaacgc aatatcggat                              30

<210> SEQ ID NO 86
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 86
cggagtattt tatgaaaatc aacaaatatc                              30

<210> SEQ ID NO 87
<211> LENGTH: 30
<212> TYPE: DNA
```

```
<213> ORGANISM: Artificial sequence
<220> FEATURE:
<223> OTHER INFORMATION: Synthetic oligonucleotide

<400> SEQUENCE: 87
ttcggcaatt gatatgactt aaaaattaat                                         30

<210> SEQ ID NO 88
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 88
cgtgaaagtt ttcaatcaac aaaagaattt                                         30

<210> SEQ ID NO 89
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 89
agaataatgt gatgtaaatc acccttaact                                         30

<210> SEQ ID NO 90
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 90
cgtaaccctc gatgaggata aataaatgag                                         30

<210> SEQ ID NO 91
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 91
gcaattcttt gattggcctt cttttcgtcg                                         30

<210> SEQ ID NO 92
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 92
cggaagagat catggtgatc aatgccggcg                                         30

<210> SEQ ID NO 93
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 93
ggttgtattt gcgttttatc agaatatgta                                         30
```

```
<210> SEQ ID NO 94
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 94
aggattgttc gatgtccaac aatggctcgt                                              30

<210> SEQ ID NO 95
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 95
aactcaagct gattgcccctt gccatatctt                                             30

<210> SEQ ID NO 96
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 96
atacaaatct ggtggaaatc gaaaaaatct                                              30

<210> SEQ ID NO 97
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 97
ataatttcgt tatagttatc aatatatagc                                              30

<210> SEQ ID NO 98
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 98
ccgtgagctt gatcaaaaac aaaaaaaatt                                              30

<210> SEQ ID NO 99
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 99
tgctttattc atcaaacatc aaaatcagtc                                              30

<210> SEQ ID NO 100
<211> LENGTH: 30
<212> TYPE: DNA
<213> ORGANISM: Artificial sequence
<220> FEATURE:
<223> OTHER INFORMATION: Synthetic oligonucleotide
```

```
<400> SEQUENCE: 100
tcgccggtct gatttaccac tacatcggta                                          30

<210> SEQ ID NO 101
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 101
accctgattt aacttacgtc aagtggaaac                                          30

<210> SEQ ID NO 102
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 102
tgcctgattt tatgttggtc aatctgtgtg                                          30

<210> SEQ ID NO 103
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 103
gtgccccgtt gcttgttgac actttattca                                          30

<210> SEQ ID NO 104
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 104
tgaataaagt gtcaacaagc aacggggcac                                          30

<210> SEQ ID NO 105
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 105
tcattatatg tatgactatc aattattttt                                          30

<210> SEQ ID NO 106
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 106
ttaactatca gattacagag aatatcaatg                                          30

<210> SEQ ID NO 107
<211> LENGTH: 30
<212> TYPE: DNA
```

<213> ORGANISM: Artificial sequence
<220> FEATURE:
<223> OTHER INFORMATION: Synthetic oligonucleotide

<400> SEQUENCE: 107
ttattgaatt aaacggtaac atctcttttt                                              30

<210> SEQ ID NO 108
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 108
caaaaatgtt gagaaatatc agcgtcagga                                              30

<210> SEQ ID NO 109
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 109
tgttaaaatt gacaaatatc aattacggct                                              30

<210> SEQ ID NO 110
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 110
gggtggaatc aatctgaata aaaaactatg                                              30

<210> SEQ ID NO 111
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 111
gttctaaatt aatctggatc aataaatgtt                                              30

<210> SEQ ID NO 112
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 112
atttcacatt gttgataagt attttcattt                                              30

<210> SEQ ID NO 113
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 113
acgaagaatc gatttccgcc atgttcgagc                                              30

<210> SEQ ID NO 114
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 114
acataacatt gatacatgtc gttatcataa                                       30

<210> SEQ ID NO 115
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 115
tggcgataac gccggcaatc aaaccaaaaa                                       30

<210> SEQ ID NO 116
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 116
cctccacatt gaacggcaaa aaatcgggta                                       30

<210> SEQ ID NO 117
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 117
atccgaaact gaaaatgatg gatttaattg                                       30

<210> SEQ ID NO 118
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 118
ttggttatgc gatggttatc aatatgatgc                                       30

<210> SEQ ID NO 119
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 119
agcagatgtt ggcgaaaatc agtgccggac                                       30

<210> SEQ ID NO 120
<211> LENGTH: 30
<212> TYPE: DNA
<213> ORGANISM: Artificial sequence
<220> FEATURE:
<223> OTHER INFORMATION: Synthetic oligonucleotide

```
<400> SEQUENCE: 120
gggcattgtt gtgatcctgc aaagcgcggg                                30

<210> SEQ ID NO 121
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 121
ggatattagc gatttttatc agacattttt                                30

<210> SEQ ID NO 122
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 122
atgcgccgcc gattgccgtg gaatttggtc                                30

<210> SEQ ID NO 123
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 123
tctcgtctgt catgcacatc aacactttct                                30

<210> SEQ ID NO 124
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 124
acaggaaaac ccgttacatc aactgctgga                                30

<210> SEQ ID NO 125
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 125
acgcagggct gtttatcgtg aattcactgt                                30

<210> SEQ ID NO 126
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 126
cttaactact gtttgcaatc aaaaaggaag                                30

<210> SEQ ID NO 127
<211> LENGTH: 30
<212> TYPE: DNA
```

<213> ORGANISM: Artificial sequence
<220> FEATURE:
<223> OTHER INFORMATION: Synthetic oligonucleotide

<400> SEQUENCE: 127
acgccacgct gaaaagcctg acaaaacagt                                30

<210> SEQ ID NO 128
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 128
aacaaaaact gattgccgcc attaaagaga                                30

<210> SEQ ID NO 129
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 129
atttttcatt gaagtttcac aagttgcata                                30

<210> SEQ ID NO 130
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 130
cttctttttt atcgttaatc tatttattat                                30

<210> SEQ ID NO 131
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 131
ggtagaaaac cacatgaatc agagtctgct                                30

<210> SEQ ID NO 132
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 132
tcccataaag gattcacttc aatggcatac                                30

<210> SEQ ID NO 133
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 133
acggttcgat gatcggcctg aataaagata                                30

```
<210> SEQ ID NO 134
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 134
ggggataact gaatatcccc aataataatt                                          30

<210> SEQ ID NO 135
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 135
tggtgccggt gattaccgtg atctccacct                                          30

<210> SEQ ID NO 136
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 136
tgtttatgct gattgggctg gaaatcatga                                          30

<210> SEQ ID NO 137
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 137
gagcgcgaat gaaatcaatc aaatcattaa                                          30

<210> SEQ ID NO 138
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 138
tcctgcgcat gatgttaatc ataaatgtca                                          30

<210> SEQ ID NO 139
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 139
gctcaatgag gccattcatc aactggaggt                                          30

<210> SEQ ID NO 140
<211> LENGTH: 30
<212> TYPE: DNA
<213> ORGANISM: Artificial sequence
<220> FEATURE:
<223> OTHER INFORMATION: Synthetic oligonucleotide
```

```
<400> SEQUENCE: 140
aaaaagtatt aagaaactc aatattgacg                               30

<210> SEQ ID NO 141
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 141
tttaaaaggt gacaataatg aaaatcatgg                              30

<210> SEQ ID NO 142
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 142
gtttattgat aatgattatc aagtgcattt                              30

<210> SEQ ID NO 143
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 143
aacggaggct gccaatgatc aatgccctgg                              30

<210> SEQ ID NO 144
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 144
ccgcattact cacggtcatc aacgcgctga                              30

<210> SEQ ID NO 145
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 145
aaataggatt gaacatcatg aatcaacagg                              30

<210> SEQ ID NO 146
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 146
tggaagaagt gttcccgatc agcttcaaag                              30

<210> SEQ ID NO 147
<211> LENGTH: 30
<212> TYPE: DNA
```

-continued

```
<213> ORGANISM: Artificial sequence
<220> FEATURE:
<223> OTHER INFORMATION: Synthetic oligonucleotide

<400> SEQUENCE: 147
ctatcgcgct gttgggccgc taattcaggg                                30

<210> SEQ ID NO 148
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 148
cgtggacgct gaactacgac gaaatcgaca                                30

<210> SEQ ID NO 149
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 149
aaacggcgat gatcgctggc gatttagcga                                30

<210> SEQ ID NO 150
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 150
ttctcttagt gatctacctc accttttaca                                30

<210> SEQ ID NO 151
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 151
gaaataaatt gatctgccac aggttctgga                                30

<210> SEQ ID NO 152
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 152
ttatgaattt catttaattt aaagttaatg                                30

<210> SEQ ID NO 153
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 153
agatgcattt gatatacatc attagatttt                                30
```

-continued

```
<210> SEQ ID NO 154
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 154
tatgttaatt caaaaaaatc aatctatcag                                30

<210> SEQ ID NO 155
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 155
tcgtcagtct gatcatcctg atgttctacg                                30

<210> SEQ ID NO 156
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 156
ggtttttatt gatttaaatc aaagaatgaa                                30

<210> SEQ ID NO 157
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 157
ttgaccggct gcttgatgtc accttacctc                                30

<210> SEQ ID NO 158
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 158
aggtgaatat gggactttc aattttgtaa                                 30

<210> SEQ ID NO 159
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 159
catagagatt gatgaaactg aagattaatg                                30

<210> SEQ ID NO 160
<211> LENGTH: 30
<212> TYPE: DNA
<213> ORGANISM: Artificial sequence
<220> FEATURE:
<223> OTHER INFORMATION: Synthetic oligonucleotide
```

```
<400> SEQUENCE: 160
agcccacttt aatttaacgt aaataaggaa                              30

<210> SEQ ID NO 161
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 161
agcccacttt aatttaacgt aaataaggaa                              30

<210> SEQ ID NO 162
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 162
ccgcttgatt aaattacggt aaaatctgag                              30

<210> SEQ ID NO 163
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 163
ggagtaagta atggattatc aaaataatgt                              30

<210> SEQ ID NO 164
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 164
cttaggcgtt gagatccatg aatggctgag                              30

<210> SEQ ID NO 165
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 165
tttagaactc cagattatac aaattcagga                              30

<210> SEQ ID NO 166
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 166
gcttttcatt gacttgggag aatatcgtcc                              30

<210> SEQ ID NO 167
<211> LENGTH: 30
<212> TYPE: DNA
```

```
<213> ORGANISM: Artificial sequence
<220> FEATURE:
<223> OTHER INFORMATION: Synthetic oligonucleotide

<400> SEQUENCE: 167 ccgctaatttt gatggatctc attacactta                                    30

<210> SEQ ID NO 168
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 168 tccggtatttt cattttccag aatattgtcc                                    30

<210> SEQ ID NO 169
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 169 cacattttttc tagtgagatc aaagagctga                                    30

<210> SEQ ID NO 170
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 170 ctattgatttt gctgtggaac aagaaaacgc                                    30

<210> SEQ ID NO 171
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 171
actgccacct gatcaacaag gagataaatc                                     30

<210> SEQ ID NO 172
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 172
gtataccact gatcgtaaag gatatttagt                                     30

<210> SEQ ID NO 173
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 173
tctacctatt aataggtata aactcagtta                                     30
```

```
<210> SEQ ID NO 174
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 174
aaaggttgtc cacgctaaac aatttcataa                                    30

<210> SEQ ID NO 175
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 175
aaggcgcttc gttgtacctg attattatta                                    30

<210> SEQ ID NO 176
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 176
ggatgcgatt gaacatccgg aaaactaccc                                    30

<210> SEQ ID NO 177
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 177
tgaccatcct gaatattgtc tacaaattgt                                    30

<210> SEQ ID NO 178
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 178
cctgtttttt gattgaaatc aggctaagtt                                    30

<210> SEQ ID NO 179
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 179
acgcaaaatt gttaacgaac agggatttta                                    30

<210> SEQ ID NO 180
<211> LENGTH: 30
<212> TYPE: DNA
<213> ORGANISM: Artificial sequence
<220> FEATURE:
<223> OTHER INFORMATION: Synthetic oligonucleotide
```

```
<400> SEQUENCE: 180
taaaatccct gttcgttaac aattttgcgt                                              30

<210> SEQ ID NO 181
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 181
agtgattatt gccgactatc tgttgaaccg                                              30

<210> SEQ ID NO 182
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 182
gcttgcttat gatggcacac aattcatcta                                              30

<210> SEQ ID NO 183
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 183
cgacgctgct gttcatcggc aatatcgtct                                              30

<210> SEQ ID NO 184
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 184
agcgtgattt gatgtaaggt taattttat                                               30

<210> SEQ ID NO 185
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 185
cacaataggt tacgtccctc aatgtaaagc                                              30

<210> SEQ ID NO 186
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 186
aacgcgcgtt aaacttcctg aaaaaatatg                                              30

<210> SEQ ID NO 187
<211> LENGTH: 30
<212> TYPE: DNA
```

```
<213> ORGANISM: Artificial sequence
<220> FEATURE:
<223> OTHER INFORMATION: Synthetic oligonucleotide

<400> SEQUENCE: 187
cgcaacagtt gattgtcggc gataaaatac                                          30

<210> SEQ ID NO 188
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 188
ggcgttatta aatgtagatc aattatcggt                                          30

<210> SEQ ID NO 189
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 189
ttcgggttat gttgcagttc attctccgac                                          30

<210> SEQ ID NO 190
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 190
ccgcaaaatt aaataacatt atcatccctg                                          30

<210> SEQ ID NO 191
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 191
tgtcattatc catacacaac aatattggca                                          30

<210> SEQ ID NO 192
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 192
taacgatatt gctgccgata agcccgcgc                                           30

<210> SEQ ID NO 193
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 193
gcacgctgct gatcagcatc gtgtt                                               25
```

```
<210> SEQ ID NO 194
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 194
tgtaattatt gataccaatc aatatccatg                                    30

<210> SEQ ID NO 195
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 195
acggtatttt ctgtttgatt aatgaggtta                                    30

<210> SEQ ID NO 196
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 196
cgcgcagcgt gatgtagctg aaatcct                                       27

<210> SEQ ID NO 197
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 197
catttggcct gacctgaatc aattcagcag                                    30

<210> SEQ ID NO 198
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 198
aagaatggct gatttagatg atattaaaga                                    30

<210> SEQ ID NO 199
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 199
ctacgagttt gttatgagac gagaacttgc                                    30

<210> SEQ ID NO 200
<211> LENGTH: 30
<212> TYPE: DNA
<213> ORGANISM: Artificial sequence
<220> FEATURE:
<223> OTHER INFORMATION: Synthetic oligonucleotide
```

```
<400> SEQUENCE: 200
tcattatgct gacgcttaac aaacacgccg                              30

<210> SEQ ID NO 201
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 201
tactggattt ttgtaatatc agtataaaaa                              30

<210> SEQ ID NO 202
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 202
tttagatttt gagatgaatt aagcgaggaa                              30

<210> SEQ ID NO 203
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 203
acttacaatt gattaaagac aacattttaa                              30

<210> SEQ ID NO 204
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 204
gtttgaatat gcaacaaatc aacgcggaga                              30

<210> SEQ ID NO 205
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 205
cgatgatgca gaccaacatc aacgtgcaaa                              30

<210> SEQ ID NO 206
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 206
tgccgggttt gattggcgtg agcgtctcct                              30

<210> SEQ ID NO 207
<211> LENGTH: 30
<212> TYPE: DNA
```

```
<213> ORGANISM: Artificial sequence
<220> FEATURE:
<223> OTHER INFORMATION: Synthetic oligonucleotide

<400> SEQUENCE: 207
ctggcgcatt gaatattcgc catttcctga                                    30

<210> SEQ ID NO 208
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 208
cttaaggagt gatgtacgat gaaacagtat                                    30

<210> SEQ ID NO 209
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 209
gccgattctt acctaatatc gatgagtcct                                    30

<210> SEQ ID NO 210
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 210
attctgggtt gaaaatggtg aaatccagta                                    30

<210> SEQ ID NO 211
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 211
tttttacctt gttctacatc aataaaattg                                    30

<210> SEQ ID NO 212
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 212
gcatttttta tatacacatc aagttgatag                                    30

<210> SEQ ID NO 213
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 213
gcagcttatt gtttaataag gagttatcat                                    30
```

<210> SEQ ID NO 214
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 214
gcgtgaaatt gactaacgtc aaatttattt                                    30

<210> SEQ ID NO 215
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 215
attgttcgtt gatcacacac aatatgaagt                                    30

<210> SEQ ID NO 216
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 216
cgcgtaaagt taggtaaatc agtgagtggt                                    30

<210> SEQ ID NO 217
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 217
agaacttatc gagcaagatc aacagtttta                                    30

<210> SEQ ID NO 218
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 218
gttagcggat gaaatgactc aacttcggga                                    30

<210> SEQ ID NO 219
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 219
cggcctccat gattgatatc accattccca                                    30

<210> SEQ ID NO 220
<211> LENGTH: 30
<212> TYPE: DNA
<213> ORGANISM: Artificial sequence
<220> FEATURE:
<223> OTHER INFORMATION: Synthetic oligonucleotide

```
<400> SEQUENCE: 220
tcacgaatgt gatgccagtc attgacttca                                              30

<210> SEQ ID NO 221
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 221
gcgctttagt cagtaagatc attgcgtttt                                              30

<210> SEQ ID NO 222
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 222
actgtaatga gatctgaatc aaattatccc                                              30

<210> SEQ ID NO 223
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 223
gggataattt gattcagatc tcattacagt                                              30
```